(12) United States Patent
Nielsen et al.

(10) Patent No.: US 10,314,860 B2
(45) Date of Patent: Jun. 11, 2019

(54) COMPOSITIONS AND METHODS FOR TREATING AND PREVENTING VENOM RELATED POISONING

(71) Applicant: Arizona Board of Regents on Behalf of the University of Arizona, Tucson, AZ (US)

(72) Inventors: Vance G. Nielsen, Tucson, AZ (US); Leslie V. Boyer, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/576,062

(22) PCT Filed: May 20, 2016

(86) PCT No.: PCT/US2016/033542
§ 371 (c)(1),
(2) Date: Nov. 21, 2017

(87) PCT Pub. No.: WO2016/187545
PCT Pub. Date: Nov. 24, 2016

(65) Prior Publication Data
US 2018/0177826 A1  Jun. 28, 2018

Related U.S. Application Data

(60) Provisional application No. 62/164,916, filed on May 21, 2015.

(51) Int. Cl.

| | |
|---|---|
| *A61K 33/26* | (2006.01) |
| *A61K 31/295* | (2006.01) |
| *A61K 45/06* | (2006.01) |
| *A61K 31/28* | (2006.01) |
| *A61K 31/69* | (2006.01) |
| *A61P 39/02* | (2006.01) |
| *A61K 33/24* | (2019.01) |

(52) U.S. Cl.
CPC .............. *A61K 33/26* (2013.01); *A61K 31/28* (2013.01); *A61K 31/295* (2013.01); *A61K 31/69* (2013.01); *A61K 33/24* (2013.01); *A61K 45/06* (2013.01); *A61P 39/02* (2018.01)

(58) Field of Classification Search
CPC ........ A61K 33/26; A61K 31/28; A61K 45/06; A61P 39/02
See application file for complete search history.

(56) References Cited

U.S. PATENT DOCUMENTS

| | | |
|---|---|---|
| 6,020,181 A | 2/2000 | Bini |
| 2004/0131703 A1 | 7/2004 | Bach et al. |
| 2007/0041979 A1 | 2/2007 | Raju et al. |
| 2010/0196516 A1 | 8/2010 | Nobre et al. |
| 2012/0045518 A1* | 2/2012 | Nielsen .................. A61K 31/28 424/530 |

OTHER PUBLICATIONS

Ownby et al., title: Hemorrhagic toxins from rattlesnake (*Crotalus atrox*) venom. Pathogenesis of hemorrhage induced by three purified toxins; Am J Pathol.; vol. 93, No. (1); pp. 201-218; published Oct. 1978 (Year: 1978).*
Ali AJ, et al., Lack of Coagulopathy After Copperhead Snakebites, Ann Emerg Med, 2015; vol. 65, pp. 404-409.
Arkenbauer MR, et al., Carbon monoxide and nitric acid oxide modulate . . . , Blood Coagul Fibrinolysis, 2011, vol. 22, pp. 712-719.
Bajwa SS, et al., Fibrinolytic and Fibrinogen Clotting Enzymes Present in the Venoms of Western Diamondback . . . , Toxicon, 1981, vol. 19, pp. 53-59.
Bajwa SS, et al., Thrombin-like and Fibrinolytic Enzymes in the Venoms from the Gaboon Viper . . . , Toxicon, 1982, vol. 20, pp. 427-432.
Baramova EN, et al., Internation of Hemorrhagic Metalloproteinases with Human alpha2-Macroglubulin, Biochemistry, 1990, vol. 29, pp. 1069-1074.
Bell WR., Befibrinogenating Enzymes, Drugs, 1997, vol. 54, No. 3, pp. 18-31.
Budzynski AZ, et al., Fibrinogenolytic Afibrinogenemia After Envenomation by Western Diamondback Rattlesnake (*Crotalus atrox*), Blood, 1984, vol. 63, pp. 1-14.
Bush SP, et al., Crotalide Polyvalent Immune Fab (Ovine) Antivenom is Efficacious for Envenomations by Southern Pacific Rattlesnakes (*Crotalus helleri*), Ann Emerg Med 2002, vol. 40, pp. 619-624.
Chinnasamy S, et al., Zn2+ ion of the snake venom metalloproteinase (SVMP) plays a critical role . . . , RSC Adv. 2015, vol. 5, pp. 70566-70576.
Chiou SH, et al., Characterization of a Protease with Alpha- and Beta-Fibrinogenase Activity from the Western Diamondback Rattlesnake, *Crotalus atrox*, Biochem Biophys Res Comm. 1992, vol. 187, No. 1, pp. 389-396.
Cohen JB, et al., Carbon monoxide releasing molecule-2 enhances coagulation and attenuates . . . , Blood Coagul Fibrinolysis, Jan. 2011, pp. 60-66.
Cruz NS, Rattlesnake bite complications in 19 children, Alvarez RG. Pediatr Emerg Care 1994, vol. 10, pp. 30-33.
Evans CS, et al., The Copperhead Coagulopathy Conundrum, Ann Emerg Med 2015, vol. 65, pp. 467-468.
Fazelat J, et al., Recurrent hemorrhage after western diamondback rattlesnake envenomation treated with crotalidae polyvalent immune fab (ovine), Clin Toxicol (Phila) 2008, vol. 46, pp. 823-826.
Hahn BS, et al., Purification and characterization of piscivorase I and II, the fibrinolytic enzymes . . . , Toxicon 1995, vol. 33, pp. 929-941.
Hasiba U, et al., DIC-like syndrome after envenomation by the snake, N Engl J Med 1975, vol. 292, pp. 505-507.

(Continued)

*Primary Examiner* — Yanzhi Zhang
(74) *Attorney, Agent, or Firm* — Casimir Jones, S.C.; Robert A. Goetz

(57) ABSTRACT

This invention relates to compositions and methods for treating, ameliorating and preventing the toxic effects of venom poisoning. In particular, the invention provides compositions comprising carbon monoxide releasing molecules (CORM) or compositions comprising CORM and iron releasing molecules (IRM) for one or more of enhancing coagulation, reducing fibrinolysis, and/or inactivating venom related metalloproteinase activity in a subject suffering from or at risk of suffering from venom poisoning.

12 Claims, 20 Drawing Sheets

(56) References Cited

OTHER PUBLICATIONS

International Search Report & Written Opinion, International Patent Application No. PCT/US2016/033542, dated Aug. 17, 2016.
Jia Y, et al., cDNA cloning, expression and fibrin(ogen)olytic activity of two low-molecular weight snake venom metalloproteinases, Toxicon 2009, vol. 54, pp. 233-243.
Johnson EK, et al., Isolation of a hemorrhagic toxin from the venom of Agkistrodon Contortrix Laticinctus . . . ,Int J Biochem 1993, vol. 25, pp. 267-678.
Kini RM. Serine Proteases Affecting Blood Coagulation and Fibrinolysis from Snake Venoms, Pathophysiol Haemost Thromb 2005, vol. 34, pp. 200-204.
Kitchens C1, et al., Fatality in a Case of Envenomation by Crotalus adamanteus Initially Successfully Treated with Polyvalent Ovine . . . ,, J Med Toxicol 2008, vol. 4, pp. 180-183.
Kitchens CS, et al., Mechanism of Defibrination in Humans After Envenomation by the Eastern Diamondback Rattlesnake, Am J Hematol 1983, vol. 14, pp. 345-353.
Komori Y, et al., Biochemical and physiological studies on a kallikrein-like enzyme from the venom of *Crotalus viridis viridis* (Prairie rattlesnake), Biochim Biophys Acta 1988, vol. 967, pp. 92-102.
Komori Y, et al., Biochemical characterization of hemorrhagic toxin from *Crotalus viridis viridis* (Prairie rattlesnake) venom, Virilnt J Biochem 1994, vol. 26, pp. 1411-1418.
Komori Y, et al., Isolation and Biochemical Characterization of Rubelase, a Non-Hemorrhagic Elastase from *Crotalus ruber ruber* (Red Rattlesnake) Venom, Toxins (Basel) 2011, vol. 3, pp. 900-910.
Kramkowski et al. "Antithrombotic properities of water-soluble carbon monoxide-releasing molecules" Arterioscler Thromb Vasc Biol, Sep. 2012, p. 2149-57.
Kshirsagar AV, et al., Intravenous Iron Supplementaion Practices and Short-Term Risk of Cardiovascular Events in Hemodialysis Patients, PLoS ONE 2013; 8:e78930.
Lavonas EJ, et al., Initial Experience with Crotalidae Polyvalent Immune Fab (Ovine) Antivenom in the Treatment of Copperhead Snakebite, Ann Emerg Med 2004, vol. 43, pp. 200-206.
Lefkowitz RY, et al., Reality Bites: A case of severe rattlesnake envenomation, J Intensive Care Med 2013, vol. 28, pp. 314-319.
Machovec KA, et al., The procoagulant properties of purified fibrinogen concentrate are enhanced by carbon monoxide releasing molecule-2, Thromb res, Jun. 2012, p. 793-6.
Mackessy SP. Fractionation of Red Diamond Rattlesnake . . . , Toxicon 1985, vol. 23, pp. 337-340.
Mackessy SP. Characterization of the major metalloprotease isolated from the venom of the nothern pacific rattlesnake Crotalus Viridis Oreganus, Toxicon 1996, vol. 34, pp. 1277-1285.
Mackessy SP. Evolutionary trends in venom composition in the Western Rattlesnakes (*Crotalus viridis* sensu lato): Toxicity vs. tenderizers, Toxicon 2010, vol. 55, pp. 1463-1474.
Markland Jr. FS, Snake venom metalloproteinases, Toxicon 2013, vol. 62, pp. 3-18.
Massey DJ, et al., Venom variability and envenoming severity outcomes of the Crotalus scutulatus scutulatus . . . , J Proteomics 2012, vol. 75, pp. 2576-2587.
Moran JB, et al., Characterization of a fibrinogenase from nothern copperhead . . . , Biochim Biophys Acta 1981, vol. 659, pp. 161-168.
Mori N, et al., Biochemical Characterization of Hemorrhagic Toxins with Fibrinogenase Activity Isolated from Crotalus ruber ruber venom, Arch Biochem Biophys 1987, vol. 253, pp. 108-121.
Mori N, et al., Kallikrein-like enzyme from *Crotalus ruber ruber* (Red Rattlesnake) venom, Int J Biochem 1988, vol. 20, pp. 1425-1433.
Nielsen VG, Arkebauer MR, et al., Carbon monoxide-releasing molecule-2 decreases fibrinolysis in vitro and in vivo in the rabbit, Blood Coagul Fibrinolysis 2012, vol. 3, pp. 104-107.
Nielsen VG, Boyer LV. Iron and carbon monoxide attenuate degradation of plasmatic coagulation by Crotalus atrox venom. Blood Coagul and Fibrinolysis 2016, 27:506-510.
Nielsen VG, Ellis TC. Quantification of the effects of thrombin activatable fibrinolysis inhibitor . . . , Blood Coagul Fibrinolysis 2007, vol. 18, pp. 29-33.
Nielsen VG, et al., Fibrinogen is a heme-associated, carbon monoxide sensing molecule: a preliminary report, Blood Coagul Fibrinolysis 2011, vol. 22, pp. 443-447.
Nielsen VG, et al., Elastic modulus-based thrombelastographic quantification of plasma clot fibrinolysis with progressive plasminogen activation, Blood Coagul Fibrinolysis 2006, vol. 17, pp. 75-81.
Nielsen VG, et al., Carbon monoxide releasing molecule-2 increases the velocity of thrombus growth and strength in human plasma, Blood Coagul Fibrinolysis 2009, vol. 20, pp. 377-380.
Nielsen VG, et al., Carbon monoxide-releasing molecule-2 enhances coagulation in rabbit plasma and decreases bleeding time in clopidogrel/aspirin-treated rabbits, Blood Coagul Fibrinolysis 2011, vol. 22, pp. 756-759.
Nielsen VG, et al., Carbon monoxide-releasing molecule-2 decreases fibrinolysis in vitro and in vivo in the rabbit, Blood Coagul Fibrinolysis 2012, vol. 23, pp. 104-107.
Nielsen VG, et al., Carbon monoxide-releasing molecule-2 decreases fibrinolysis in vitro and in vivo in the rabbit, Blood Coagul Fibrinolysis 2012, vol. 23, pp. 104-725.
Nielsen VG, et al., Iron-enhanced coagulation is attenuated by chelation: a thrombelastographic and ultrastructural analysis, Blood Coagul Fibrinolysis 2014; 25:845-850.
Nielsen VG, et al., Iron and carbon monoxide enhance coagulation and attenuate fibrinolysis by different mechanisms, Blood Coagul Fibrinolysis 2014, vol. 25, pp. 695-702.
Nielsen VG, Garza JI. Comparison of the effects of CORM-2, CORM-3 and CORM-A1 on coagulation in human plasma, Blood Coagul Fibrinolysis. 2014, vol. 25 No. 8, pp. 801-805.
Nielsen VG, Kirklin JK, George JF Carbon monoxide-releasing molecule-2 decreases fibrinolysis in human plasma, Blood Coagul Fibrinolysis, Sep. 2009, vol. 20, pp. 448-455.
Nielsen VG, Pretorius E. Iron and carbon monoxide enhance coagulation and attenuate fibrinolysis by different mechanisms. Bloo Coagul Fibrinolysis, 2014, vol. 25, pp. 695-702.
Nielsen VG, Redford DT, Boyle PK. Effect of iron and carbon monoxide on fibrinogenase-like degradation of plasmatic coagulation by venoms of four *Crotalus* species. Blood Coagul Fibrinolysis. vol. 28, issue 1, 2017, pp. 34-39.
O'Neil ME, et al., Snakebite Injuries Treated in the United States Emergency Departments, 2011-2004, Wilderness Environ Med 2007, vol. 18, pp. 281-287.
Orino K. Functional binding analysis of human fibrinogen as an iron- and heme-binding protein, Biometals, 2013, vol. 26, pp. 789-794.
Rael ED, et al., Isolation of a Fibrinolytic Protease, M4, from Venom of *Crotalus molossus molossus* (Northern Blacktail Rattlesnake), Haemostasis, 1992, vol. 22, pp. 41-49.
Ruha AM, et al., Recombinant Factor VIIa for Treatment of Gastrointestinal Hemorrhage Following Rattlesnake Envenomation, Wilderness Environ Med 2009, vol. 20, pp. 156-160.
Salazar AM, et al., Venom variation in hemostatis of the southern Pacific rattlesnake (*Crotalus oreganus helleri*): Isolation of hellerase, Comp Biochem Physiol C Toxicol Pharmacol 2009, vol. 149, pp. 307-316.
Seifert SA1, et al., AAPCC database characterization of native U.S. venomous snake exposures, 2001-2005, Clin Toxicol (Phila) 2009, vol. 47, pp. 327-335.
Shimizu A1, et al., Venom from southern copperhead snake (*Agkistrodon contortrix contortrix*) . . . , Toxicon 1987, vol. 25, pp. 751-757.
Shu YY, et al., A thrombin-like enzyme from timber rattlesnake venom, Biochim Biophys Acta 1983, vol. 748, pp. 236-244.
Spiller HA, et al., Use of antivenom for snakebites reported to United States poison centers, Am J Emerg Med 2010, vol. 28, pp. 780-785.
Sunagar K, et al., Intraspecific venom variation in the medically significant Southern Pacific Rattlesnake (*Crotalus oreganus helleri*): Biodiscovery, clinical and evolutionary implications, J Proteomics 2014, vol. 99, pp. 68-83.

(56) References Cited

OTHER PUBLICATIONS

Svoboda P1, et al., Purification and characterization of three alpha2-antiplasmin and alpha2-macroglobulin . . . , Toxicon 1995, vol. 33, pp. 1331-1346.

Toschlog EA, et al., Surgical Considerations in the Management of Pit Viper Snake Envenomation, J Am Coll Surg 2013, vol. 217, pp. 726-735.

Tu AT, et al., Biochemical Characterization of atroxase and nucleotide sequence encoding the fibrinolytic enzyme, Toxicon 1996, vol. 34, pp. 1295-1300.

Van Mierop LH, et al., Difibrination Syndrom Following Bites by th Eastern Diamondback Rattlesnake, J Fla Med Assoc 1980, vol. 67, pp. 21-27.

Walker JP, Morrison RL. Current Management of Copperhead Snakebite, J Am Coll Surg 2011, vol. 212, pp. 470-474.

Walter FG, et al., Epidemiology of severe and fatal rattlesnake bites published in the American Association of Poison Control Centers' Annual Reports, Clin Toxicol (Phila) 2009, vol. 47, pp. 663-669.

Walter FG, et al., Epidemiology of the Reported Severity of Copperhead (*Agkistrodon contortrix*) Snakebite, South Med J. 2012, vol. 105 No. 6, pp. 313-320.

Walter FG, et al., Epidemiology of the Reported Severity of Cottonmouth (*Agkistrodon piscivorus*) Snakebite, South Med J. 2014, vol. 107 No. 3, pp. 150-156.

Willis TW, Tu AT. Purification and Biochemical Characterization of Atroxase, a Nonhemorrhagic . . . , Biochemistry 1988, vol. 27, pp. 4769-4777.

Willis TW1, et al., Thrombolysis with a snake venom protease in a rat model of venous thrombosis, Thromb Res 1989, vol. 53, pp. 19-29.

Zad O, et al., Shock, respiratory failure, and coagulopathy after an intravenouse copperhead envenomation, Am J Emerg Med 2009, vol. 27, 377.e1-377.e5.

\* cited by examiner

COMPOSITIONS AND METHODS FOR TREATING AND PREVENTING VENOM RELATED POISONING

CROSS REFERENCE TO RELATED APPLICATIONS

This application is a Section 371 U.S. national stage entry of International Patent Application No. PCT/US2016/033542, International Filing Date May 20, 2016, which claims the benefit of U.S. Provisional Application Ser. No. 62/164,916, filed May 21, 2015, which are incorporated herein by reference in their entireties.

FIELD OF THE INVENTION

This invention relates to compositions and methods for treating, ameliorating and preventing the toxic effects of venom poisoning. In particular, the invention provides compositions comprising carbon monoxide releasing molecules (CORM) or compositions comprising CORM and iron releasing molecules (IRM) for one or more of enhancing coagulation, reducing fibrinolysis, and/or inactivating venom related metalloproteinase activity in a subject suffering from or at risk of suffering from venom poisoning.

INTRODUCTION

In the Animal kingdom, a number of venomous animals, such as snakes, produce venom that is harmful to humans, and to their pets and livestock. For humans alone, approximately one million people throughout the world are bitten each year by venomous (poisonous) snakes. It has been estimated that of these some 100,000 die and that another 300,000 will suffer some form of disability for the remainder of their lives.

Improved methods for treating, ameliorating and preventing the toxic effects of venom poisoning are needed.

SUMMARY OF THE INVENTION

Experiments conducted during the course of developing embodiments for the present invention demonstrated that iron and carbon monoxide attenuate degradation of plasmatic coagulation by *Crotalus atrox* venom. It has been determined that iron and carbon monoxide (CO) enhance fibrinogen as a thrombin substrate, likely secondary to conformational changes in molecular structure. Such experiments tested the hypothesis that pretreatment of plasma with iron and CO could attenuate the effects of exposure to *Crotalus Atrox* venom. Human plasma was exposed to 0-10 µM ferric chloride (iron source) and 0-100 µM carbon monoxide releasing molecule-2 (CO source) followed by exposure to 0-0.5 µg/ml venom for 5 to 20 min. Changes in coagulation kinetics were determined with thrombelastography. Iron and CO significantly attenuated venom mediated degradation of plasmatic coagulation in terms of onset time, velocity of clot growth and final clot strength.

Experiments conducted during the course of developing embodiments for the present invention demonstrated that iron and carbon monoxide attenuate *Crotalus atrox* venom-enhanced tissue-type plasminogen activator initiated fibrinolysis. In addition to degrading fibrinogen as a source of consumptive coagulopathy, rattlesnake venom has also been demonstrated to enhance fibrinolysis and degrade alpha-2-antiplasmin. The goals of these experiments was to characterize the kinetic fibrinolytic profile of *Crotalus atrox* venom in the absence and presence of tissue-type plasminogen activator (tPA), and to also ascertain if iron and carbon monoxide (CO, a positive modulator of alpha-2-antiplasmin) could attenuate venom-enhanced fibrinolysis. Utilizing thrombelastographic methods, the coagulation and fibrinolytic kinetic profiles of human plasma exposed to *Crotalus atrox* venom (0-2 µg/ml) were determined in the absence or presence of tPA (0-100 IU/ml). Then, either separately or in combination, plasma was exposed to iron (ferric chloride, 10 µM) or CO (carbon monoxide releasing molecule-2, 100 µM) prior to incubation with venom; the plasma sample was subsequently subjected to thrombelastographic analysis with addition of tPA. Venom exposure in the absence of tPA did not result in detectable fibrinolysis. In the presence of tPA, venom markedly enhanced fibrinolysis. Iron and CO, markedly attenuated venom enhancement of fibrinolysis. *Crotalus atrox* venom enhances tPA mediated fibrinolysis, and interventions that enhance/protect alpha-2-antiplasmin activity significantly attenuate venom enhanced fibrinolysis.

Experiments conducted during the course of developing embodiments for the present invention demonstrated the effect of iron and carbon monoxide on fibrinogenase-like degradation of plasmatic coagulation by venoms of six *Agkistrodon* species. As noted, annually thousands suffer poisonous snake bite, often from defibrinogenating species. It has been demonstrated that iron and carbon monoxide change the ultrastructure of plasma thrombi and improve coagulation kinetics. Thus, these experiments sought to determine if pretreatment of plasma with iron and carbon monoxide could attenuate venom mediated catalysis of fibrinogen obtained from *Agkistrodon* species with fibrinogenase activity. Human plasma was pretreated with ferric chloride (0-10 µM) and carbon monoxide releasing molecule-2 (CORM-2, 0-100 µM) prior to exposure to 0.5-11 µg/ml of six different *Agkistrodon* species' venom. The amount of venom used for experimentation needed to decrease coagulation function of one or more kinetic parameters by at least 50% of normal values for (e.g., half the normal speed of clot formation). Coagulation kinetics were determined with thrombelastography. All six snake venoms degraded plasmatic coagulation kinetics to a significant extent, especially prolonging the onset to clot formation and diminishing the speed of clot growth. Pretreatment of plasma with iron and carbon monoxide attenuated these venom mediated coagulation kinetic changes in a species-specific manner, with some venom effects markedly abrogated while others were only mildly decreased.

Experiments conducted during the course of developing embodiments for the present invention demonstrated that iron and carbon monoxide prevent degradation of plasmatic coagulation by thrombin-like activity in rattlesnake venom. Three rattlesnake species in particular, the timber rattlesnake, Eastern diamondback rattlesnake and Southern Pacific rattlesnake, cause clinically relevant hypofibrinogenemia via thrombin-like activity in their venom. It has been demonstrated that iron and carbon monoxide change the ultrastructure of plasma thrombi and improve coagulation kinetics. Thus, these examples sought to determine if pretreatment of plasma with iron and carbon monoxide could attenuate venom mediated catalysis of fibrinogen via thrombin-like activity. Human plasma was pretreated with ferric chloride (0-10 µM) and carbon monoxide releasing molecule-2 (CORM-2, 0-100 µM) prior to exposure to 2.5-10 µg/ml of venom obtained from the aforementioned three species of rattlesnake. Coagulation kinetics were determined with thrombelastography. All three snake venoms degraded plasmatic coagulation kinetics to a significant extent, especially diminishing the speed of clot growth and strength. Pretreatment of plasma with iron and carbon monoxide completely abrogated the effects of all three venoms on coagulation kinetics.

Experiments conducted during the course of developing embodiments for the present invention demonstrated the effect of iron and carbon monoxide on fibrinogenase-like degradation of plasmatic coagulation by venoms of four *Crotalus* species. Iron and carbon monoxide improve coagulation kinetics by modulation of fibrinogen as demonstrated in various *Agkistrodon* species and *Crotalus atrox*. Thus, experiments were conducted to determine if pretreatment of plasma with iron and carbon monoxide could attenuate venom mediated catalysis of fibrinogen obtained from four common *Crotalus* species with known fibrinogenase activity. Human plasma was pretreated with ferric chloride (0-10 μM) and carbon monoxide releasing molecule-2 (0-100 μM) prior to exposure to venom from a Northern Pacific rattlesnake, Arizona black rattlesnake, prairie rattlesnake, or red diamond rattlesnake. The concentration of venom used decreased coagulation function of one or more kinetic parameters by at least 50% of normal values. Coagulation kinetics were determined with thrombelastography. Three snake venoms significantly degraded plasmatic coagulation kinetics, prolonging the onset to clot formation, diminishing velocity of clot growth and decreasing clot strength. However, red diamond rattlesnake venom exposure resulted in mixed coagulation kinetics, significantly decreasing the time to onset of coagulation without decreasing the velocity of clot growth. Iron and carbon monoxide attenuated these coagulation kinetic changes in a species-specific manner.

Experiments conducted during the course of developing embodiments for the present invention demonstrated the effects of iron and carbon monoxide on the fibrinogenolytic activity of *Crotalus atrox* venom. Plasmatic coagulation after pre-exposure to iron and carbon monoxide (CO) is resistant to the fibrinogenolytic effects of *Crotalus* species venom. However, the direct effects of iron/CO on venom activity are unknown. Thus, the hypothesis that pretreatment of *Crotalus atrox* venom with iron/CO could attenuate its fibrinogenolytic activity was tested. *C. atrox* venom (0-0.2 mg/ml) was exposed to 0-10 μM FeCl₃ and/or 0-100 μM carbon monoxide releasing molecule-2 (CORM-2), or inactivated CORM-2 (iCORM-2) for 3 min at room temperature. Venom solution (0-2 μg/ml final concentration) was then placed in citrated human plasma containing tissue factor, followed by CaCl₂ addition for commencement of coagulation. Data were determined with thrombelastography for 15 min at 37° C. Samples exposed to venom alone demonstrated a complete suppression of coagulation. Exposure of venom to iron/CO eliminated venom effects on coagulation. Iron addition did not affect venom mediated elimination of coagulation; however, exposure to CORM-2 alone resulted in loss of venom activity. Lastly, iCORM-2 did not affect the fibrinogenolytic effects of venom. CO completely suppressed venom activity, with iron not affecting venom activity or interfering with CO mediated venom inhibition.

Accordingly, the present invention relates to compositions and methods for treating, ameliorating and preventing the toxic effects of venom poisoning. In particular, the invention provides compositions comprising carbon monoxide releasing molecules (CORM) or compositions comprising CORM and iron releasing molecules (IRM) for one or more of enhancing coagulation, reducing fibrinolysis, and/or inactivating venom related metalloproteinase activity in a subject suffering from or at risk of suffering from venom poisoning.

In certain embodiments, the present invention provides compositions comprising a carbon monoxide releasing molecule (CORM), wherein in vitro or in vivo exposure of the composition to a biological sample results in release of carbon monoxide from the CORM. In such embodiments, the CORM is selected from the group consisting of tricarbonyldichlororuthenium (II) dimer, tricarbonylchloro(glycinato)ruthenium (II), sodium boranocarbonate, dimanganese decacarbonyl, and iron pentacarbonyl.

In some embodiments, the composition is a pharmaceutical composition.

In some embodiments, the composition comprises between about 25 μM to about 200 μM of the CORM. In some embodiments, the composition comprises between about 350-1000 mg of the CORM. In some embodiments, the amounts of CORM within the composition is such that upon administration to a subject (e.g., a human subject), the composition is able to treat, ameliorate and/or prevent the toxic effects of venom poisoning.

In some embodiments, the amount of CORM within the composition is such that upon administration to a subject (e.g., a human subject), the composition is able to prevent one or more of venom mediated catalysis of fibrinogen in the subject, venom mediated degradation of plasma coagulation in the subject, venom mediated coagulopathy in the subject, and venom mediated catalysis and inactivation of fibrinogen.

In some embodiments, the amount of CORM within the composition is such that upon administration to a subject (e.g., a human subject), the composition is able to inactivate snake venom related metalloproteinase activity (e.g., $Zn^{+2}$ metalloproteinase activity (e.g., Catroxase-2)). In some embodiments, such inactivation results in prevention and/or alleviation of pain and neurological effects related to snake venom related metalloproteinase activity (e.g., $Zn^{+2}$ metalloproteinase activity).

In certain embodiments, the present invention provides compositions comprising a CORM and an iron releasing molecule (IRM), wherein in vitro or in vivo exposure of the composition to a biological sample results in release of carbon monoxide from the CORM and release of iron from the IRM. In some embodiments, the composition is a pharmaceutical composition. In such embodiments, the CORM is selected from the group consisting of tricarbonyldichlororuthenium (II) dimer, tricarbonylchloro(glycinato) ruthenium (II), sodium boranocarbonate, dimanganese decacarbonyl, and iron pentacarbonyl. In such embodiments, the IRM is selected from the group consisting of ferric chloride, iron dextran, ferric gluconate, iron sucrose, ferumoxytol, ferric carboxymaltose, and iron isomaltoside.

In some embodiments, the composition is a pharmaceutical composition.

In some embodiments, the composition comprises between about 25 μM to about 200 μM of the CORM. In some embodiments, the composition comprises between about 350-1000 mg of the CORM. In some embodiments, the composition comprises between 5-25 mg of the IRM. In some embodiments, the amounts of CORM and IRM within the composition is such that upon administration to a subject (e.g., a human subject), the composition is able to treat, ameliorate and/or prevent the toxic effects of venom poisoning.

In some embodiments, the amount of CORM and IRM within the composition is such that upon administration to a subject (e.g., a human subject), the composition is able to prevent one or more of venom mediated catalysis of fibrinogen in the subject, venom mediated degradation of plasma coagulation in the subject, venom mediated coagulopathy in the subject, and venom mediated catalysis and inactivation of fibrinogen.

In some embodiments, the amount of CORM within the composition is such that upon administration to a subject (e.g., a human subject), the composition is able to inactivate snake venom related metalloproteinase activity (e.g., $Zn^{+2}$ metalloproteinase activity (e.g., Catroxase-2)). In some embodiments, such inactivation results in prevention and/or alleviation of pain and neurological effects related to snake venom related metalloproteinase activity (e.g., $Zn^{+2}$ metalloproteinase activity (e.g., Catroxase-2)).

In certain embodiments, the present invention provides methods of enhancing coagulation or reducing fibrinolysis in a subject suffering from or at risk of suffering from venom poisoning, comprising administering to the subject either a composition comprising a CORM as described herein, or a composition comprising a CORM and an IRM as described herein, wherein the administering results in prevention of one or more of venom mediated catalysis of fibrinogen in the subject, venom mediated degradation of plasma coagulation in the subject, venom mediated coagulopathy in the subject, and venom mediated catalysis and inactivation of fibrinogen.

In some embodiments, the released carbon monoxide from either composition interacts with fibrinogen in the subject which results in enhancement of fibrinogen as a thrombin substrate.

In some embodiments, the released carbon monoxide from either composition interacts with snake venom associated metalloproteinases (e.g., $Zn^{+2}$ metalloproteinases), wherein the interaction results in inactivation of the snake venom associated metalloproteinase. In some embodiments, such inactivation results in prevention and/or alleviation of pain and neurological effects related to snake venom related metalloproteinase activity (e.g., $Zn^{+2}$ metalloproteinase activity).

In certain embodiments, the present invention provides methods for inactivating venom related metalloproteinase activity in a subject suffering from venom poisoning, comprising administering to the subject either a composition comprising a CORM as described herein, or a composition comprising a CORM and an IRM as described herein, wherein the released carbon monoxide interacts with snake venom associated metalloproteinases, wherein the interaction results in inactivation of the snake venom associated metalloproteinases. In some embodiments, the snake venom associated metalloproteinase is a $Zn^{+2}$ metalloproteinase.

The methods are not limited to a particular type of venom. In some embodiments, the venom is Crotalus related venom. For example, in some embodiments, the Crotalus related venom is a venom from a Crotalus species selected from C. adamanteus, C. aquilus, C. atrox, C. basilicus, C. cerastes, C. durissus, C. enyo, C. horridus, C. intermedius, C. lannomi, C. lepidus, C. mitchellii, C. molossus, C. oreganus, C. polystictus, C. pricei, C. pusillus, C. ruber, C. scutulatus, C. simus, C. stejnegeri, C. tigris, C. tortugensis, C. totonacus, C. transversus, C. triseriatus, C. viridis, and C. willardi. In some embodiments, the venom is from one of the following: Naja naja (Indian cobra), Bothrops asper (Fur-de-lance), Agkistrodon piscivorus piscivorus, Agkistrodon contortrix contortrix, Agkistrodon contortrix laticinctus, Askistrodon contortix pictigaster, Agkistrodon piscivorus leucostoma, Agkistrodon contortrix mokasen, Northern Pacific rattlesnake, Arizona Black rattlesnake, Prairie rattlesnake, Red Diamond rattlesnake, Timber rattlesnake, Eastern Diamondback rattlesnake, and Southern Pacific rattlesnake.

In some embodiments, either of the compositions is formulated for administration by an aerosol spray, an ointment, a bandage, a surgical dressing, a wound packing, a patch, autoinjector, a swab, a liquid, a paste, a cream, a lotion, a foam, a gel, an emulsion, a powder, or a needle.

In some embodiments, either of the compositions is co-administered with a hemostatic agent, a coagulant, an anti-fibrinolytic medication, a blood coagulation factor, fibrin, thrombin, recombinant activated factor VII, prothrombin complex concentrate, FEIBA, or a therapeutic agent selected from the group consisting of an antibiotic, an anesthetic, an analgesic, an antihistamine, an antimicrobial, an antifungal, an antiviral, and an anti-inflammatory agent. In some embodiments, the blood coagulation factor is factor VIII, factor IX, factor XIII, or von Willebrand's factor.

In some embodiments, either of the compositions is co-administered with antivenom against Crotalus venom. Such embodiments are not limited to particular type of antivenom. In some embodiments, the antivenom is Crotalidae Polyvalent Immune Fab Ovine (CroFab) or Crotalinae Equine Immune F(ab)2 Antivenom (Anavip).

In some embodiments, the treated subject is a living mammal (e.g., a living human).

In certain embodiments, the present invention provides methods for inactivating venom related metalloproteinase activity in a subject suffering from venom poisoning, comprising administering to the subject either a composition comprising a CORM as described herein, or a composition comprising a CORM and an IRM as described herein, wherein the released carbon monoxide interacts with snake venom associated metalloproteinases, wherein the interaction results in inactivation of the snake venom associated metalloproteinases. In some embodiments, the snake venom associated metalloproteinase is a $Zn^{+2}$ metalloproteinase.

The methods are not limited to a particular type of venom. In some embodiments, the venom is Crotalus related venom. For example, in some embodiments, the Crotalus related venom is a venom from a Crotalus species selected from C. adamanteus, C. aquilus, C. atrox, C. basilicus, C. cerastes, C. durissus, C. enyo, C. horridus, C. intermedius, C. lannomi, C. lepidus, C. mitchellii, C. molossus, C. oreganus, C. polystictus, C. pricei, C. pusillus, C. ruber, C. scutulatus, C. simus, C. stejnegeri, C. tigris, C. tortugensis, C. totonacus, C. transversus, C. triseriatus, C. viridis, and C. willardi. In some embodiments, the venom is from one of the following: Naja naja (Indian cobra), Bothrops asper (Fur-de-lance), Agkistrodon piscivorus piscivorus, Agkistrodon contortrix contortrix, Agkistrodon contortrix laticinctus, Askistrodon contortix pictigaster, Agkistrodon piscivorus leucostoma, Agkistrodon contortrix mokasen, Northern Pacific rattlesnake, Arizona Black rattlesnake, Prairie rattlesnake, Red Diamond rattlesnake, Timber rattlesnake, Eastern Diamondback rattlesnake, and Southern Pacific rattlesnake.

In some embodiments, either of the compositions is formulated for administration by an aerosol spray, an ointment, a bandage, a surgical dressing, a wound packing, a patch, autoinjector, a swab, a liquid, a paste, a cream, a lotion, a foam, a gel, an emulsion, a powder, or a needle.

In some embodiments, either of the compositions is co-administered with a hemostatic agent, a coagulant, an anti-fibrinolytic medication, a blood coagulation factor, fibrin, thrombin, recombinant activated factor VII, prothrombin complex concentrate, FEIBA, or a therapeutic agent selected from the group consisting of an antibiotic, an anesthetic, an analgesic, an antihistamine, an antimicrobial, an antifungal, an antiviral, and an anti-inflammatory agent.

In some embodiments, the blood coagulation factor is factor VIII, factor IX, factor XIII, or von Willebrand's factor.

In some embodiments, either of the compositions is co-administered with antivenom against *Crotalus* venom. Such embodiments are not limited to particular type of antivenom. In some embodiments, the antivenom is Crotalidae Polyvalent Immune Fab Ovine (CroFab) or Crotalinae Equine Immune F(ab)2 Antivenom (Anavip).

In some embodiments, the treated subject is a living mammal (e.g., a living human).

In certain embodiments, the present invention provides kits comprising either a composition comprising a CORM as described herein, or a composition comprising a CORM and an IRM as described herein, an antivenom composition, and instructions for administering the composition to a living mammal. In some embodiments, the kits further comprise one or more of a hemostatic agent, a coagulant, an anti-fibrinolytic medication, a blood coagulation factor, fibrin, thrombin, recombinant activated factor VII, prothrombin complex concentrate, FEIBA, or a therapeutic agent selected from the group consisting of an antibiotic, an anesthetic, an analgesic, an antihistamine, an antimicrobial, an antifungal, an antiviral, and an anti-inflammatory agent.

Figure 12:
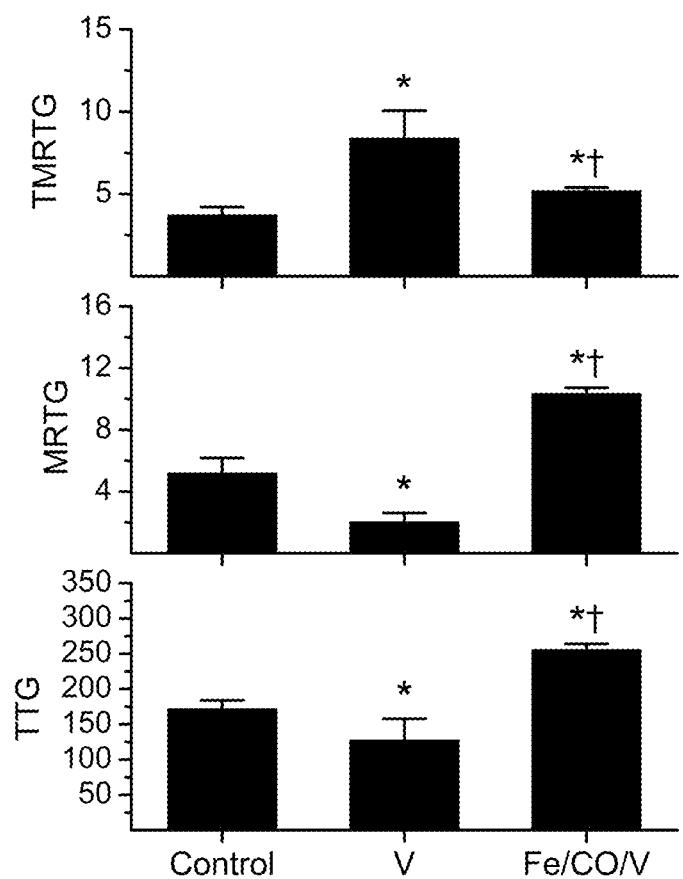

FIG. 12: Effect of *Agkistrodon piscivorus piscivorus* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=venom added, 5 min incubation prior to calcium addition; Fe/CO/V=plasma exposed to ferric chloride and CORM-2 prior to 5 min incubation with venom before calcium addition. *P<0.05 vs. Control; †P<0.05 vs. V.

Figure 13:
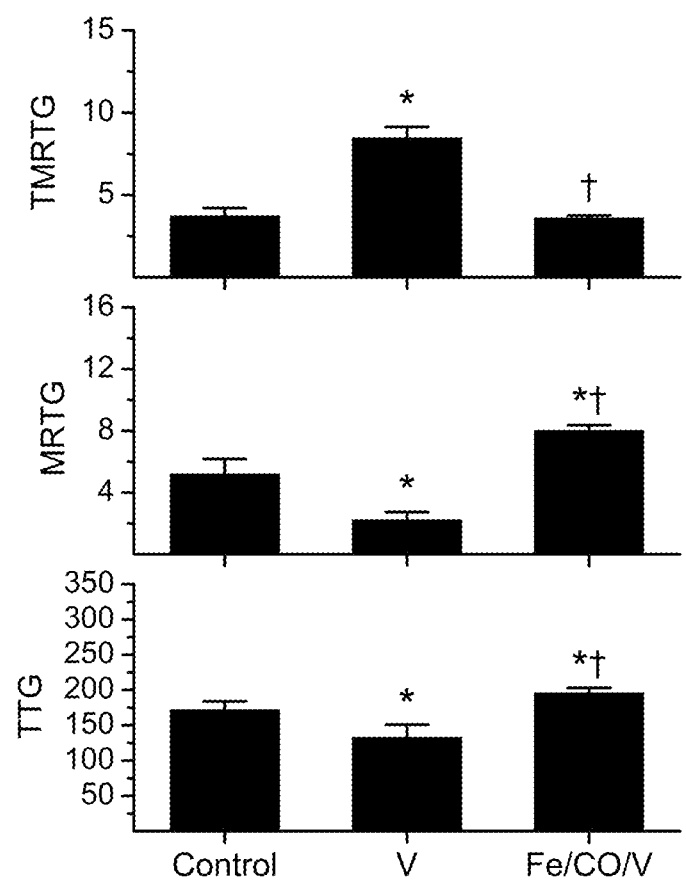

FIG. 13: Effect of *Agkistrodon piscivorus leucostoma* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=venom added, 5 min incubation prior to calcium addition; Fe/CO/V=plasma exposed to ferric chloride and CORM-2 prior to 5 min incubation with venom before calcium addition. *P<0.05 vs. Control; †P<0.05 vs. V.

Figure 14:
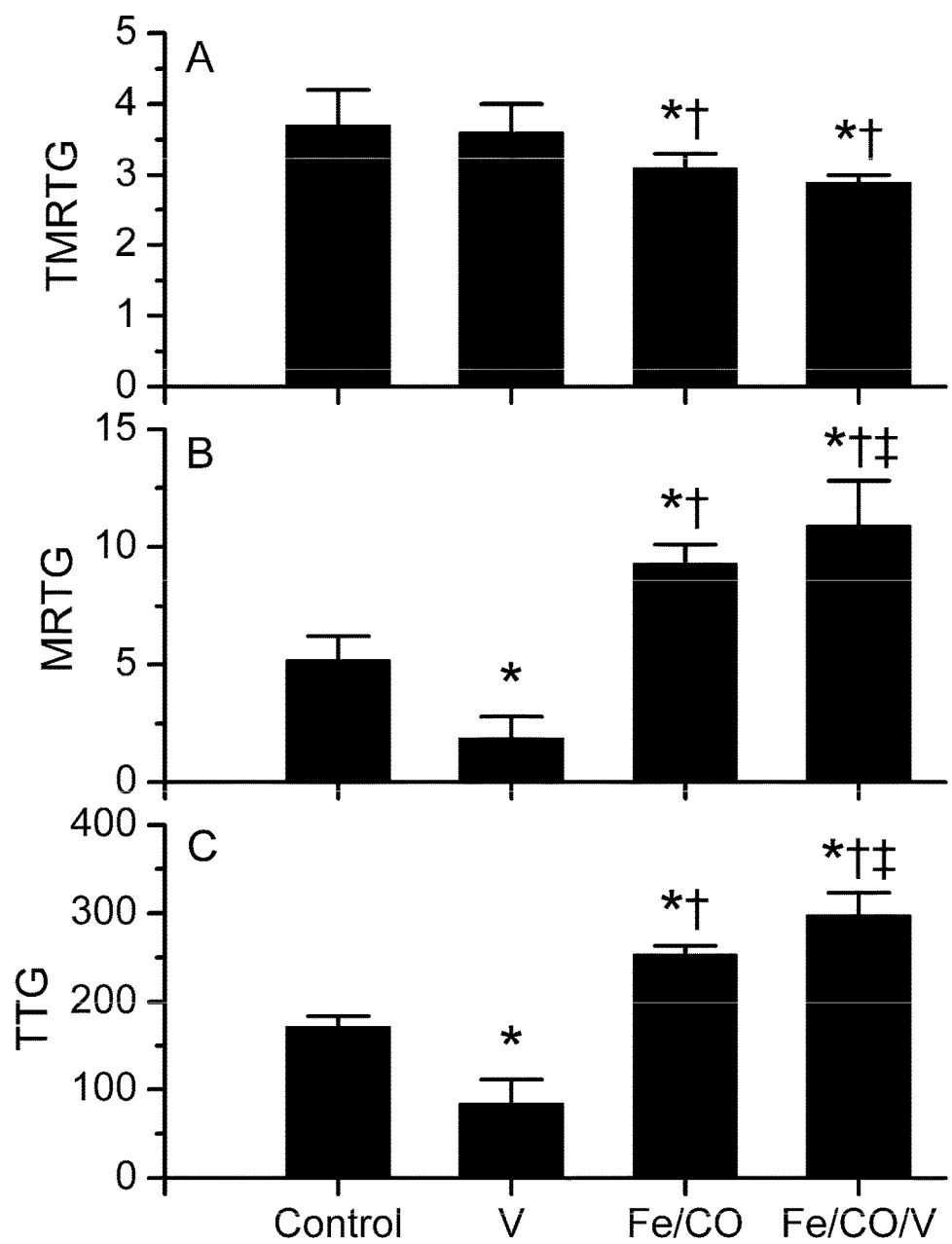

FIG. 14: Effect of timber rattlesnake venom, iron and carbon monoxide exposure on coagulation in human plasma. Data are presented as mean±SD. Panel A: TMRTG=time to maximum rate of thrombus generation (min); Panel B: MRTG=maximum rate of thrombus formation (dynes/cm$^2$/sec); Panel C: TTG=total thrombus generation (dynes/cm$^2$); Control=additive naïve plasma; V=2.5 µg/ml venom added, 5 min incubation prior to calcium addition; Fe/CO=10 µM ferric chloride and 100 µM CORM-2 addition and 5 min incubation prior to calcium addition; Fe/CO/V=plasma exposed to ferric chloride and CORM-2 prior to 5 min incubation with venom before calcium addition. *P<0.05 vs. Control; †P<0.05 vs. V; ‡P<0.05 vs. Fe/CO.

Figure 15:
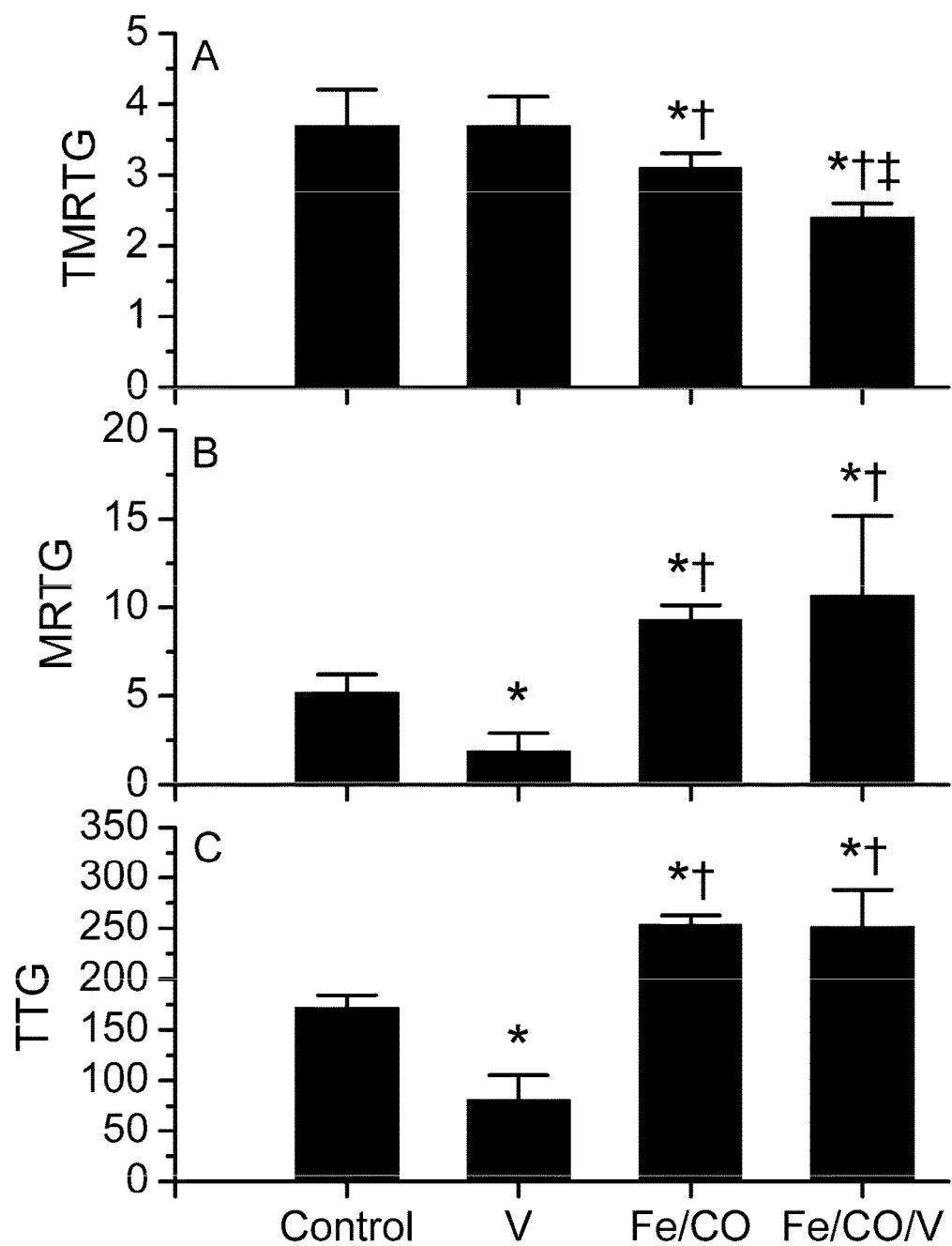

FIG. 15: Effect of Eastern diamondback rattlesnake venom, iron and carbon monoxide exposure on coagulation in human plasma. Data are presented as mean±SD. Panel A: TMRTG=time to maximum rate of thrombus generation (min); Panel B: MRTG=maximum rate of thrombus formation (dynes/cm$^2$/sec); Panel C: TTG=total thrombus generation (dynes/cm$^2$); Control=additive naïve plasma; V=2.5 µg/ml venom added, 5 min incubation prior to calcium addition; Fe/CO=10 µM ferric chloride and 100 µM CORM-2 addition and 5 min incubation prior to calcium addition; Fe/CO/V=plasma exposed to ferric chloride and CORM-2 prior to 5 min incubation with venom before calcium addition. *P<0.05 vs. Control; †P<0.05 vs. V; ‡P<0.05 vs. Fe/CO.

Figure 16:
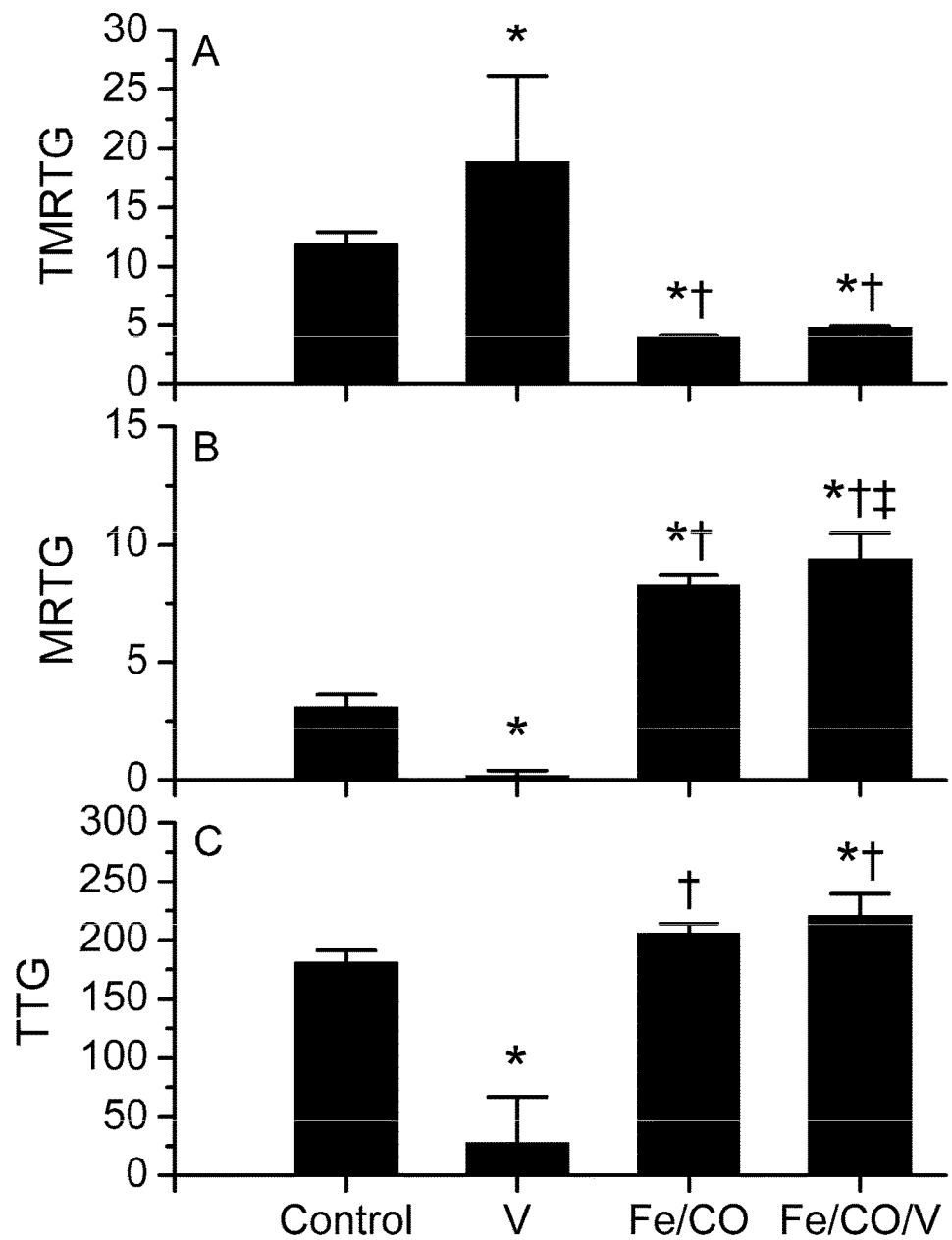

FIG. 16: Effect of Southern Pacific rattlesnake venom, iron and carbon monoxide exposure on coagulation in human plasma. Data are presented as mean±SD. Panel A: TMRTG=time to maximum rate of thrombus generation (min); Panel B: MRTG=maximum rate of thrombus formation (dynes/cm$^2$/sec); Panel C: TTG=total thrombus generation (dynes/cm$^2$); Control=additive naïve plasma; V=10 µg/ml venom added, just prior to calcium addition; Fe/CO=10 µM ferric chloride and 100 µM CORM-2 addition; Fe/CO/V=plasma exposed to ferric chloride and CORM-2 prior to addition of venom and calcium. *P<0.05 vs. Control; †P<0.05 vs. V; ‡P<0.05 vs. Fe/CO.

Figure 17:
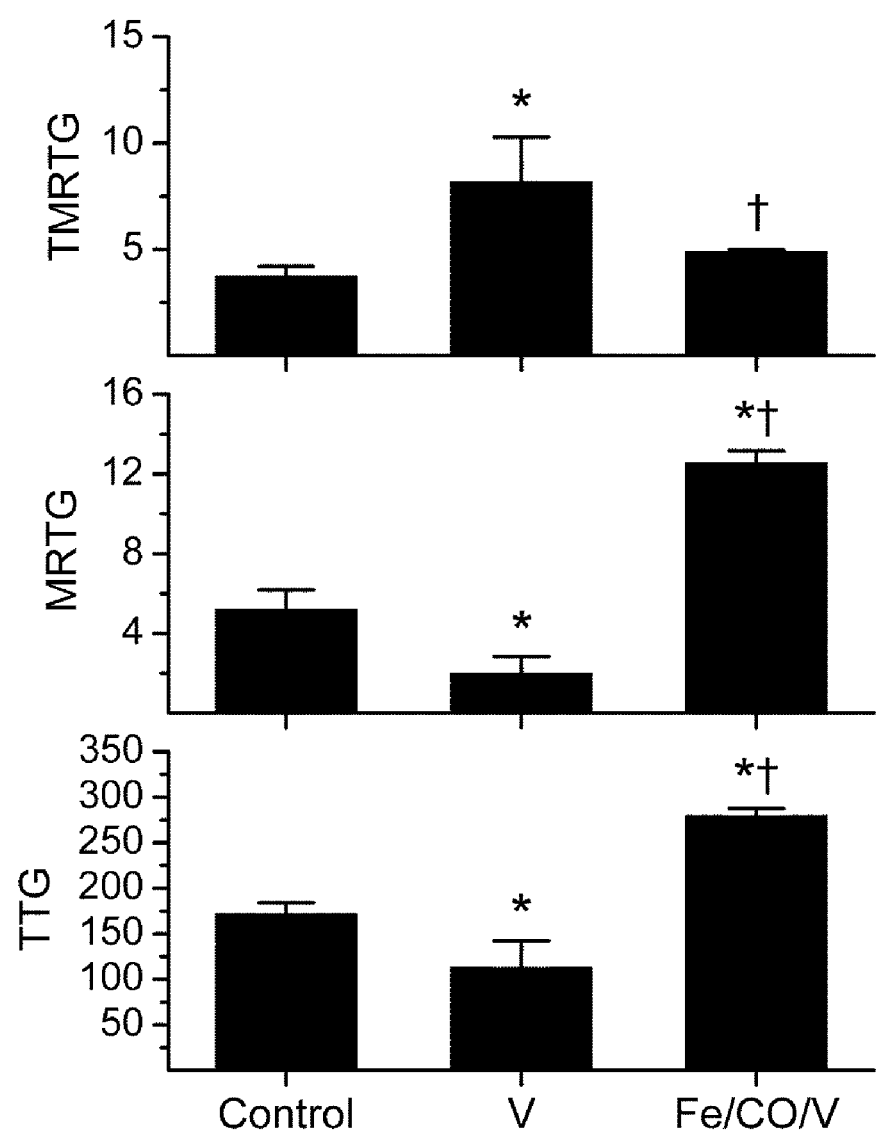

FIG. 17: Effect of *Crotalus oreganus oreganus* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=1 µg/ml venom added, 5 min incubation prior to calcium addition; Fe/CO/V=plasma exposed to ferric chloride and CORM-2 prior to addition of venom and calcium. *P<0.05 vs. Control; †P<0.05 vs. V.

Figure 18:
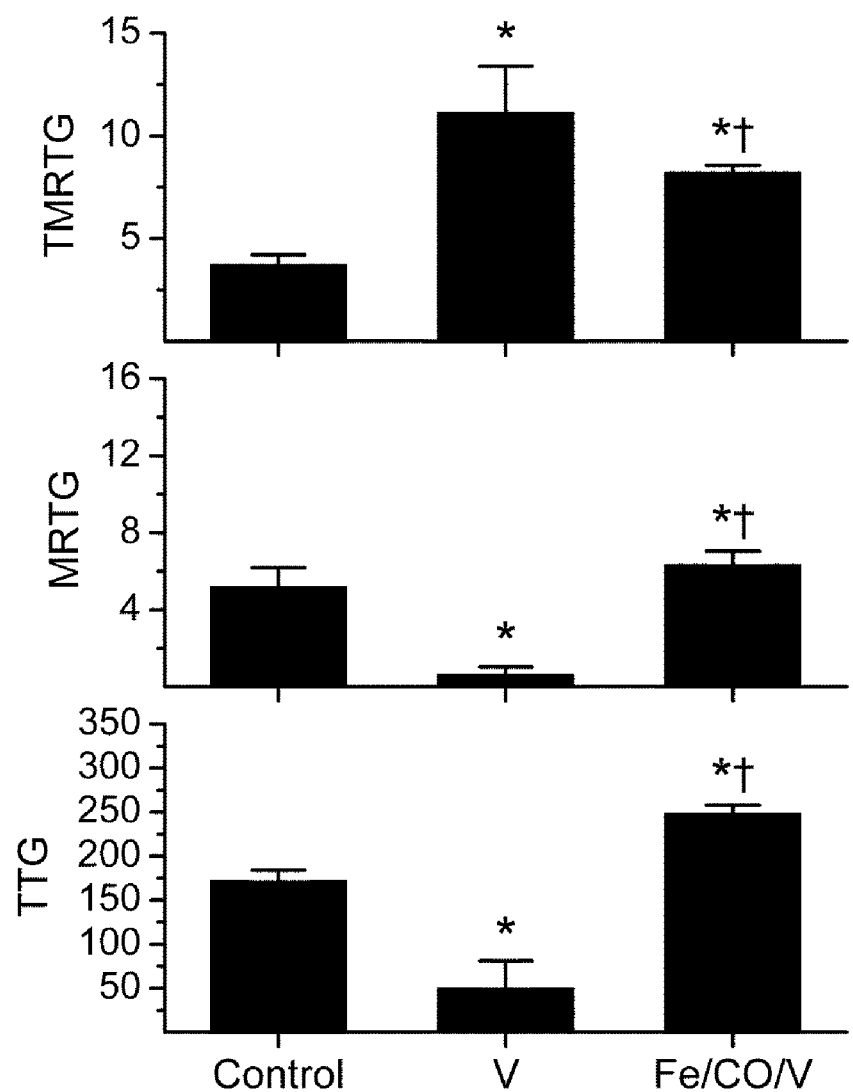

FIG. 18: Effect of *Crotalus oreganus cerberus* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=2 µg/ml venom added, 5 min incubation prior to calcium addition; Fe/CO/V=plasma exposed to ferric chloride and CORM-2 prior to addition of venom and calcium. *P<0.05 vs. Control; †P<0.05 vs. V.

Figure 19:
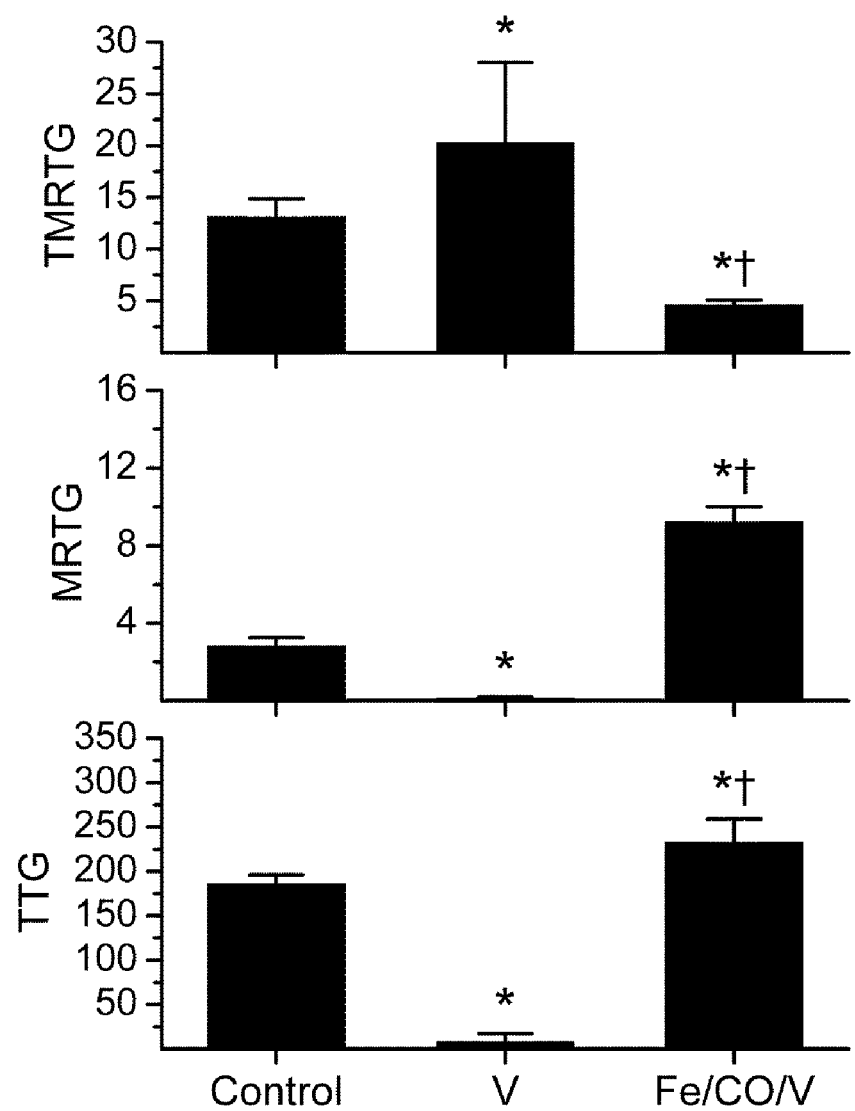

FIG. 19: Effect of *Crotalus viridis viridis* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=10 µg/ml venom added, just prior to calcium addition; Fe/CO/V=plasma exposed to ferric chloride and CORM-2 prior to addition of venom and calcium. *P<0.05 vs. Control; †P<0.05 vs. V.

Figure 20:
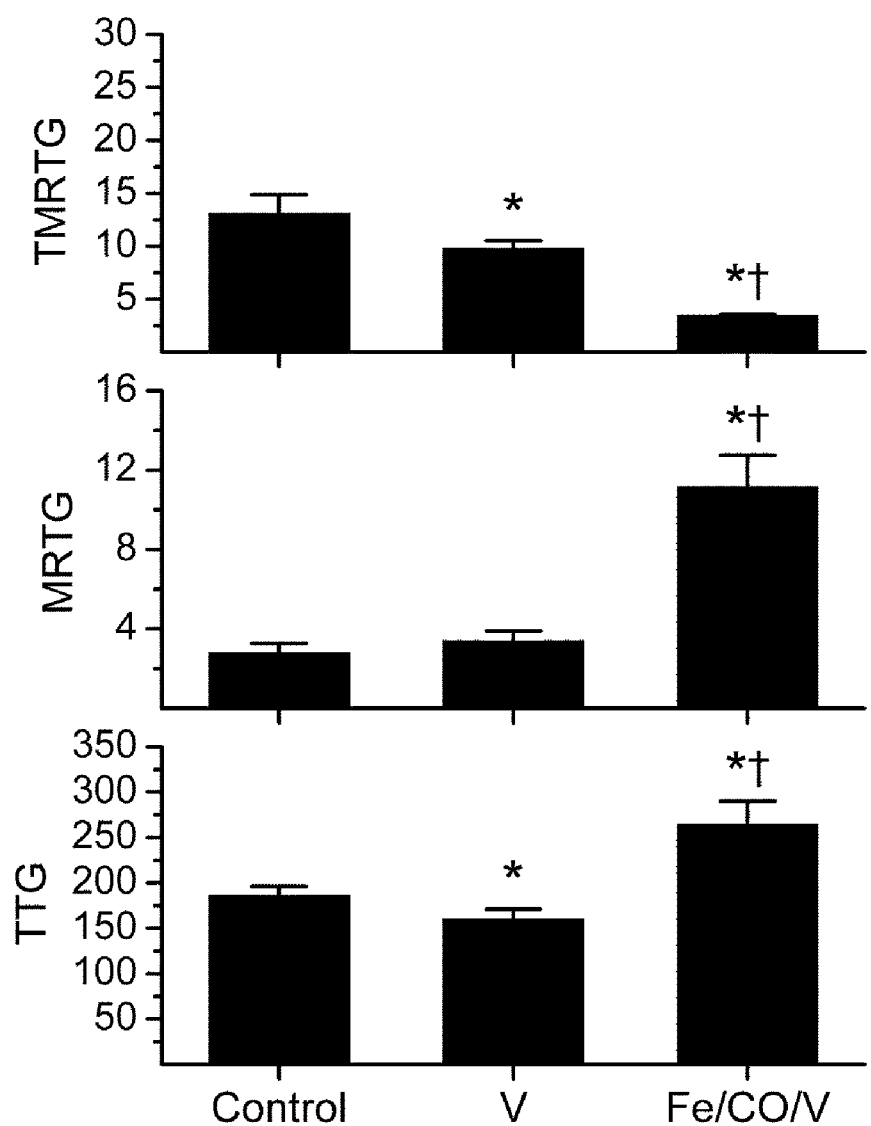

FIG. 20: Effect of *Crotalus ruber ruber* venom, iron and carbon monoxide exposure on coagulation in human plasma. Data are presented as mean+SD. TMRTG=time to maximum rate of thrombus generation (min); MRTG=maximum rate of thrombus formation (dynes/cm$^2$/sec); TTG=total thrombus generation (dynes/cm$^2$); Control=additive naïve plasma; V=10 µg/ml venom added, just prior to calcium addition; Fe/CO/V=plasma exposed to ferric chloride and CORM-2 prior to addition of venom and calcium. *P<0.05 vs. Control; †P<0.05 vs. V.

DEFINITIONS

The term "venom" is intended to encompass any poisonous substance which is parenterally transmitted, that is subcutaneously or intramuscularly transmitted, by the bite or sting of a venomous animal into a mammal and which contains various toxins such as, but not limited to, hemotoxins, hemagglutinins, neurotoxins, leukotoxins, and endotheliatoxins.

The term "venomous animals" is taken to mean venomous members of the Animal kingdom, as are well known in the art. Non-limiting examples of venomous animals whose bite or sting transmit venom to a mammal victim include reptiles such as snakes. Non-limiting examples of venomous snakes include, but are not limited to, *Agkistrodon* spp., *Bothrops* spp., *Crotalus* spp., *Trimeresurus* spp., *Lachesis mutus*, *Sistrurus* spp., *Bitis* spp., *Causus* spp., *Cerastes* spp., *Echis carinatus*, *Pseudoceraster persicus* and *Vipera* spp.

The term "subject" or "patient" who is suffering from the bite or sting of a venomous animal is a mammal, preferably humans, and includes household pets and livestock, including but not limited to dogs, cats, sheep, horses, cows, goats, and pigs.

DETAILED DESCRIPTION OF THE INVENTION

Envenomation by adult vipers of *Crotalus* species is fibrinogenolytic as previously described and reviewed (see, Bell W R. Drugs 1997; 54(Suppl 3); 18-31; Budzynski A Z, et al., Blood 1984; 63:1-14; Chiou S H, et al., Biochem Biophys Res Comm 1992; 187:389-396; Willis T W, Tu A T. Biochemistry 1988; 27:4769-4777). Hypofibrinogenemia/afibrinogenemia may contribute to hemorrhage following such envenomation (see, Cruz N S, Alvarez R G. Pediatr Emerg Care 1994; 10:30-33; Fazelat J, et al., Clin Toxicol (Phila) 2008; 46:823-826; Ruha A M, et al., Wilderness Environ Med 2009; 20:156-160). The venom of *Crotalus* vipers sequentially cleave the α and β chains of fibrinogen at sites separate from those recognized by thrombin, resulting in hemostatically inert fibrinogen (see, Bell W R. Drugs 1997; 54(Suppl 3); 18-31; Chiou S H, et al., Biochem Biophys Res Comm 1992; 187:389-396). Hypofibrinogenemia following *Crotalus* envenomation is not readily corrected by administration of human plasma derivatives, suggesting that this process continues for many hours after the bite (see, Budzynski A Z, et al., Blood 1984; 63:1-14). Administration of antivenom attenuates catalysis of fibrinogen after snakebite. In sum, while the molecular lesions to fibrinogen caused by such envenomation are well known, the treatment has involved an immunological approach. Improved techniques are needed. The present invention addresses such needs.

Experiments conducted during the course of developing embodiments for the present invention demonstrated that iron and carbon monoxide attenuate degradation of plasmatic coagulation by *Crotalus atrox* venom (see, Example I).

Experiments conducted during the course of developing embodiments for the present invention demonstrated that iron and carbon monoxide attenuate *Crotalus atrox* venom-enhanced tissue-type plasminogen activator initiated fibrinolysis (see, Example II).

Experiments conducted during the course of developing embodiments for the present invention demonstrated the effect of iron and carbon monoxide on fibrinogenase-like degradation of plasmatic coagulation by venoms of six *Agkistrodon* species (see, Example III).

Experiments conducted during the course of developing embodiments for the present invention demonstrated that iron and carbon monoxide prevent degradation of plasmatic coagulation by thrombin-like activity in rattlesnake venom (see, Example IV).

Experiments conducted during the course of developing embodiments for the present invention demonstrated the effect of iron and carbon monoxide on fibrinogenase-like degradation of plasmatic coagulation by venoms of four *Crotalus* species (see, Example V).

Experiments conducted during the course of developing embodiments for the present invention demonstrated the effects of iron and carbon monoxide on the fibrinogenolytic activity of *Crotalus atrox* venom (see, Example VI).

Accordingly, the present invention relates to compositions and methods for treating, ameliorating and preventing the toxic effects of venom poisoning. In particular, the invention provides compositions comprising carbon monoxide releasing molecules (CORM) or compositions comprising CORM and iron releasing molecules (IRM) for one or more of enhancing coagulation, reducing fibrinolysis, and/or inactivating venom related metalloproteinase activity in a subject suffering from or at risk of suffering from venom poisoning.

Snake venoms, produced primarily for the procurement of prey or in a defensive role, are complex biological mixtures of upwards of 50 components. Death of prey from a snake bite is due to respiratory or circulatory failure caused by various neurotoxins, cardiotoxins (also called cytotoxins), coagulation factors, and other substances acting alone or synergistically. Snake venoms also contain a number of enzymes which when injected into the prey start tissue digestion. The venoms thus contain substances designed to affect the vital processes such as nerve and muscle function, the action of the heart, circulation of the blood and the permeability of membranes. Most constituents of snake venoms are proteins, but low molecular weight compounds such as peptides, nucleotides and metal ions are also present.

Poisonous (venomous) snakes may be divided into 4 main families, the Colubridae, the Viperidae, the Hydrophidae and the Elapidae. Rattlesnakes which are particular to the American continent are members of a subfamily of venomous snakes from the Viperidae family known as Crotalinae, genera *Crotalus* or *Sistrusus* (rattlesnakes), *Bothrops*, *Apkistrodon* and *Trimerisurus*. The two rattlesnake genera may be broken down still further into species and sub species. These snakes are also called the "pit vipers" due to the presence of facial sensory heat pits; however their most prominent feature is the rattle which when present distinguishes them from all other snakes. Each species or subspecies occupies a distinct geographical location in the North or South America. The venom of each species of rattlesnake contains components which may be common to all rattlesnakes, common to only some smaller groups or may be specific to a single species or subspecies.

The compositions and methods of the present invention are not limited to treating, ameliorating and preventing the toxic effects of a particular type of venom. In some embodiments, the venom is any type of venom that inhibits coagulation in a subject. In some embodiments, the venom is any type of venom that causes fibrinolysis in a subject. In some embodiments, the venom is any type of venom that causes catalysis of fibrinogen in a subject. In some embodiments, the venom is any type of venom that causes degradation of plasma coagulation in a subject. In some embodiments, the venom is any type of venom that causes inactivation of fibrinogen in a subject. In some embodiments, the venom is any type of venom that causes one or more of the following in a subject (e.g., a subject suffering from venom poisoning): coagulation inhibition, fibrinolysis, fibrinogen catalysis, plasma coagulation degradation, and fibrinogen inactivation.

In some embodiments, the venom is *Crotalus* related venom. For example, in some embodiments, the venom is venom from a *Crotalus* species selected from, for example, *C. adamanteus, C. aquilus, C. atrox, C. basilicus, C. cerastes, C. durissus, C. enyo, C. horridus, C. intermedius, C. lannomi, C. lepidus, C. mitchellii, C. molossus, C. oreganus, C. polystictus, C. pricei, C. pusillus, C. ruber, C. scutulatus, C. simus, C. stejnegeri, C. tigris, C. tortugensis, C. totonacus, C. transversus, C. triseriatus, C. viridis*, and *C. willardi*.

In some embodiments, the venom is from one of the following: *Naja naja* (Indian cobra), *Bothrops asper* (Furde-lance), Northern Pacific rattlesnake, Arizona Black rattlesnake, Prairie rattlesnake, Red Diamond rattlesnake, Timber rattlesnake, Eastern Diamondback rattlesnake, and Southern Pacific rattlesnake.

In some embodiments, the venom is from *Contortix contortix, Agkistrodon piscivorus piscivorus, Agkistrodon contortrix contortrix, Agkistrodon contortrix laticinctus,*

*Askistrodon contortix pictigaster*, *Agkistrodon piscivorus leucostoma*, and *Agkistrodon contortrix mokasen*.

The present invention is not limited to a particular manner of treating, ameliorating and preventing the toxic effects of venom poisoning.

In some embodiments, such methods involve administering to a subject (e.g., a human suffering from or at risk of suffering from a venom poisoning) a composition (e.g., a pharmaceutical composition) having a carbon monoxide releasing molecule (CORM). In some embodiments, in vitro or in vivo exposure of such a composition to a biological sample results in release of carbon monoxide from the CORM.

In some embodiments, such methods involve administering to a subject (e.g., a human suffering from or at risk of suffering from a venom poisoning) a composition (e.g., a pharmaceutical composition) having a carbon monoxide releasing molecule (CORM) and an iron releasing molecule (IRM). In some embodiments, in vitro or in vivo exposure of such a composition to a biological sample results in release of carbon monoxide from the CORM and release of iron from the IRM.

Such compositions are not limited to a particular manner of treating, ameliorating and preventing the toxic effects of venom poisoning.

In some embodiments, administration of such a composition to a subject such that carbon monoxide is released from the CORM results in prevention of one or more of venom mediated catalysis of fibrinogen in the subject, venom mediated degradation of plasma coagulation in the subject, venom mediated coagulopathy in the subject, and venom mediated catalysis and inactivation of fibrinogen.

In some embodiments, administration of such a composition to a subject such that carbon monoxide is released from the CORM and iron is released from the IRM results in prevention of one or more of venom mediated catalysis of fibrinogen in the subject, venom mediated degradation of plasma coagulation in the subject, venom mediated coagulopathy in the subject, and venom mediated catalysis and inactivation of fibrinogen.

In some embodiments, the released carbon monoxide from either composition interacts with snake venom associated metalloproteinases (e.g., $Zn^{+2}$ metalloproteinases), wherein the interaction results in inactivation of the snake venom associated metalloproteinase. In some embodiments, such inactivation results in prevention and/or alleviation of pain and neurological effects related to snake venom related metalloproteinase activity (e.g., $Zn^{+2}$ metalloproteinase activity).

Such compositions are not limited to a particular type of carbon monoxide releasing agent. As used herein, a carbon monoxide releasing agent (CORM) refers to a metal carbonyl compound or a pharmaceutically acceptable salt thereof that releases carbon monoxide. The CORM can release carbon monoxide by several methods. For example, the CORM can release carbon monoxide on contact with a suitable solvent or medium, e.g., on contact with an aqueous physiological fluid such as blood or lymph. The CORM can also release carbon monoxide, for example, on contact with physiological cellular materials, such as a tissue, organ, or cell. Another example of a method by which a CORM can release carbon monoxide is by irradiation. The compound may be irradiated prior to administration, for example, to produce a solution of dissolved CO, or may be irradiated in situ after administration.

An example of a CORM or a pharmaceutically acceptable salt thereof suitable for use with the methods described herein is tricarbonyldichlororuthenium (II) dimer (CORM-2). Further examples of CORMs suitable for use with the methods described herein include tricarbonylchloro(glycinato)ruthenium (II) (CORM-3), sodium boranocarbonate, dimanganese decacarbonyl, and iron pentacarbonyl.

Such compositions are not limited to a particular type of iron releasing agent. As used herein, an iron releasing agent (IRM) refers to a compound or a pharmaceutically acceptable salt thereof that releases iron. The IRM can release iron by several methods. For example, the IRM can release iron on contact with a suitable solvent or medium, e.g., on contact with an aqueous physiological fluid such as blood or lymph. The IRM can also release iron, for example, on contact with physiological cellular materials, such as a tissue, organ, or cell. Another example of a method by which a IRM can release iron is by irradiation. The compound may be irradiated prior to administration, for example, to produce a solution of dissolved iron, or may be irradiated in situ after administration.

Examples of IRMs or a pharmaceutically acceptable salt thereof suitable for use with the methods described herein include, but are not limited to, ferric chloride, iron dextran, ferric gluconate, iron sucrose, ferumoxytol, ferric carboxymaltose, and iron isomaltoside.

CORMs and IRMs and pharmaceutically acceptable salts thereof suitable for the methods described herein include those including a transition metal or metalloid and one or more carbonyl ligand(s). The transition metal or metalloid, for example, can be ruthenium, iron, manganese, cobalt, nickel, molybdenum, rhodium, or boron. The carbonyl ligand(s) can be coordinated to the metal center, or bonded to other groups by ionic or covalent bonds. The CORMs and IRMs and pharmaceutically acceptable salts thereof for use with the methods described herein can also include additional ligands that may modulate a particular property of the CORM and/or IRM, such as, for example, the rate of releasing carbon monoxide or iron, solubility, hydrophobicity, stability, or electrochemical potential. The additional ligands can be, for example, halides, sulfoxides, natural and synthetic amino acids, aromatics, carboxylates, ethers, alcohols, or nitriles. The CORM or IRM or a pharmaceutically acceptable salt thereof may also include a targeting moiety useful for facilitating release of carbon monoxide or iron at an appropriate site. The targeting moiety can be, for example, capable of binding a receptor on a particular target cell surface to promote release of carbon monoxide or iron at the required site.

The compositions described herein can be prepared in a variety of ways. The compositions can be synthesized using various synthetic methods. At least some of these methods are known in the art of synthetic organic chemistry. The compositions described herein can be prepared from readily available starting materials. Optimum reaction conditions can vary with the particular reactants or solvent used, but such conditions can be determined by one skilled in the art.

Reactions to produce the compositions described herein can be carried out in solvents, which can be selected by one of skill in the art of organic synthesis. Solvents can be substantially nonreactive with the starting materials (reactants), the intermediates, or products under the conditions (e.g., temperature and pressure) at which the reactions are carried out. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

The CORMs and IRMs described herein or pharmaceutically acceptable salts thereof can be provided in a composition including a CORM and an IRM or a pharmaceutically acceptable salt thereof and a blood product. The blood product can be, for example, a cryoprecipitate or fresh frozen plasma. The CORM and IRM for the composition can be selected from any of the CORMs described herein (e.g., tricarbonyldichlororuthenium (II) dimer, tricarbonylchloro (glycinato)ruthenium (II), sodium boranocarbonate, dimanganese decacarbonyl, iron pentacarbonyl, and derivatives thereof) (e.g., ferric chloride, iron dextran, ferric gluconate, iron sucrose, ferumoxytol, ferric carboxymaltose, and iron isomaltosid, and derivatives thereof).

One or more of the compositions described herein or pharmaceutically acceptable salts thereof can be provided in a pharmaceutical composition. The pharmaceutical composition can be formulated in accordance with its use and mode of administration. The compositions will include a therapeutically effective amount of one or more of the CORMs and IRMs described herein or derivatives thereof in combination with a pharmaceutically acceptable carrier and, optionally, can further include other agents, including other therapeutic agents. These compositions can be prepared in any manner available in the art and can be administered in a number of ways depending on whether local or systemic treatment is desired, on the area to be treated, the subject to be treated, and other variables. Thus, the disclosed compositions can be administered, for example, orally, parenterally (e.g., intravenously), intraventricularly, intramuscularly, intraperitoneally, transdermally, extracorporeally, or topically. The compositions can be administered locally.

By pharmaceutically acceptable is meant a material that is not biologically or otherwise undesirable, which can be administered to an individual along with the selected composition without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing a CORM and IRM as described herein or pharmaceutically acceptable salts thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compositions described herein or pharmaceutically acceptable salts thereof include capsules, tablets, pills, powders, and granules. In such solid dosage forms, the compositions described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active portions of the compositions in a certain part of the intestinal tract in a delayed manner. Examples of embedding compositions that can be used are polymeric substances and waxes. The active portions of the compositions can also be in micro-encapsulated form, if appropriate, with one or more of the above-mentioned excipients.

Liquid dosage forms for oral administration of the compositions described herein or pharmaceutically acceptable salts thereof include pharmaceutically acceptable emulsions, solutions, suspensions, syrups, and elixirs. In addition to the active portions of the compositions, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active portions of the compositions, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the CORMs and IRMs described herein or pharmaceutically acceptable salts thereof for rectal administrations are optionally suppositories, which can be prepared by mixing the active portions of the compositions with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the CORMs and IRMs described herein or pharmaceutically acceptable salts thereof include ointments, powders, sprays, and inhalants. For example, the CORMs and IRMs and pharmaceutically acceptable salts thereof can be formulated as a spray for the nasopharynx, the lung, or skin. The CORMs and IRMs described herein or pharmaceutically salts thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the active portions of the compositions described herein. The term salts refers to the relatively non-toxic, inorganic and organic acid addition salts of the active portions of the compositions described herein. These salts can be prepared in situ during the isolation and purification of the active portions of the compositions or by separately reacting a purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught herein).

As disclosed herein, the CORMs and IRMs and pharmaceutically acceptable salts thereof described herein are useful in treating, ameliorating and/or preventing the toxic effects of venom poisoning. For example, the CORMs and IRMs and pharmaceutically acceptable salts thereof described herein are useful in preventing one or more of venom mediated catalysis of fibrinogen in the subject, venom mediated degradation of plasma coagulation in the subject, venom mediated coagulopathy in the subject, and venom mediated catalysis and inactivation of fibrinogen. The methods described herein comprise selecting a subject suffering from or at risk for suffering from venom related poisoning and administering to a subject an effective amount of the CORM and IRM or a pharmaceutically acceptable salt thereof. The CORM and IRM (e.g., composition a CORM and IRM) can be administered locally or systemically in accordance with the subject's needs.

The methods and compositions as described herein are useful for both prophylactic and therapeutic treatment. For prophylactic use, a therapeutically effective amount of a composition comprising CORMs and IRMs and pharmaceutically acceptable salts thereof are administered to a subject at risk of suffering from venom related poisoning. Prophylactic administration can occur for several hours to days prior to such a potential venom poisoning. Prophylactic administration can be used, for example, in preparation for exposure to a region wherein the likelihood for venom poisoning is increased. Therapeutic treatment involves administering to a subject an effective amount of a composition comprising CORMs and IRMs as described herein or pharmaceutically acceptable salts thereof after venom poisoning has commenced.

Administration of the CORMs and IRMs described herein or pharmaceutically acceptable salts thereof can be carried out using therapeutically effective amounts of the CORMs and IRMs described herein or pharmaceutically acceptable salts thereof for periods of time effective to control the venom poisoning (e.g., the time necessary to enhance coagulation or to reduce fibrinolysis). For example, the CORMs and IRMs described herein or pharmaceutically acceptable salts thereof can be administered as a single dose (i.e., bolus dosage) or as multiple doses.

The effective amount of the CORMs and IRMs described herein or pharmaceutically acceptable salts thereof can be determined by one of ordinary skill in the art and includes exemplary dosage amounts for a subject of from about 25 µM to about 200 µM of the CORM or approximately 350-1000 mg of CORM (e.g., 250 mg, 300 mg, 350 mg, 500 mg, 650 mg, 800 mg, 950 mg, 1000 mg, 1050 mg, 1500 mg) and between approximately 5-25 mg or iron (e.g., 2.5 mg, 5 mg, 10 mg, 15 mg, 20 mg, 25 mg, 30 mg, 50 mg). Alternatively, the dosage amount can be from about 50 µM to about 100 µM of the CORM, or about 100 µM of CORM. Those of skill in the art will understand that the specific dose level and frequency of dosage for any particular subject will vary and will depend upon a variety of factors, including the metabolic stability and length of action of the CORM and IRM, the species, the mode and time of administration, the rate of excretion, drug combination, and the type and severity of the particular condition.

In some embodiments, the amount of CORM and IRM in the composition is such that upon administration to a subject (e.g., a human subject), the composition is able to treat, ameliorate and/or prevent the toxic effects of venom poisoning. In some embodiments, the amount of CORM and IRM in the composition is such that upon administration to a subject (e.g., a human subject), the composition is able to prevent one or more of venom mediated catalysis of fibrinogen in the subject, venom mediated degradation of plasma coagulation in the subject, venom mediated coagulopathy in the subject, and venom mediated catalysis and inactivation of fibrinogen.

The administration of the CORMs described herein or pharmaceutically acceptable salts thereof can be administered systemically or regionally to an area localized to the site of venom poisoning (e.g., region of a snake bite) to allow carbon monoxide and iron to be available for a controllable time frame.

The method of treating, ameliorating and/or preventing the toxic effects of venom poisoning in a subject can further comprise administering to the subject an additional agent. Thus, the provided compositions and methods can include one or more additional agents. The one or more additional agents and the CORMs and IRMs described herein or pharmaceutically acceptable salts thereof can be co-administered. Co-administration, as used herein, includes administration in any order, including simultaneous administration, as well as temporally spaced order of up to several days apart. The methods can also include more than a single administration of the one or more additional agents and/or the CORMs and IRMs described herein or pharmaceutically acceptable salts thereof. The administration of the one or more additional agents and the CORMs and IRMs described herein or pharmaceutically acceptable salts can be by the same or different routes and concurrently or sequentially.

The additional agents can include, for example, therapeutic agents. Therapeutic agents include but are not limited to antibiotics, anesthetics, analgesics, antihistamines, antimicrobials, antifungals, antivirals, steroidal and non-steroidal anti-inflammatory agents, chemotherapeutic agents, antibodies, conventional immunotherapeutic agents, cytokines, chemokines, and/or growth factors. In some embodiments, the additional agent is an antivenom (e.g., antivenom against *Crotalus* venom) (e.g., Crotalidae Polyvalent Immune Fab Ovine (CroFab) or Crotalinae Equine Immune F(ab)2 Antivenom (Anavip)).

Further, the CORMs and IRMs described herein or pharmaceutically acceptable salts thereof can be co-administered with additional agents that aid in controlling bleeding. For example, the CORMs described herein or pharmaceutically acceptable salts thereof can be co-administered with a hemostatic agent, a coagulant, or an anti-fibrinolytic medication. Examples of anti-fibrinolytic agents useful with the methods described herein include aminocaproic acid and tranexamic acid. Other agents that are useful in controlling bleeding, including blood coagulation factors (e.g., factor VIII, factor IX, factor XIII, von Willebrand's factor), fibrin, thrombin, recombinant activated factor VII, prothrombin complex concentrate, and FEIBA (Baxter, Vienna, Austria), can also be co-administered with the CORMs and IRMs described herein or pharmaceutically acceptable salts thereof.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compositions or agents is given first followed by the second). Thus, the term combination is used to refer to either concomitant, simultaneous, or sequential administration of two or more agents.

The CORMs and IRMs described herein or pharmaceutically acceptable salts thereof, with or without additional agents, can be administered at or near the site of venom poisoning. The CORMs and IRMs can also be administered, for example, topically, locally, intraveneously, or intramuscularly. Further, the CORM and IRM can be formulated for administration, for example, by aerosol sprays, ointments, sutures, bandages, patches, autoinjectors (e.g., similar to epipen autoinjector technology), surgical dressings, wound packings, gauze, swabs, liquids, pastes, creams, lotions, foams, gels, emulsions, or powders. Thus, provided herein are aerosol sprays, ointments, sutures, bandages, patches, autoinjectors, surgical dressings, wound packings, gauze, swabs, liquids, pastes, creams, lotions, foams, gels, emulsions, powders, needles, probes, dental instruments, dental floss, and mouth wash comprising a CORM and IRM.

In certain embodiments, kits are provided comprising compositions comprising therapeutically effective amounts of CORM and IRM. In some embodiments, such kits further comprise an antivenom composition. In some embodiments, such kits further comprise instructions for administering the composition to a living mammal. In some embodiments, such kits further comprise one or more of a hemostatic agent, a coagulant, an anti-fibrinolytic medication, a blood coagulation factor, fibrin, thrombin, recombinant activated factor VII, prothrombin complex concentrate, FEIBA, or a therapeutic agent selected from the group consisting of an antibiotic, an anesthetic, an analgesic, an antihistamine, an antimicrobial, an antifungal, an antiviral, and an anti-inflammatory agent.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

The following examples are illustrative, but not limiting, of the compositions, and methods of the present invention. Other suitable modifications and adaptations of the variety of conditions and parameters normally encountered in clinical therapy and which are obvious to those skilled in the art are within the spirit and scope of the invention.

Example I

Recent investigations have revealed that fibrinogen can be modified by iron and carbon monoxide (CO), resulting in plasma thrombi that commence coagulation earlier, with greater formation velocity and final clot strength compared to clots that are iron and CO naïve (see, Nielsen V G, Pretorius E. Blood Coagul Fibrinolysis 2014; 25:695-702). CO enhances fibrinogen as a thrombin substrate by binding to heme group(s) bound to fibrinogen (see, Nielsen V G, et al., Blood Coagul Fibrinolysis 2011; 22:443-447) whereas ferric iron binds to fibrinogen in a reversible manner, with iron enhancement of coagulation attenuated by chelation (see, Nielsen V G, Pretorius E. Blood Coagul Fibrinolysis 2014; 25:845-850). Iron and CO enhance fibrinogen by separate mechanisms; iron decreases the time to onset of coagulation and increases the velocity of clot formation without affecting final clot strength, whereas CO increases the velocity of clot formation and increases clot strength without affecting the time to onset of coagulation (see, Nielsen V G, Pretorius E. Blood Coagul Fibrinolysis 2014; 25:695-702). When combined, the velocity of clot formation increases in an additive manner by both these agents (see, Nielsen V G, Pretorius E. Blood Coagul Fibrinolysis 2014; 25:695-702). While definitive investigation remains to be performed, it is strongly suspected that iron and CO binding to fibrinogen changes molecular configuration, improving catalysis by thrombin and potentially enhancing polymerization and crosslinking of fibrin polymers. Thus, it was hypothesized that pretreatment of plasma with iron and CO may attenuate the ability of *Crotalus* derived venom to catalyze and inactivate fibrinogen.

Two-hundred mg of lyophilized, pooled venom was obtained from four western diamondback rattlesnakes (*Crotalus atrox*) for experimentation. Venom was reconstituted in calcium-free phosphate buffered saline (PBS, Sigma-Aldrich, Saint Louis, Mo., USA) at a concentration of 20 mg/ml, aliquoted, and then stored at −80° C. until experimentation at the University of Arizona. Pooled human normal plasma (George King Bio-Medical, Overland Park, Kans., USA) anticoagulated with sodium citrate was rapidly thawed at 37° C. and used for experimentation. To assess the effects of pretreatment of fibrinogen with iron, CO, or both, 1% additions of PBS, ferric chloride ($FeCl_3$, 99.9% pure, Sigma-Aldrich, Saint Louis, Mo., USA) in PBS, or CORM-2 (tricarbonyldichlororuthenium (II) dimer, a CO releasing molecule, Sigma-Aldrich, Saint Louis, Mo., USA) dissolved in dimethyl sulfoxide (DMSO, Sigma-Aldrich, Saint Louis, Mo., USA). The final concentrations of $FeCl_3$ and CORM-2 were 10 μM and 100 μM, respectively; these concentrations are associated with nearly maximal augmenting effects on coagulation kinetics (see, Nielsen V G, et al., Blood Coagul Fibrinolysis 2014; 25:695-702). Plasma was exposed to these various agents for at least 5 min prior to incubations with venom.

The final volume for all subsequently described plasma sample mixtures was 359.4 μl. Sample composition consisted of 326 μl of plasma; 10 μl of tissue factor reagent (0.1% final concentration in distilled water; Diagnostica Stago S.A.S., Asnieres sur Seine, France) and 3.4 μl of PBS or venom (final concentration 0.5 μg/ml). In pilot studies, experiments tested the effects of 5 min of incubation at 37° C. of 2.0, 1.5 and 1.0 μg/ml of venom on coagulation but found a complete loss of thrombus formation. However, a concentration of 0.5 μg/ml of venom appeared to impair but not eliminate coagulation, so this concentration was subsequently used in all experimentation. The aforementioned plasma and venom mixtures were placed in a disposable cup in a computer-controlled Thrombelastograph® hemostasis system (Model 5000, Haemoscope Corp., Niles, Ill., USA) and incubated for 5 or 20 min at 37° C., with addition of 20 μl of 200 mM $CaCl_2$ as the last step to initiate clotting. Data were collected at 37° C. for 15 min after 5 min of incubation, whereas samples incubated with venom for 20 min had data collected for 30 min, given the prolonged onset of coagulation and diminished rate of thrombus formation. The following elastic modulus-based parameters previously described (see, Nielsen, et al., 2014, Blood Coagul. Fibrinolysis 25:695-702; Nielsen, et al., 2011, Blood Coagul. Fibrinolysis 22: 443-447); Nielsen V G, et al., Blood Coagul Fibrinolysis 2014; 25:845-850) were determined: time to maximum rate of thrombus generation (TMRTG): this is the time interval (min) observed prior to maximum speed of clot growth; maximum rate of thrombus generation (MRTG): this is the maximum velocity of clot growth observed (dynes/cm$^2$/sec); and total thrombus generation (TTG, dynes/cm$^2$), the final viscoelastic resistance observed after clot formation.

Data are presented as mean+SD. A commercially available statistical program was used for one-way analysis of variance followed by Holm-Sidak post hoc analyses (SigmaStat 3.1, Systat Software, Inc., San Jose, Calif., USA). Graphics depicting viscoelastic data were generated with a commercially available program (OrigenPro 7.5, OrigenLab Corporation, Northampton, Mass., USA; CorelDRAW12, Corel Corporation, Mountain View, Calif., USA).

Figure 1:
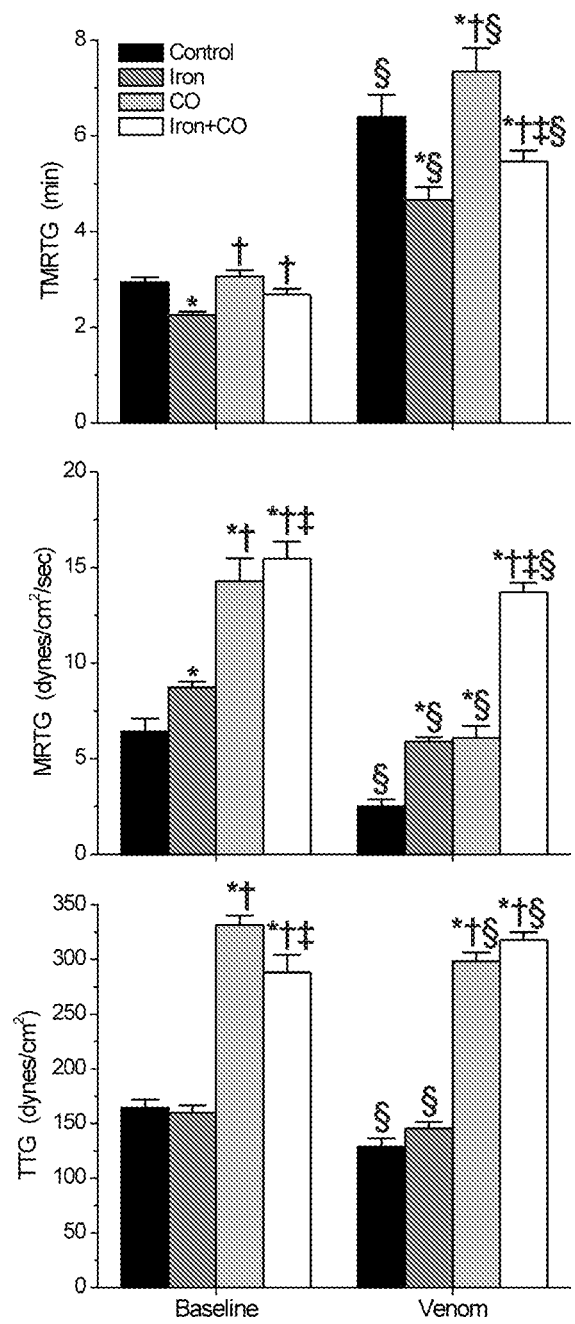
FIG. 1: Effects of venom, iron and CO on plasmatic coagulation. The effects of iron and CO on plasmatic coagulation before and after incubation with venom for 5 min are displayed. *$P<0.05$ vs. control condition within time point; †$P<0.05$ vs. iron within condition within time point; ‡$P<0.05$ vs. CO; § $P<0.05$ vs. same condition at baseline.

As seen in FIG. 1, under baseline (venom naïve) conditions, compared to plasma without any additions, iron exposure significantly decreases TMRTG (top panel), increases MRTG (middle panel), but does not affect TTG (bottom panel); CO exposure from CORM-2 results in no change in TMRTG but does result in a significant increase in MRTG and TTG compared to plasma without additions; and a combination of iron and CO addition result in an even greater and significant increase in MRTG and nearly as great increase in TTG compared to plasma without addition. After incubation with venom for 5 min, TMRTG was significantly prolonged in all conditions, but samples with iron or iron and CO addition has significantly smaller TMRTG values (less than double baseline values of iron/CO naïve plasma) than samples without iron/CO additions or with CO addition alone. Venom exposure significantly decreased MRTG in plasma with addition or with addition of iron or CO alone; however, in samples with both iron and CO addition, MRTG did not significantly change and was still approximately twice the baseline value of plasma without additions. Importantly, plasma exposed to either iron or CO had MRTG values significantly greater than plasma without additions exposed to venom. Lastly, with regard to clot strength, venom exposure significantly decreased TTG in all conditions compared to matched venom naïve samples, with the exception of plasma exposed to iron and CO, which had significantly greater TTG values compared to matched venom naïve samples. In samples with CO addition clot strength was still significantly greater than samples without CO added, and still about twice as strong as baseline values of venom, iron and CO naïve plasma. In sum, iron and CO, separately or in combination, attenuated some or all of the effects of incubation with venom on plasmatic coagulation.

Figure 2:
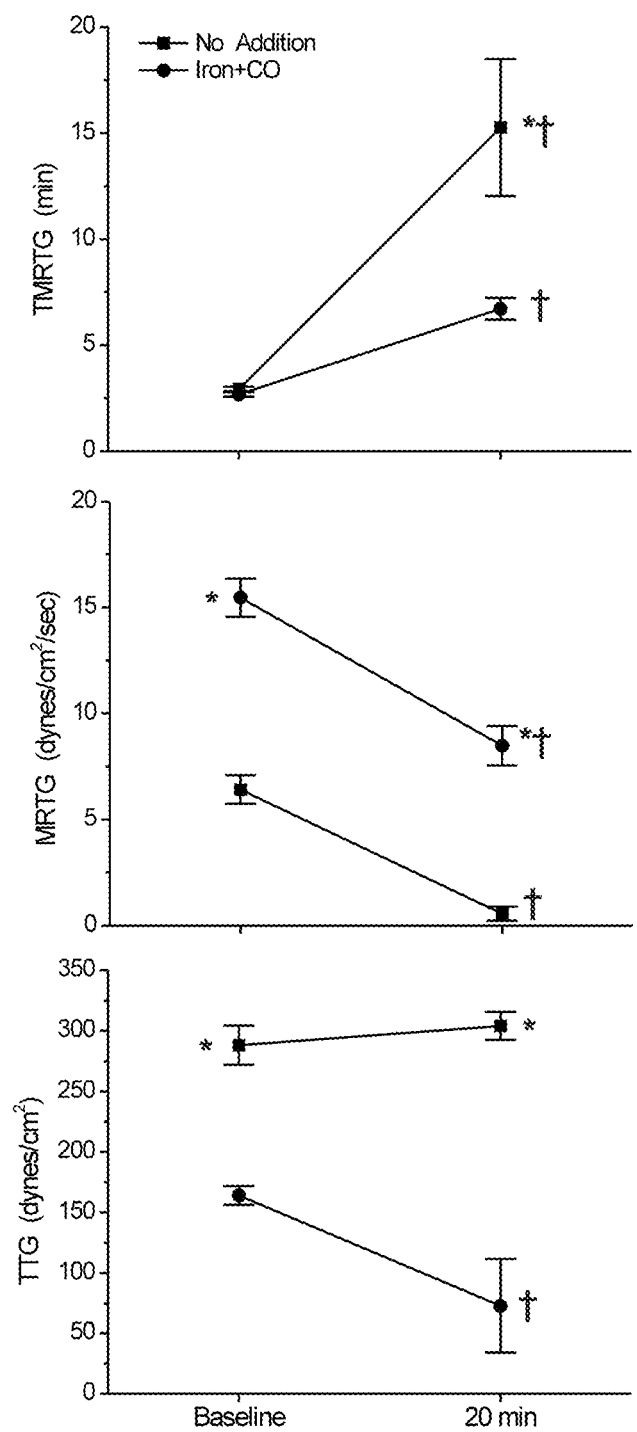
FIG. 2: Attenuation of venom mediated degradation of plasmatic coagulation by iron and CO. The effects of iron and CO on plasmatic coagulation before and after prolonged incubation with venom for 20 min are displayed. *$P<0.05$ vs. plasma without addition of iron and CO; †$P<0.05$ vs. same condition at baseline.

Prolonged incubation for 20 min with venom markedly degraded coagulation as depicted in FIG. 2. As seen in the top panel, plasma without iron/CO additions had a significant, 5-fold increase in TMRTG values compared to baseline conditions. Plasma with iron/CO addition have a significant, 2.5-fold increase in TMRTG values compared to baseline (venom naïve) values, which in turn was significantly less than values of plasma without iron/CO additions after venom exposure. With regard to velocity of clot formation, as displayed in the middle panel, venom exposure significantly decreased MRTG values by over 90% compared to baseline values in plasma without iron/CO additions, whereas plasma with iron/CO addition had a significant decrease in MRTG values to 45% of baseline values, with a significant difference seen between the two conditions after venom exposure. Finally, with regard to clot strength, TTG values of plasma without additions were noted to significantly decrease by 56% compared to baseline values, whereas plasma with iron/CO addition had no significant change in TTG values, which were significantly greater by 2-fold compared to plasma without additions.

The primary finding of the present investigation was that iron and CO, separately or in combination, attenuated venom mediated degradation of plasmatic coagulation. It is likely that the underlying mechanism of these phenomena are conformational changes in fibrinogen structure by iron and CO, simultaneously making fibrinogen a more favorable substrate for thrombin and decreasing the efficiency of catalysis of fibrinogen by venom. In support of this conclusion, it should be noted that while TMRTG increased and MRTG decreased in the presence of venom despite exposure to iron and CO, the degree of coagulation derangement was far less than in plasma without iron/CO additions. Further, there was essentially no important change in clot strength in plasma with iron and CO addition; in fact, plasma clot strength remained about twice baseline strength after exposure to venom for 5 or 20 min. In addition to these coagulation kinetic data, it was noted in a previous article that analysis of purified fibrinogen with liquid chromatography-mass spectrometry demonstrated a loss of recovery of portions of the α and γ chains following proteinase digestion after exposure to CO, likely secondary to the inability to digest these sections of fibrinogen after CO mediated changes (see Example I). Given the data of the present study and previous investigations concerning the additive, positive effects of iron and CO binding on plasmatic coagulation (see, Nielsen, et al., 2014, Blood Coagul. Fibrinolysis 25:695-702; Nielsen, et al., 2011, Blood Coagul. Fibrinolysis 22: 443-447); Nielsen V G, et al., Blood Coagul Fibrinolysis 2014; 25:845-850), it seems likely that iron and CO somehow change the α and/or β chain conformation, whereas CO affects the γ chain of fibrinogen. In sum, iron and CO likely protect fibrinogen from catalysis secondary to changes that cause amino acid targets less accessible to venom proteases.

With regard to elemental iron or CORM-2, the amounts used in vitro in the present investigation are far less than has been administered in vivo (see, Kshirsagar A V, et al., PLoS ONE 2013; 8:e78930; Nielsen V G, et al., Blood Coagul Fibrinolysis 2011; 22:756-759; Nielsen V G, et al., Blood Coagul Fibrinolysis 2012; 23:104-107). In a conscious rabbit ear-bleed model, CORM-2 was injected at a dose of 10 mg/kg (equivalent to 279 µM final concentration) to effect CO mediated resistance to platelet-inhibition or tissue-type plasminogen mediated coagulopathy without adverse effects noted (see, Nielsen V G, et al., Blood Coagul Fibrinolysis 2011; 22:756-759; Nielsen V G, et al., Blood Coagul Fibrinolysis 2012; 23:104-107). With regard to iron, in order to administer a dose that would result in an increase of 10 µM in the circulation, consider the following: assuming a molecular weight of 55.8 atomic mass units for elemental iron, if 0.558 µg/ml is multiplied by 70 ml/kg (estimated blood volume) and by 70 kg (an average weight), the product is approximately 2.7 mg of iron. It is common to infuse up to 100 mg of iron to augment red blood cell production, a value well over 30-fold of the amount required to enhance coagulation (see, Kshirsagar A V, et al., PLoS ONE 2013; 8:e78930). Considered as a whole, administration of iron and CO in the quantities required to modify fibrinogen to attenuate degradation by venom may very well be easily clinically achievable without adverse side effects.

It is important to consider the multiple regional and systemic effects of snake venom, which are mediated in part by zinc metalloproteinases that induce a hemorrhagic state and myotoxins that destroy endothelial and muscle cells, and potential pulmonary and circulatory failure (see, Lefkowitz R Y, et al., J Intensive Care Med 2013; 28:314-319; Massey D J, et al., J Proteomics 2012; 75:2576-2587; Lavonas E J, et al., Ann Emerg Med 2011; 57:128-137). Further, the tissue damage that occurs may permanently debilitate the snake-bite victim and often times require surgical interventions that include fasciotomies for ischemic compartment syndromes (see, Toschlog E A, et al., J Am Coll Surg 2013; 217:726-735).

Example II

In addition to their fibrinogen degrading properties, venoms derived from various rattlesnake species (*Crotalus* species) have been demonstrated to have thrombolytic properties in vivo in rodent models (see, Willis T Wl, et al., Thromb Res 1989; 53:19-29; Rael E D, et al., Haemostasis 1992; 22:41-49; Tu A T, et al., Toxicon 1996; 34:1295-1300), and specifically have been found to enzymatically digest two key antifibrinolytic enzymes in vitro, alpha-2-antiplasmin and alpha-2-macroglobulin (see, Baramova E N, et al., *Biochemistry* 1990; 29:1069-1074; Svoboda Pl, et al., *Toxicon* 1995; 33:1331-1346). Thus, it would be anticipated that degradation of these two enzymes would enhance endogenous fibrinolysis, significantly contributing to the coagulopathy associated with envenomation with *Crotalus* species venom.

Thus, it is of interest that iron and carbon monoxide (CO) have been found to enhance antifibrinolytic resistance to tissue-type plasminogen activator in human plasma (see, Nielsen V G, Pretorius E. *Blood Coagul Fibrinolysis* 2014; 25:695-702), and CO specifically enhances alpha-2-antiplasmin activity in vitro in human plasma (see, Arkebauer M R, et al., *Blood Coagul Fibrinolysis* 2011; 22:712-719) and in vivo in rabbits (see, Nielsen V G, et al., *Blood Coagul Fibrinolysis* 2012; 23:104-107). Given the recent finding that likely conformational changes in fibrinogen induced by iron and CO greatly attenuated the effects of *Crotalus atrox* venom on coagulation (see, Nielsen V G, Boyer L V. Iron and carbon monoxide attenuate degradation of plasmatic coagulation by *Crotalus atrox* venom. *Blood Coagul Fibrinolysis*, in co review), it was hypothesized that pre-exposure of human plasma to iron and CO could attenuate fibrinolysis by perhaps changing antifibrinolytic enzyme conformation, rendering the enzymes less vulnerable to venom-mediated catalysis. Thus, the purpose of these in vitro experiments was to determine if iron and CO exposure could diminish *Crotalus atrox* venom enhancement of tissue-type plasminogen activator (tPA) mediated fibrinolysis in human plasma.

Rattlesnake Venom.

Two hundred mg of lyophilized, pooled venom was obtained from four western diamondback rattlesnakes (*Crotalus atrox*) for experimentation. Venom was reconstituted in calcium-free phosphate buffered saline (PBS, Sigma-Aldrich, Saint Louis, Mo., USA) at a concentration of 20 mg/ml, aliquoted, and then stored at −80° C. until experimentation at the University of Arizona.

Human Plasma Exposure to Iron, CO and Venom.

Pooled normal plasma (George King Bio-Medical, Overland Park, Kans., USA) anticoagulated with sodium citrate was rapidly thawed at 37° C. and used for experimentation. To assess the effects of pretreatment of antifibrinolytic plasma proteins with iron, CO, or both, 1% additions of PBS, ferric chloride ($FeCl_3$, 99.9% pure, Sigma-Aldrich, Saint Louis, Mo., USA) in PBS, or CORM-2 (tricarbonyldichlororuthenium (II) dimer, a CO releasing molecule, Sigma-Aldrich, Saint Louis, Mo., USA) dissolved in dimethyl sulfoxide (DMSO, Sigma-Aldrich, Saint Louis, Mo., USA) were used. The final concentrations of $FeCl_3$ and CORM-2 were 10 µM and 100 µM, respectively; these concentrations are associated with nearly maximal augmenting effects on coagulation kinetics (see, Nielsen V G, Pretorius E. Blood Coagul Fibrinolysis 2014; 25:695-702) and effectively decreased fibrinogen digestion by *Crotalus atrox* venom. Plasma was exposed to these various agents for at least 5 min prior to incubations with venom.

Fibrinolytic Kinetic Assessments.

The final volume for all subsequently described plasma sample mixtures was 359.4 µl. Sample composition consisted of 316 µl of plasma; 10 µl of tissue factor reagent (0.1% final concentration in distilled water; Diagnostica Stago S.A.S., Asnieres sur Seine, France), 10 µl of tissue type plasminogen activator (tPA, 580 IU/µg, Genentech, Inc., San Francisco, Calif., USA; 100 IU/ml final concentration) and 3.4 µl of PBS or venom (final concentration 0.5-2.0 µg/ml). A 5 min of incubation at 37° C. of 1.0 µg/ml of venom resulted in a complete loss of thrombus formation. However, a concentration of 0.5 µg/ml of venom appeared to significantly impair but not eliminate coagulation, so this concentration was used to establish effects on fibrinolysis. The aforementioned plasma and venom mixtures were placed in a disposable cup in a computer-controlled Thrombelastograph® hemostasis system (Model 5000, Haemoscope Corp., Niles, Ill., USA) and incubated for 5 min at 37° C., with addition of 20 µl of 200 mM $CaCl_2$ as the last step to initiate clotting. Data were collected at 37° C. until clot lysis time (CLT) was observed. The following elastic modulus-based parameters previously described (see, Nielsen V G, Pretorius E. Blood Coagul Fibrinolysis 2014; 25:695-702) were determined: time to maximum rate of thrombus generation (TMRTG): this is the time interval (min) observed prior to maximum speed of clot growth; maximum rate of thrombus generation (MRTG): this is the maximum velocity of clot growth observed (dynes/$cm^2$/sec); total thrombus generation (TTG, dynes/$cm^2$), the final viscoelastic resistance observed after clot formation; time to maximum rate of lysis (TMRL, min), maximum rate of lysis (MRL, dynes/$cm^2$/sec) and CLT (min). Lastly, to assess if venom had thrombolytic properties that were tPA independent, n=4 replicates were performed wherein no tPA was added and data were collected for 3 h.

Statistical Analyses.

Data are presented as mean±SD. All conditions unless otherwise indicated were represented by n=8 replicates. This number of replicates reliably provides a statistical power >0.8 for P<0.05 (see, Nielsen V G, Pretorius E. Blood Coagul Fibrinolysis 2014; 25:695-702). A commercially available statistical program was used for two-way analysis of variance (ANOVA) to assess interactions of venom and tPA on coagulation kinetics and interactions of iron and CO on venom-enhanced fibrinolysis (SigmaStat 3.1, Systat Software, Inc., San Jose, Calif., USA). Additional one-way ANOVA followed by Holm-Sidak post hoc analyses were performed to assess differences between the conditions. Graphics depicting viscoelastic data were generated with a commercially available program (OrigenPro 7.5, OrigenLab Corporation, Northampton, Mass., USA).

Assessment of Direct Thrombolytic Effects of Venom.

After 3 h, no sign of loss of clot strength was observed in the 4 replicates exposed to 0.5 µg/ml venom, with the TTG value of 172±8 dynes/$cm^2$ noted. Thus, in human plasma, no intrinsic thrombolysis occurred after venom exposure.

Assessment of Venom on tPA Mediated Changes in Coagulation Kinetics.

Figure 3:
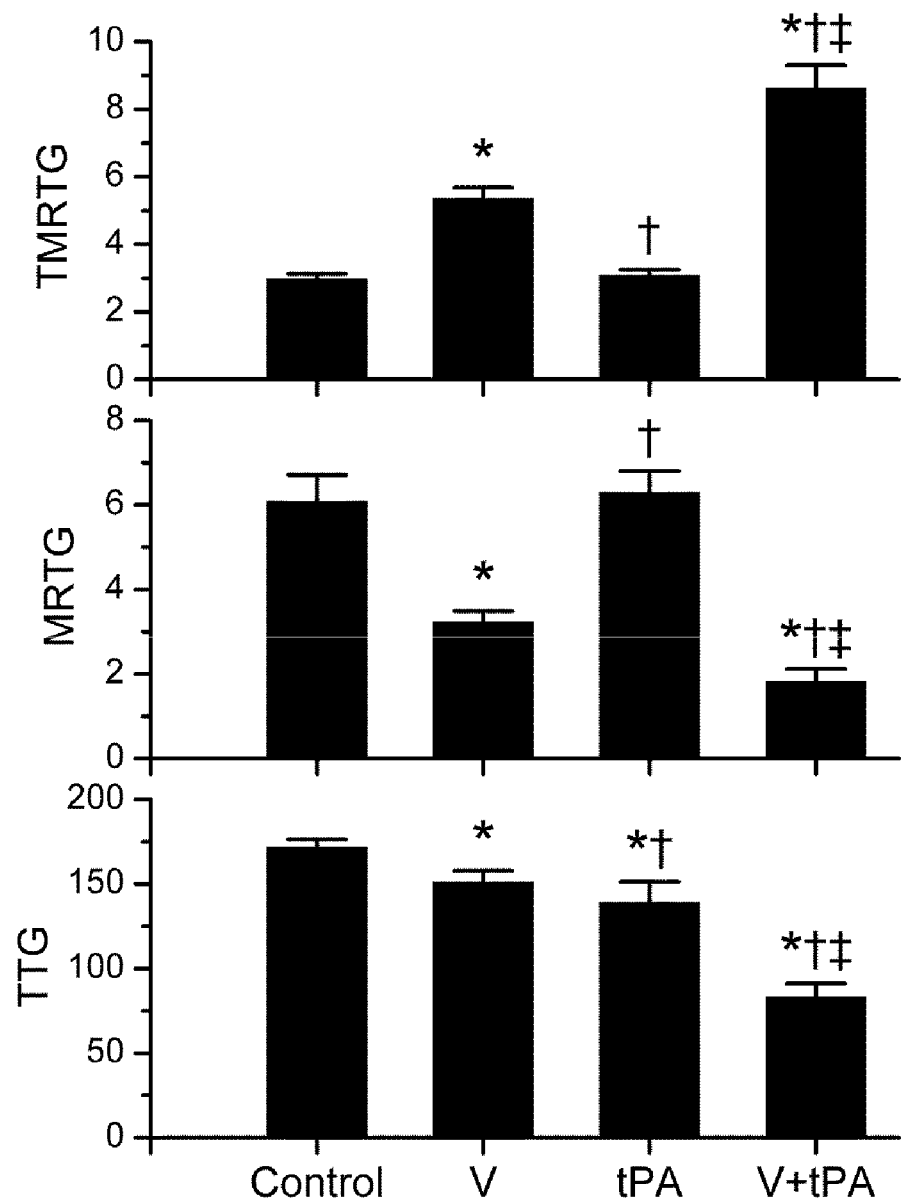
FIG. 3: Effects of venom on coagulation kinetics in the presence or absence of tPA. Top panel—TMRTG=time to maximum rate of thrombus generation (min); middle panel—MRTG=maximum rate of thrombus generation (dynes/cm²/sec); bottom panel—TTG=total thrombus generation (dynes/cm²). Control=plasma without additions; V=5 min incubation with 0.5 μg/ml venom; tPA=100 IU/ml tPA added; V+tPA=exposure to both V and tPA. *$P<0.05$ vs. control; †$P<0.05$ vs. V; ‡$P<0.05$ vs. tPA.

The results of these analyses are displayed in FIG. 3. There was a significant interaction between venom exposure and tPA addition that degraded coagulation kinetics as assessed by 2-way ANOVA. With regard to TMRTG (top panel), tPA alone did not prolong this parameter, venom did prolong TMRTG compared to control conditions (not tPA or venom), and the combination of venom and tPA exposure resulted in significantly greater TMRTG values than any other condition. As for MRTG (middle panel), tPA alone did not decrease this parameter, venom did diminish MRTG compared to control conditions, and the combination of venom and tPA exposure resulted in significantly lesser MRTG values than all other conditions. Lastly, when TTG was considered (bottom panel), both venom and tPA exposure separately and significantly decreased TTG values more than that seen with control conditions; however, the combination of venom and tPA resulted in TTG values significantly smaller than all other conditions. Considered as a whole, these data demonstrate venom-associated enhancement of tPA mediated fibrinolysis as determined by degradation of coagulation kinetics in this in vitro model of simultaneous growth and fibrinolysis.

Assessment of Effects of Iron and CO on Venom-Enhanced Degradation of Coagulation and Fibrinolytic Kinetics.

Figure 4:
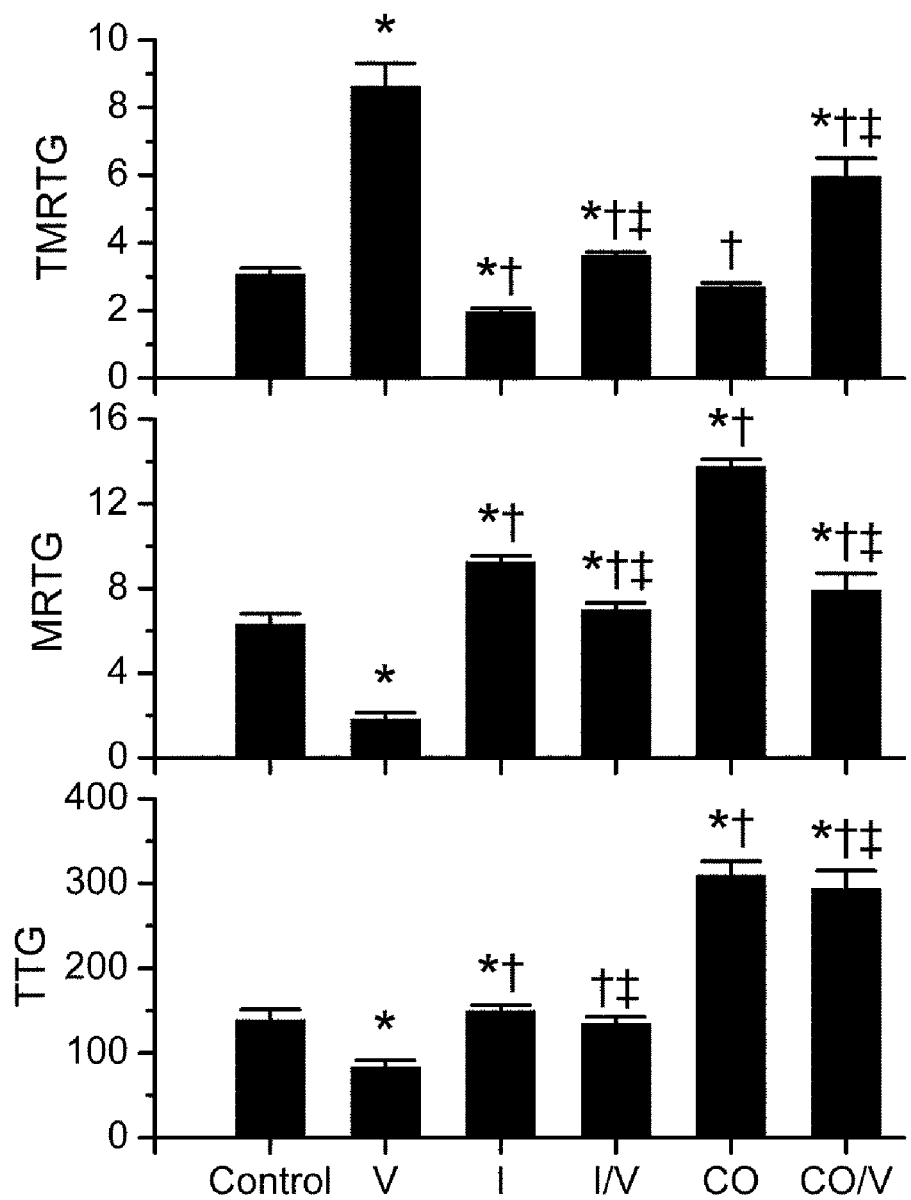
FIG. 4: Individual effects of iron and CO on coagulation kinetics after venom exposure in the presence of tPA. Top panel—TMRTG=time to maximum rate of thrombus generation (min); middle panel—MRTG=maximum rate of thrombus generation (dynes/cm2/sec); bottom panel—TTG=total thrombus generation (dynes/cm2). Control=plasma without additions; V=5 min incubation with 0.5 μg/ml venom; I=preincubation with 10 μM ferric chloride; CO=preincubation with 100 μM CORM-2. *$P<0.05$ vs. control; †$P<0.05$ vs. V; ‡$P<0.05$ vs. matched condition with iron or CO preincubation.

The effects of iron and CO separately on venom-enhanced, tPA mediated degradation of coagulation kinetics are displayed in FIG. 4. Pretreatment with iron resulted in a significant attenuation of the interaction of venom with tPA to prolong TMRTG (top panel), decrease MRTG (middle panel), and decrease TTG (bottom panel) values. Iron pretreatment resulted in significantly lesser TMRTG, greater MRTG and greater TTG values than matched samples without or with venom exposure. With regard to CO pretreatment with CORM-2, significant attenuation of the interaction of venom with tPA to prolong TMRTG (top panel), decrease MRTG (middle panel), and decrease TTG (bottom panel) values. While CO pretreatment did not significantly affect TMRTG in venom naïve samples, TMRTG values were significantly less in venom exposed plasma. In contrast, pretreatment with CO resulted in significantly greater MRTG and greater TTG values than matched samples without or with venom exposure. In sum, both iron and CO separately attenuated venom mediated degradation of coagulation in a tPA induced, fibrinolytic environment.

Figure 5:
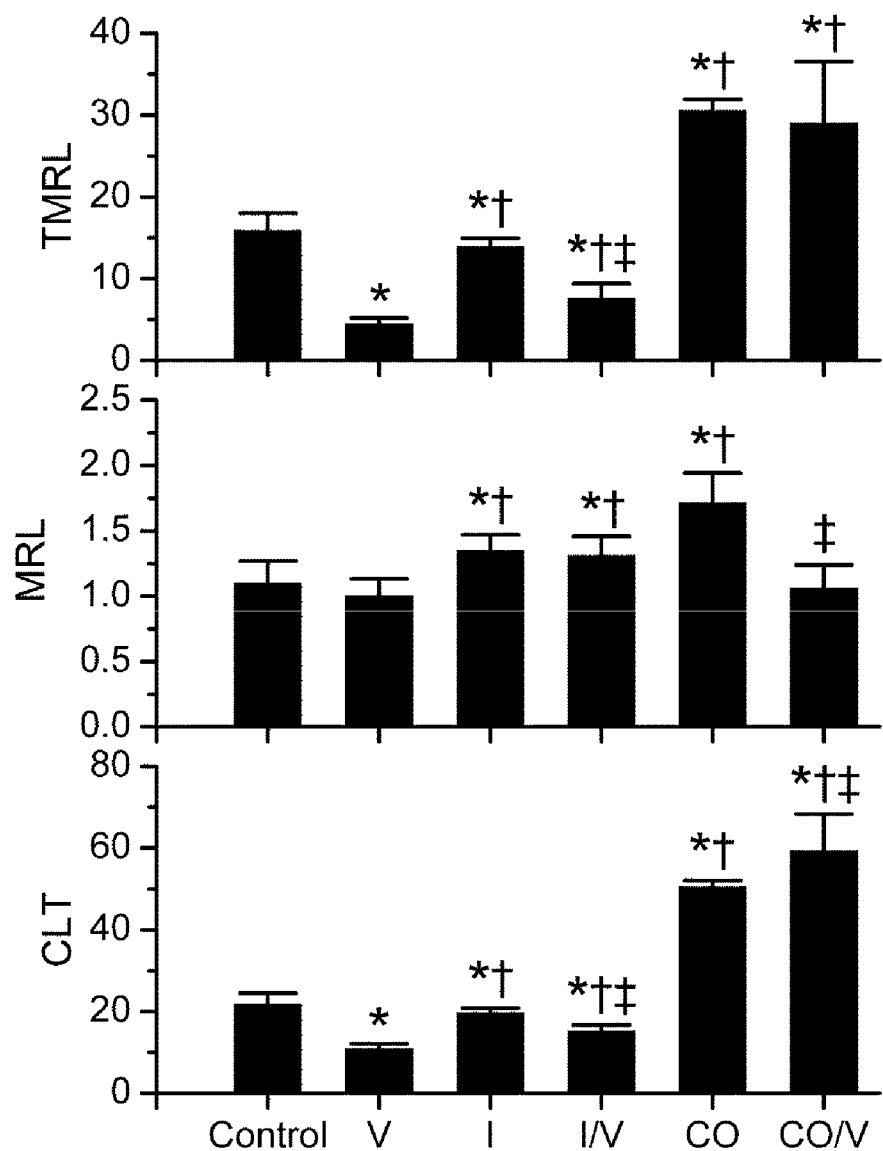
FIG. 5: Individual effects of iron and CO on fibrinolytic kinetics after venom exposure in the presence of tPA. Top panel—TMRL=time to maximum rate of lysis (min); middle panel—MRL=maximum rate of lysis (dynes/cm²/sec); bottom panel—CLT=clot lysis time (min). Control=plasma without additions; V=5 min incubation with 0.5 μg/ml venom; I=preincubation with 10 μM ferric chloride; CO=preincubation with 100 μM CORM-2. *$P<0.05$ vs. control; †$P<0.05$ vs. V; ‡$P<0.05$ vs. matched condition with iron or CO preincubation.

The effects of iron and CO separately on venom-enhanced, tPA mediated degradation of fibrinolytic kinetics are displayed in FIG. 5. Pretreatment with iron resulted in a significant attenuation of the interaction of venom with tPA to diminish TMRL values (top panel) and decrease CLT values (bottom panel), but no significant interaction was observed in the case of MRL values (middle panel). Iron pretreatment resulted in significantly greater TMRL and CLT values than matched samples without or with venom exposure. With regard to MRL, iron pretreatment resulted in significantly greater rates of lysis compared to matched samples without or with venom exposure. As for CO pretreatment, CORM-2 addition resulted in a significant attenuation of the interaction of venom with tPA to diminish TMRL values (top panel) and decrease CLT values (bottom panel); surprisingly, while CORM-2 addition significantly increased MRL, venom exposure reduced MRL to control values, making the two-way ANOVA interaction significant. Lastly, CO pretreatment resulted in significantly greater TMRL and CLT values than matched conditions without or with venom exposure.

Assessment of the Protective Effects of Iron and CO on Coagulation and Fibrinolytic Kinetics after Exposure to Large Concentrations of Venom.

Figure 6:
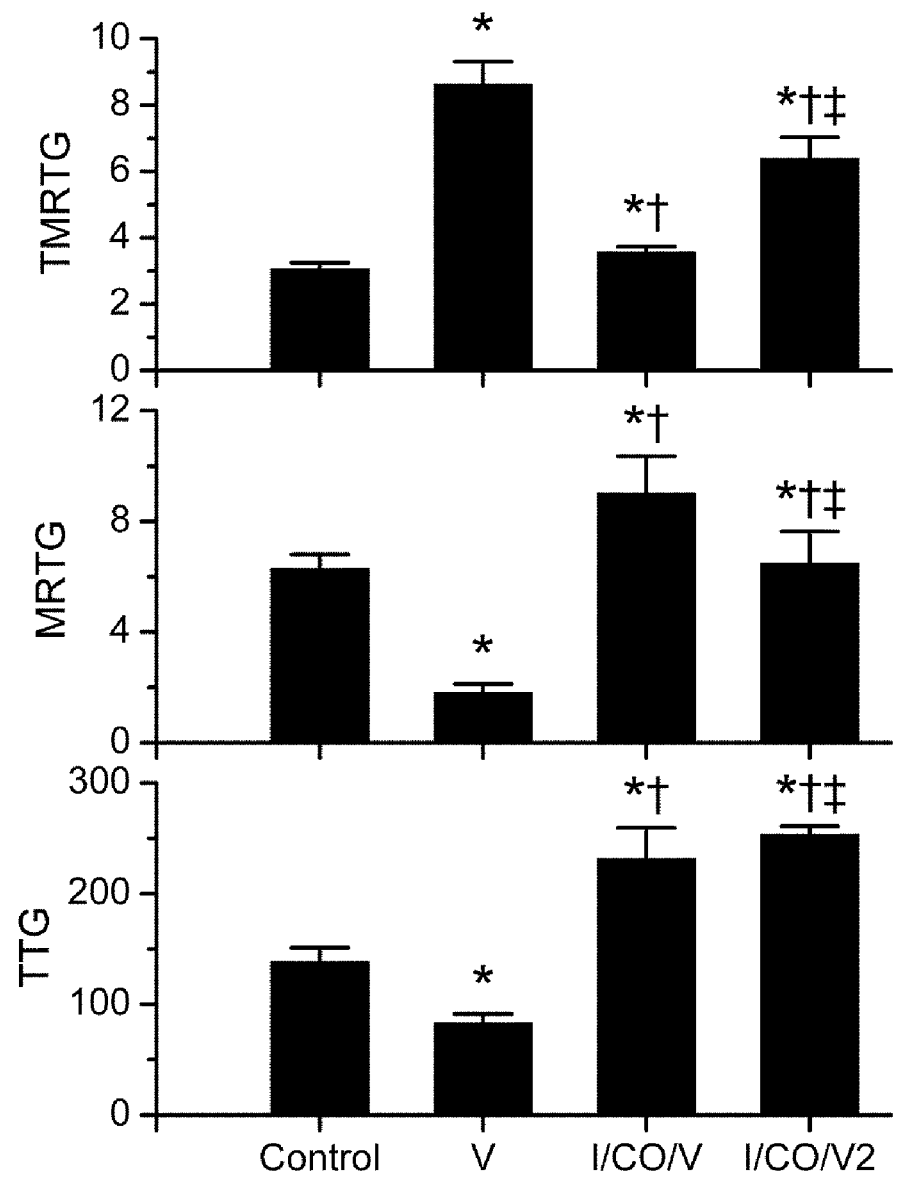
FIG. 6: Combined effects of iron and CO on coagulation kinetics after venom exposure in the presence of tPA. Top panel—TMRTG=time to maximum rate of thrombus generation (min); middle panel—MRTG=maximum rate of thrombus generation (dynes/cm2/sec); bottom panel—TTG=total thrombus generation (dynes/cm2). Control=plasma without additions; V=5 min incubation with 0.5 μg/ml venom; I/CO/V=preincubation with 10 μM ferric chloride and 100 μM CORM-2 followed by 5 min incubation with 0.5 μg/ml venom; I/CO/V2=preincubation with 10 μM ferric chloride and 100 μM CORM-2 followed by 5 min incubation with 2.0 μg/ml venom. *$P<0.05$ vs. control; †$P<0.05$ vs. V; ‡$P<0.05$ vs. I/CO/V.

To assess the combined protection of iron and CO pretreatment against venom mediated degradation of coagulation and fibrinolytic kinetics, plasma had addition of iron and CO and were then exposed to 0.5 and 2.0 µg concentrations of venom. With regard to coagulation kinetics displayed in FIG. 6, iron and CO significantly diminished TMRTG values (top panel) after exposure to 0.5 and 2.0 µg venom compared samples exposed to 0.5 µg venom alone. Further, MRTG (middle panel) and TTG (bottom panel) values were significantly increased in plasma with iron and CO pretreatment and exposure to 0.5 and 2.0 µg venom compared samples exposed to 0.5 µg venom alone. As for the effects of combined iron and CO pretreatment on fibrinolytic kinetics depicted in FIG. 7, plasma exposed to 0.5 µg venom with iron and CO had significantly greater TMRL (top panel), smaller MRL (middle panel), and greater CLT (bottom panel) values compared to plasma exposed to 0.5 g of venom alone. Samples exposed to 2.0 µg of venom after iron and CO pretreatment had TMRL and CLT values greater than to plasma exposed to 0.5 µg of venom alone; however, MRL values were greatest in plasma exposed to 2.0 µg of venom after iron and CO pretreatment. Importantly, considered as a whole, plasma pretreated with iron and CO demonstrated supernormal coagulation and normal fibrinolytic kinetic characteristics after exposure to twice the concentration of venom required to eliminate coagulation altogether.

Figure 7:
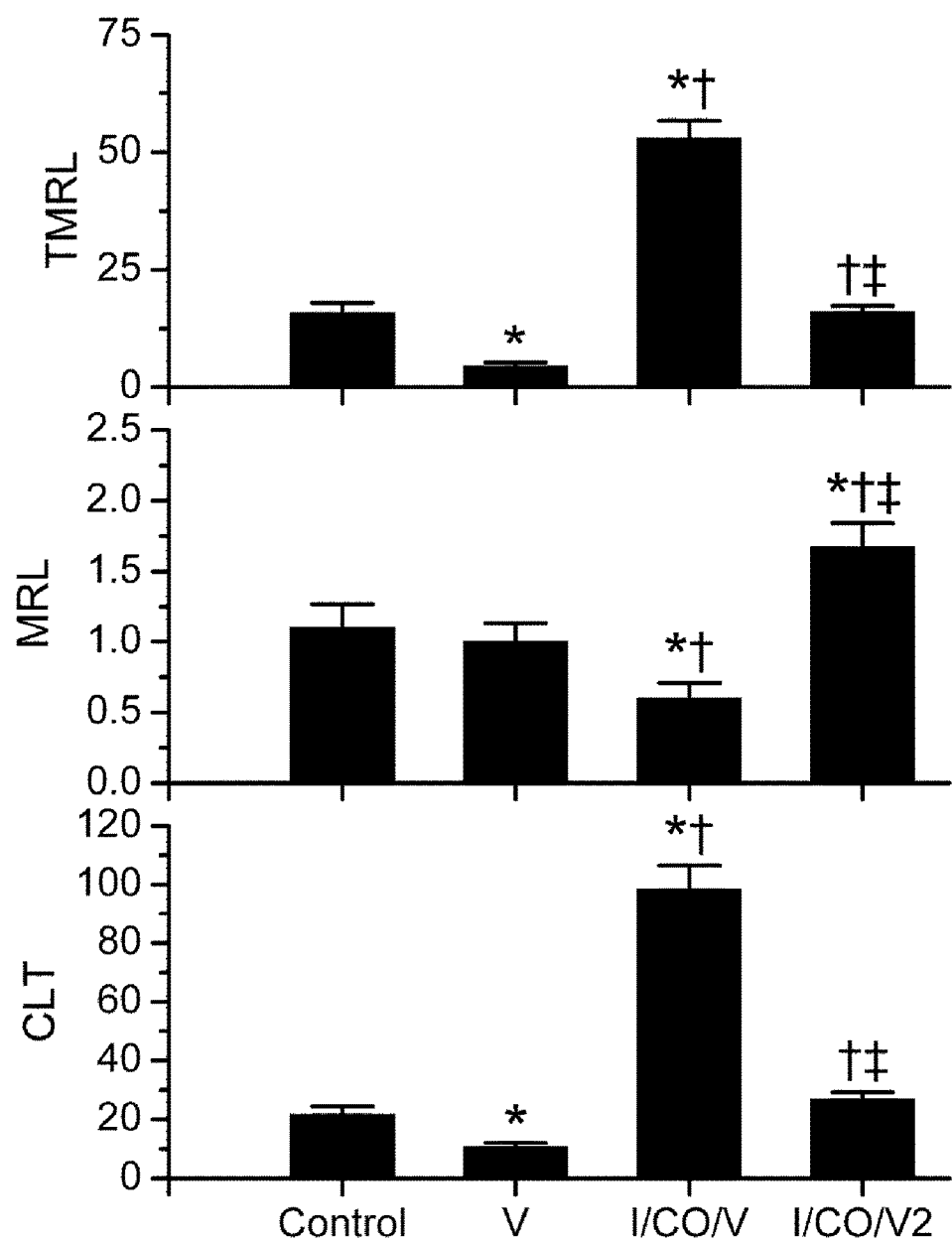
FIG. 7: Combined effects of iron and CO on fibrinolytic kinetics after venom exposure in the presence of tPA. Top panel—TMRL=time to maximum rate of lysis (min); middle panel—MRL=maximum rate of lysis (dynes/cm²/sec); bottom panel—CLT=clot lysis time (min). Control=plasma without additions; V=5 min incubation with 0.5 μg/ml venom; I/CO/V=preincubation with 10 μM ferric chloride and 100 μM CORM-2 followed by 5 min incubation with 0.5 μg/ml venom; I/CO/V2=preincubation with 10 μM ferric chloride and 100 μM CORM-2 followed by 5 min incubation with 2.0 μg/ml venom. *$P<0.05$ vs. control; †$P<0.05$ vs. V; ‡$P<0.05$ vs. I/CO/V.

The primary findings of the present investigation include the observations that C. atrox venom has no intrinsic thrombolytic properties, but instead venom enhanced tPA mediated decreases in coagulation kinetics as well as enhancing tPA mediated fibrinolysis. When the data of the present study are compared with the coagulation and fibrinolytic kinetic profiles observed during progressive plasminogen activation or alpha-2-antiplasmin deficiency (see, Nielsen V G, et al., Blood Coagul Fibrinolysis 2006; 17:75-81; Nielsen V G, Ellis T C. Blood Coagul Fibrinolysis 2007; 18:29-33), and given the previous demonstration of degradation of alpha-2-antiplasmin by C. basiliscus (see, Svoboda Pl, et al., Toxicon 1995; 33:1331-1346), the most likely explanation for the data is that C. atrox venom degraded alpha-2-antiplasmin in the system. Further, while it was not possible with standard endopeptidase approaches to digest alpha-2-antiplasmin to detect attached heme groups secondary to heavy glycosylation of the enzyme (see, Arkebauer M R, et al., Blood Coagul Fibrinolysis 2011; 22:712-719), CO and nitric oxide modulated alpha-2-antiplasmin activity, which is highly suggestive of heme mediated influence. The relevance of these observations is that CO interactions with heme attached to fibrinogen likely changed the structural conformation of the protein, resulting in resistance to venom mediated catalysis; analogously, CO, and perhaps iron, likely interacted with attached heme groups or other sites on alpha-2-antiplasmin and changed its conformation, which, when coupled with extensive glycosylation, resulted in a molecule far more difficult to digest by C. atrox venom. Further, protection of alpha-2-antiplasmin by iron and CO was manifested by the normal TMRL and CLT values of thrombi formed after iron and CO pretreatment followed by exposure to twice the concentration of venom required to prevent coagulation altogether (FIG. 7).

The kinetic basis for the aforementioned conclusions can be ascertained step by step from the data as is subsequently presented. First, as the plasma-based model incorporates tPA into the reaction mix as coagulation commences, it is essentially a simultaneous paradigm of clot growth and lysis. This concurrent lysis of forming clot is observed FIG. 3, as the addition of tPA significantly decreases final clot strength (TTG). Venom addition also decreases clot strength in plasma without tPA addition; however, when tPA and venom are combined, the loss of clot strength is greater than either additive alone, which demonstrates increased lysis either by combined poor fibrin polymer formation secondary to venom mediated fibrinogenolysis or also venom mediated compromise of antifibrinolytic enzymes (e.g., alpha-2-antiplasmin, alpha-2-macroglobulin). In FIG. 4, the addition of either iron or CO markedly decreases or eliminates venom mediated loss of clot strength beyond that observed with tPA addition alone, which could be secondary to improved formation of fibrin polymer formation via effects of iron and CO on fibrinogen, or this effect may be due to preservation of antifibrinolytic enzymes by iron and CO from venom mediated catalysis. These two possibilities are further elucidated by data displayed in FIG. 5; critically, iron and CO delay the onset of maximum rate of lysis (TMRL) in the presence of venom, which is primarily affected by plasmin and alpha-2-antiplasmin interactions in this system (see, Nielsen V G, et al., Blood Coagul Fibrinolysis 2007; 18:29-33). This increase in TMRL is responsible for the significantly greater clot lysis time (CLT) observed in samples exposed to venom after iron or CO addition compared to samples with venom alone, as samples with iron or CO addition have significantly greater maximum rates of lysis (MRL) as seen in the middle and bottom panels of FIG. 5. Since plasmin generation is equivalent across these conditions, an increased antiplasmin activity (alpha-2-antiplasmin, alpha-2-macroglobulin, or both) must be present to account for the delay in onset of fibrinolysis observed after iron and CO pretreatment. This point is further illustrated in FIG. 7, wherein twice the amount of venom required to eliminate coagulation altogether (or 4 fold the concentration of venom tested in the experiments displayed in FIGS. 3, 4 and 5) placed into plasma pretreated with iron and CO resulted in TMRL and CLT values not different from plasma with tPA addition but without venom addition. In sum, the results strongly support not just protection of fibrinogen from venom mediated catalysis by iron and CO addition, but also that protection of antifibrinolytic enzymes (e.g., alpha-2-antiplasmin, alpha-2-macroglobulin) from venom digestion is the major mechanism by which iron and CO attenuate tPA mediated fibrinolysis.

As mentioned in Example I, the amount of iron or CORM-2 used in vitro in the present investigation is significantly less than has been administered in vivo (see, Nielsen V G, et al., Blood Coagul Fibrinolysis 2012; 23:104-107; Kshirsagar, A. V., et al., PLoS ONE 2013; 8:e78930), including in the clinical setting. Using a rabbit ear-bleed model, CORM-2 was injected at a dose of 10 mg/kg (equivalent to 279 µM final concentration) to effect CO mediated resistance to tissue-type plasminogen mediated coagulopathy without adverse effects noted (see, Nielsen V G, et al., Blood Coagul Fibrinolysis 2012; 23:104-107). As for iron, in order to administer a dose that would result in an increase of 10 µM in the circulation, consider the following: assuming a molecular weight of 55.8 atomic mass units for elemental iron, multiply 0.558 µg/ml by 70 ml/kg (estimated blood volume) and by 70 kg (an average weight), for a final result of approximately 2.7 mg of iron. It is clinical practice to infuse up to 100 mg of iron to augment red blood cell production, a value more than 30-fold of the amount required to enhance coagulation (see, Kshirsagar, A. V. et al., PLoS ONE 2013; 8:e78930). In sum, administration of iron and CO in the quantities required to modify alpha-2-antiplasmin to attenuate degradation by *C. atrox* venom may clinically achievable without adverse effects.

Example III

Thousands of individuals experience venomous snake bite annually in the United States (see, O'Neil M E, et al., Wilderness Environ Med 2007; 18:281-7; Seifert S Al, et al., Clin Toxicol (Phila) 2009; 47:327-35; Spiller H A, et al., Am J Emerg Med 2010; 28:780-5; Walter F G, et al., Clin Toxicol (Phila) 2009; 47:663-9), with cottonmouth and copperhead snakes (*Agkistrodon* species) second only to rattlesnakes (*Crotalus* species) as the most identified responsible vipers (see, Seifert S Al, et al., Clin Toxicol (Phila) 2009; 47:327-35). Snake bites by *Agkistrodon* species result in a spectrum of degrees of local and systemic injury (see, Walter F G, et al., South Med J 2012; 105:313-20; Walter F G, et al., South Med J 2014; 107:150-6), including hypofibrinogenemia and coagulopathy (see, Kini R M. Pathophysiol Haemost Thromb 2005; 34:200-4). Of interest, there is heterogeneity in therapeutic approach to envenomation by *Agkistrodon* species in the literature. While administration of antivenom has been recommended to prevent local and circulatory morbidity (see, Spiller H A, et al., Am J Emerg Med 2010; 28:780-5; Lavonas E J, et al., Ann Emerg Med 2004; 43:200-6), there is debate concerning the need to serially assess patient coagulation status (see, Ali A J, et al., Ann Emerg Med 2015; 65:404-9; Evans C S, et al., Ann Emerg Med 2015; 65:467-8) or even administer antivenom at all (see, Walker J P, Morrison R L. J Am Coll Surg 2011; 212:470-4). Nevertheless, significant morbidity and occasional mortality occurs after envenomation by *Agkistrodon* species (see, Walter F G, et al., South Med J 2012; 105: 313-20; Walter F G, et al., South Med J 2014; 107:150-6; Zad O, et al., Am J Emerg Med 2009; 27:377.e1-377.e5).

Cottonmouth and copperhead snakes in North American generally possess venom that is fibrinogenolytic (see, Hahn B S, et al., Toxicon 1995; 33:929-41; Bajwa S S, et al., Toxicon 1982; Jia Y, et al., Toxicon 2009; 54:233-43; Shimizu Al, et al., Toxicon 1987; 25:751-7; Johnson E K, et al., Int J Biochem 1993; 25:267-78; Moran J B, Geren C R. Biochim Biophys Acta 1981; 659:161-8). Intact venom or purified metalloproteinases typically cleave the A($\alpha$)-chain and the B($\beta$)-chain of fibrinogen, resulting hypofibrinogenemia state and decreased coagulation (see, Hahn B S, et al., Toxicon 1995; 33:929-41; Bajwa S S, et al., Toxicon 1982; Jia Y, et al., Toxicon 2009; 54:233-43; Shimizu Al, et al., Toxicon 1987; 25:751-7; Johnson E K, et al., Int J Biochem 1993; 25:267-78; Moran J B, Geren C R. Biochim Biophys Acta 1981; 659:161-8). While antivenom can bind and inactivate these enzymes, another approach to maintain circulating fibrinogen may be to render it less vulnerable to venom mediated attack that is not snake species-specific. One such strategy could involve changing the structural configuration of fibrinogen with recently described interactions with iron and carbon monoxide (CO). Specifically, it has been have revealed that plasmatic fibrinogen exposed to iron and CO forms thrombi that are structurally different from plasma without such exposures, and coagulation commences earlier, with greater formation velocity and final clot strength compared to clots that are iron and CO naïve (see, Nielsen V G, Pretorius E. Blood Coagul Fibrinolysis 2014; 25: 695-702). CO binds to heme(s) bound to fibrinogen (see, Nielsen V G, et al., Blood Coagul Fibrinolysis 2011; 22:443-7), iron and heme have been found to bind to fibrinogen by other investigators (see, Orino K. Biometals 2013; 26:789-94), with chelation of iron noted to reverse both structural and coagulation kinetic changes in plasma thrombi (see, Nielsen V G, Pretorius E. Blood Coagul Fibrinolysis 2014; 25:845-50). Iron and CO enhance fibrinogen by separate mechanisms; iron decreases the time to onset of coagulation and increases the velocity of clot formation without affecting final clot strength, whereas CO increases the velocity of clot formation and increases clot strength without affecting the time to onset of coagulation (see, Nielsen V G, Pretorius E. Blood Coagul Fibrinolysis 2014; 25: 695-702). When combined, the velocity of clot formation increases in an additive manner by both these agents (see, Nielsen V G, Pretorius E. Blood Coagul Fibrinolysis 2014; 25: 695-702). Also of interest, exposure to CO resulted in the inability to recover significant portions of the γ chain after endopeptidase treatment of purified fibrinogen during mass spectroscopic analysis (see, Nielsen V G, et al., Blood Coagul Fibrinolysis 2011; 22:443-7), indirect evidence of molecular conformational change of fibrinogen. Lastly, the pretreatment of human plasma with iron and CO has recently been demonstrated to markedly attenuate the fibrinogenolytic effects of *Crotalus atrox* venom, which serves as a proof of concept (see, Nielsen V G, Boyer L V. Iron and carbon monoxide attenuate degradation of plasmatic coagulation by *Crotalus atrox* venom. Blood Coagul Fibrinolysis, in press). Taken as a whole, these data suggested that it may be possible to change the three-dimensional configuration of fibrinogen with iron and CO such that thrombin could interact with it as an enhanced substrate, but perhaps fibrinogenase activity in snake venom could not. The hypothesis of the following experiments was that pretreatment of plasma with iron and CO may attenuate the ability of the venom of a selection of six *Agkistrodon* species to catalyze fibrinogen and compromise coagulation kinetics as determined by thrombelastography.

Pooled normal human plasma (George King Bio-Medical, Overland Park, Kans., USA) anticoagulated with sodium citrate (9 parts blood to 1 part 0.105M sodium citrate) stored at −80° C. was utilized in all subsequently described experiments. The six species of snake tested and associated references that document fibrinogenolytic activity are depicted in Table 1. Two-hundred mg of lyophilized snake venom obtained from each species was obtained from the National Natural Toxins Research Center at Texas A&M University, Kingsville, Tex., USA. The six venom samples were individually reconstituted in calcium-free phosphate buffered saline (PBS, Sigma-Aldrich, Saint Louis, Mo., USA) at a concentration of 50 mg/ml, aliquoted, and stored at −80° C. until experimentation.

TABLE 1

*Agkistrodon* species studied.

| Common Name | Species |
|---|---|
| Southern Copperhead | *Agkistrodon contortrix contortrix* |
| Trans-Pecos Copperhead | *Agkistrodon contortrix pictigaster* |
| Broad-Banded Copperhead | *Agkistrodon contortrix laticinctus* |
| Northern Copperhead | *Agkistrodon contortrix mokasen* |
| Eastern Cottonmouth | *Agkistrodon piscivorus piscivorus* |
| Western Cottonmouth | *Agkistrodon piscivorus leucostoma* |

Plasma was rapidly thawed at 37° C. on the day of experimentation. Plasma had 1% additions of ferric chloride ($FeCl_3$, 99.9% pure, Sigma-Aldrich, Saint Louis, Mo., USA) in phosphate buffered saline) or CORM-2 (tricarbonyldichlororuthenium (II) dimer, a CO releasing molecule, Sigma-Aldrich, Saint Louis, Mo., USA) dissolved in dimethyl sulfoxide (Sigma-Aldrich, Saint Louis, Mo., USA). The final concentrations of $FeCl_3$ and CORM-2 were 0-10 µM and 0-100 µM, respectively; these concentrations are associated with nearly maximal augmenting effects on coagulation kinetics (see, Nielsen V G, Pretorius E. Blood Coagul Fibrinolysis 2014; 25: 695-702). Plasma was exposed to these various agents for at least 5 min prior to placement into plastic thrombelastographic cups (Haemonetics Inc., Braintree, Mass., USA).

The final volume for all subsequently described plasma sample mixtures was 359.4 µl. Sample composition consisted of 326 µl of plasma; 10 µl of tissue factor reagent (0.1% final concentration in distilled water; Diagnostica Stago S.A.S., Asnieres sur Seine, France) and 3.4 µl of PBS or venom (final concentration 0.5 pig/ml). In pilot studies, the concentration of venom to be used from each specific snake was determined after 5 min of incubation at 37° C.; the final concentration to be used had to markedly (50%) effect one or more coagulation kinetic parameter values (e.g., 100% increase in time to maximum rate of thrombus formation, 50% decrease in the speed of clot formation) before the addition of calcium to commence coagulation. The aforementioned plasma and venom mixtures were placed in a disposable cup in a computer-controlled Thrombelastograph® hemostasis system (Model 5000, Haemonetics Inc., Braintree, Mass., USA) and incubated for 5 min at 37° C., with addition of 20 µl of 200 mM $CaCl_2$ as the last step to initiate clotting. Data were collected at 37° C. for 15 min. The following elastic modulus-based parameters previously described (see, Nielsen V G, Pretorius E. Blood Coagul Fibrinolysis 2014; 25: 695-702; Nielsen V G, et al., Blood Coagul Fibrinolysis 2011; 22:443-7; Nielsen V G, Pretorius E. Blood Coagul Fibrinolysis 2014; 25:845-50) were determined: time to maximum rate of thrombus generation (TMRTG): this is the time interval (min) observed prior to maximum speed of clot growth; maximum rate of thrombus generation (MRTG): this is the maximum velocity of clot growth observed (dynes/$cm^2$/sec); and total thrombus generation (TTG, dynes/$cm^2$), the final viscoelastic resistance observed after clot formation.

Data are presented as mean+SD. Each condition was represented by n=6 replicate experiments. A commercially available statistical program was used for one-way analysis of variance followed by Holm-Sidak post hoc analyses (SigmaStat 3.1, Systat Software, Inc., San Jose, Calif., USA). Graphics depicting TMRTG, MRTG and TTG data were generated with a commercially available program (OrigenPro 7.5, OrigenLab Corporation, Northampton, Mass., USA).

Data generated by exposure of plasma to no additives (control), venom (V) addition, or iron and CORM-2 prior to venom (Fe/CO/V) addition, are displayed in for the six snakes in FIGS. 8-13. Separate paragraphs of the findings of each species will be subsequently presented to improve clarity.

*Agkistrodon contortrix contortrix.*

Figure 8:
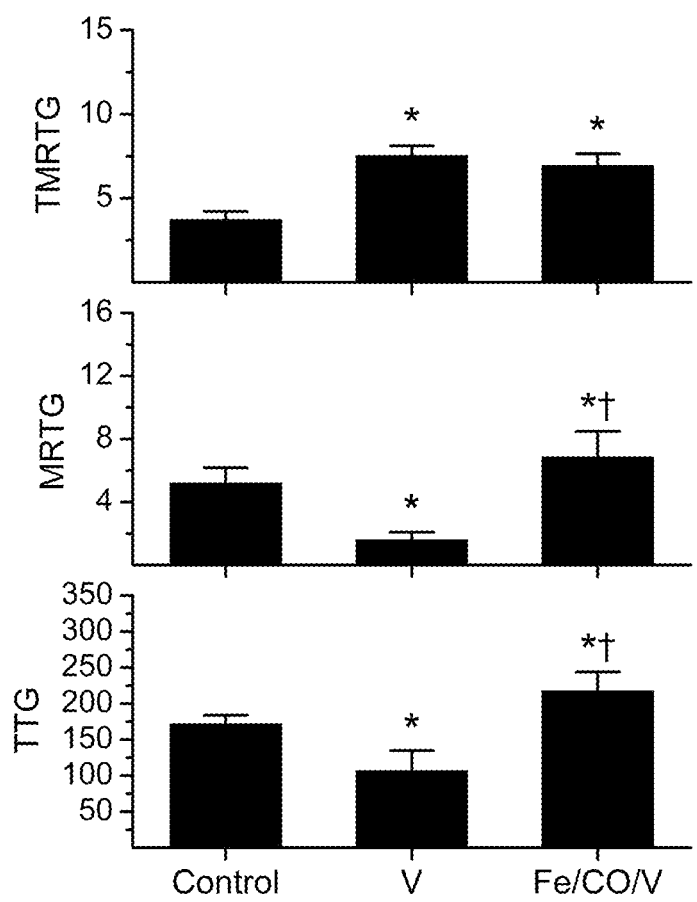
FIG. 8: Effect of *Agkistrodon contortrix contortrix* venom, iron and carbon monoxide exposure on coagulation in human plasma. Data are presented as mean+SD. TMRTG=time to maximum rate of thrombus generation (min); MRTG=maximum rate of thrombus formation (dynes/cm²/sec); TTG=total thrombus generation (dynes/cm²); Control=additive naïve plasma; V=venom added, 5 min incubation prior to calcium addition; Fe/CO/V=plasma exposed to ferric chloride and CORM-2 prior to 5 min incubation with venom before calcium addition. *$P<0.05$ vs. Control; †$P<0.05$ vs. V.

The concentration of venom used was 6 µg/ml. As can be seen in FIG. 8, exposure to venom significantly increased TMRTG (top panel), decreased MRTG (middle panel), and decreased TTG (bottom panel). Pretreatment with iron and CO did not significantly affect the effects of venom on TMRTG, but did significantly increase MRTG and TTG values when compared to control plasma or venom exposed plasma.

*Agkistrodon contortrix pictigaster.*

Figure 9:
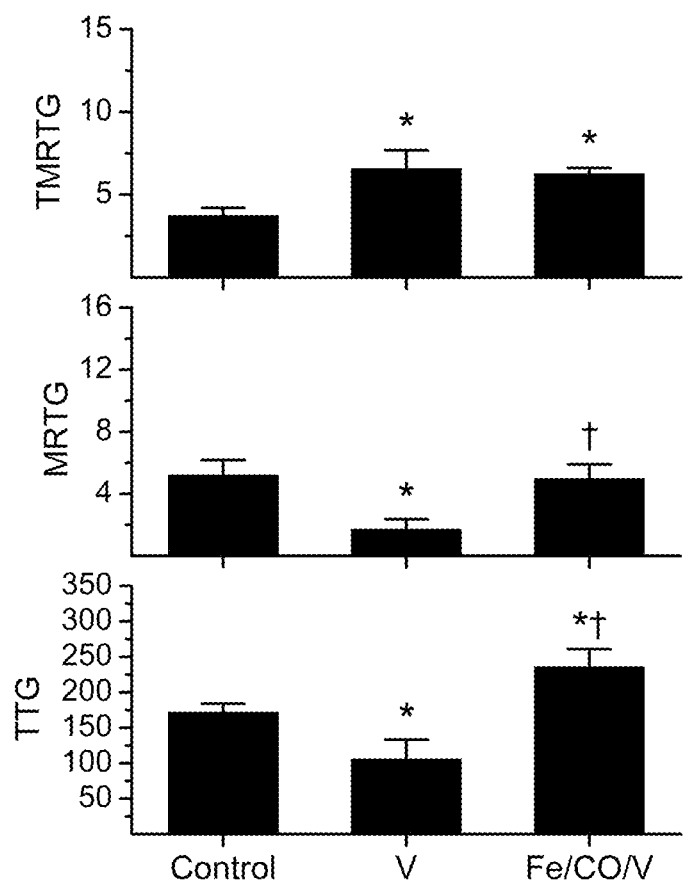
FIG. 9: Effect of *Agkistrodon contortrix pictigaster* venom, iron and carbon monoxide exposure on coagulation in human plasma. Data are presented as mean+SD. TMRTG=time to maximum rate of thrombus generation (min); MRTG=maximum rate of thrombus formation (dynes/cm²/sec); TTG=total thrombus generation (dynes/cm²); Control=additive naïve plasma; V=venom added, 5 min incubation prior to calcium addition; Fe/CO/V=plasma exposed to ferric chloride and CORM-2 prior to 5 min incubation with venom before calcium addition. *$P<0.05$ vs. Control; †$P<0.05$ vs. V.

The concentration of venom used was 11 µg/ml. As can be seen in FIG. 9, exposure to venom significantly increased TMRTG (top panel), decreased MRTG (middle panel), and decreased TTG (bottom panel). Pretreatment with iron and CO did not significantly affect the effects of venom on TMRTG, but did significantly increase MRTG values compared to venom exposed plasma. In the case of clot strength, iron and CO pretreatment resulted in TTG values significantly greater than control plasma or venom exposed plasma values.

*Agkistrodon contortrix laticinctus.*

Figure 10:
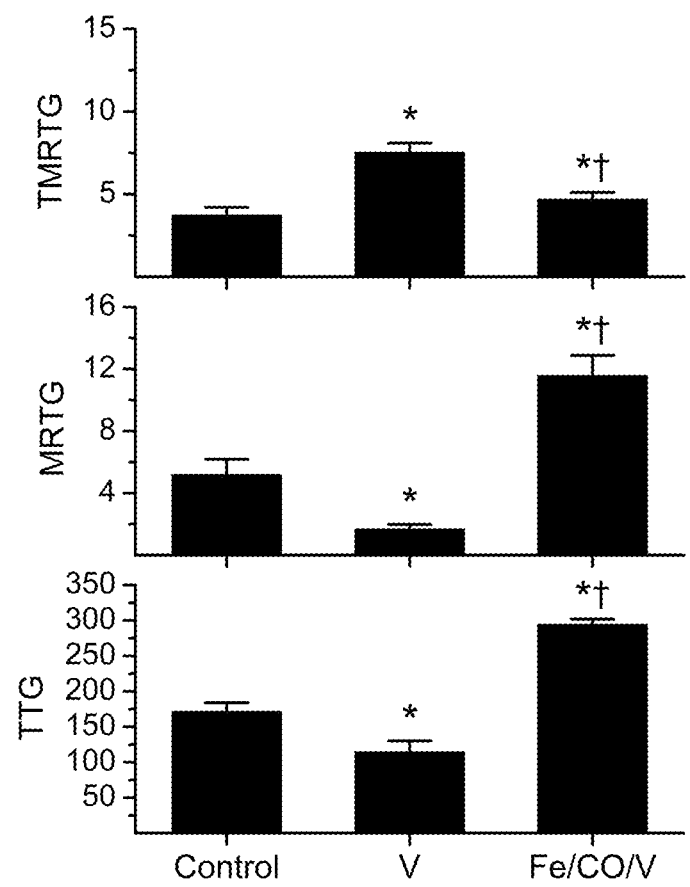
FIG. 10: Effect of *Agkistrodon contortrix laticinctus* venom, iron and carbon monoxide exposure on coagulation in human plasma. Data are presented as mean+SD. TMRTG=time to maximum rate of thrombus generation (min); MRTG=maximum rate of thrombus formation (dynes/cm²/sec); TTG=total thrombus generation (dynes/cm²); Control=additive naïve plasma; V=venom added, 5 min incubation prior to calcium addition; Fe/CO/V=plasma exposed to ferric chloride and CORM-2 prior to 5 min incubation with venom before calcium addition. *$P<0.05$ vs. Control; †$P<0.05$ vs. V.

The concentration of venom used was 10 µg/ml. As can be seen in FIG. 10 exposure to venom significantly increased TMRTG (top panel), decreased MRTG (middle panel), and decreased TTG (bottom panel). Pretreatment with iron and CO did affect the effects of venom on TMRTG, resulting in significantly smaller values when compared with venom exposed plasma values but still larger than control plasma values. Pretreatment with iron and CO resulted in significantly greater MRTG and TTG values when compared to control plasma or venom exposed plasma.

*Agkistrodon contortrix mokasen.*

Figure 11:
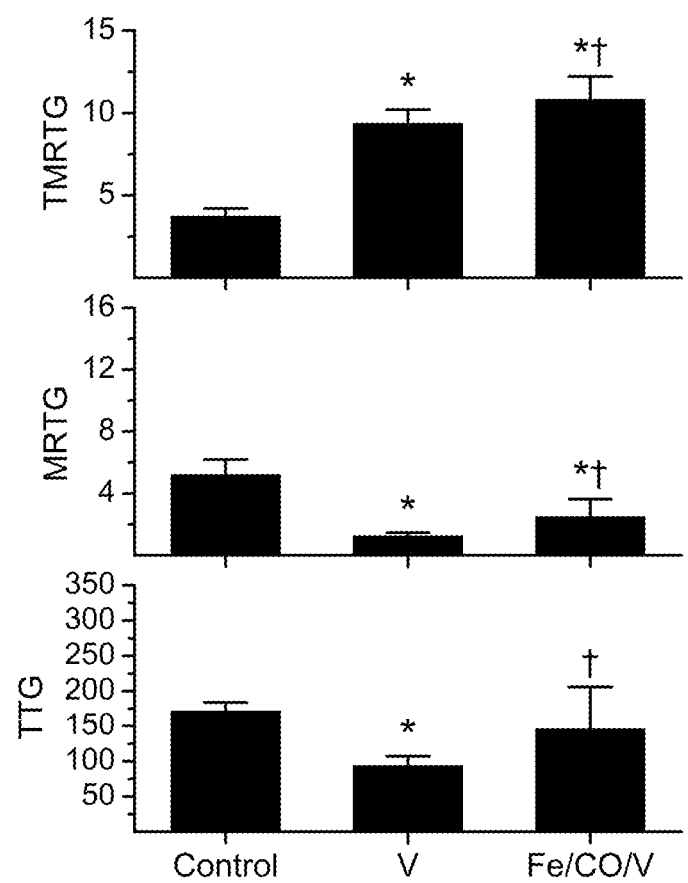
FIG. 11: Effect of *Agkistrodon contortrix mokasen* venom, iron and carbon monoxide exposure on coagulation in human plasma. Data are presented as mean+SD. TMRTG=time to maximum rate of thrombus generation (min); MRTG=maximum rate of thrombus formation (dynes/cm²/sec); TTG=total thrombus generation (dynes/ cm$^2$); Control=additive naïve plasma; V=venom added, 5 min incubation prior to calcium addition; Fe/CO/V=plasma exposed to ferric chloride and CORM-2 prior to 5 min incubation with venom before calcium addition. *P<0.05 vs. Control; †P<0.05 vs. V.

The concentration of venom used was 4 µg/ml. As can be seen in FIG. 11, exposure to venom significantly increased TMRTG (top panel), decreased MRTG (middle panel), and decreased TTG (bottom panel). With regard to TMRTG, iron and CO pretreatment of plasma resulted in values significantly greater than venom exposed plasma or control plasma. However, pretreatment with iron and CO significantly increased MRTG values compared to venom exposed plasma; but these values were still significantly less than control plasma. Lastly, iron and CO addition resulted in TTG values significantly greater than venom exposed plasma, but not different from control plasma values.

*Agkistrodon piscivorus piscivorus.*

The concentration of venom used was 0.5 µg/ml. As can be seen in FIG. 12, exposure to venom significantly increased TMRTG (top panel), decreased MRTG (middle panel), and decreased TTG (bottom panel). With regard to TMRTG, iron and CO pretreatment resulted in values not significantly different from control plasma but significantly different from venom exposed plasma. As for MRTG and TTG, iron and CO pretreatment resulted in values significantly greater than control plasma or venom exposed plasma.

*Agkistrodon piscivorus leucostoma.*

The concentration of venom used was 1 µg/ml. As can be seen in FIG. 13, exposure to venom significantly increased TMRTG (top panel), decreased MRTG (middle panel), and decreased TTG (bottom panel). TMRTG values were significantly greater than control plasma in plasma with iron and CO pretreatment exposed to venom, but these values were significantly less than venom exposed plasma values. With regard to MRTG and TTG, iron and CO pretreatment resulted in values significantly greater than control plasma or venom exposed plasma.

Lastly, Table 2 provides a facile reference of the effects on plasmatic coagulation of the individual venoms and response to iron and CO pretreatment.

TABLE 2

Effects of *Agkistrodon* species venom on thrombelastographic parameters with or without iron and CO addition.

| Species | No Additions | | | Iron and CO Added | | |
|---|---|---|---|---|---|---|
| | TMRTG | MRTG | TTG | TMRTG | MRTG | TTG |
| *Agkistrodon contortrix contortrix* | ↑ | ↓ | ↓ | NC | ↑ | ↑ |

TABLE 2-continued

Effects of *Agkistrodon* species venom on thrombelastographic parameters with or without iron and CO addition.

| | No Additions | | | Iron and CO Added | | |
|---|---|---|---|---|---|---|
| Species | TMRTG | MRTG | TTG | TMRTG | MRTG | TTG |
| *Agkistrodon contortrix pictigaster* | ↑ | ↓ | ↓ | NC | ↑ | ↑ |
| *Agkistrodon contortrix laticinctus* | ↑ | ↓ | ↓ | ↓ | ↑ | ↑ |
| *Agkistrodon contortrix mokasen* | ↑ | ↓ | ↓ | ↑ | ↑ | ↑ |
| *Agkistrodon piscivorus piscivorus* | ↑ | ↓ | ↓ | ↓ | ↑ | ↑ |
| *Agkistrodon piscivorus leucostoma* | ↑ | ↓ | ↓ | ↓ | ↑ | ↑ |

TMRTG = time to maximum rate of thrombus generation;
MRTG = maximum rate of thrombus generation;
TTG = total thrombus generation.
In the category of No Additions, ↑ = significant increase secondary to venom exposure compared to venom naive plasma, and ↓ = significant decrease secondary to venom exposure compared to venom naive plasma. In the category of Iron and CO Added, ↑ = significant increase secondary to pretreatment with iron and CO prior to venom exposure compared to venom exposed plasma, ↓ = significant decrease secondary to pretreatment with iron and CO prior to venom exposure compared to venom exposed plasma, and NC = no change secondary to pretreatment with iron and CO prior to venom exposure compared to venom exposed plasma.

The major findings of this investigation include the documentation that plasmatic coagulation kinetics are degraded by the fibrinogenolytic activity from venom of all six snakes tested. However, the response to iron and CO pretreatment on venom-compromised coagulation varied between species. When placed in order of greatest to least coagulation kinetic parameters improved by iron an CO pretreatment, the following hierarchy is observed: *Agkistrodon piscivorus piscivorus>Agkistrodon piscivorus leucostoma=Agkistrodon contortrix laticinctus>Agkistrodon contortrix contortrix>Agkistrodon contortrix pictigaster>Agkistrodon contortrix mokasen*. Considered as a whole, these unique observations support the concept that the molecular targets of thrombin and the various venoms on fibrinogen are distinct from one another, and that modification of fibrinogen with iron and CO may result in a positive, neutral or negative effect on coagulation depending on the species of snake tested.

The amount of iron and CORM-2 used in vitro in the present investigation is significantly less than has been administered in vivo (see, Nielsen V G, et al., Blood Coagul Fibrinolysis 2012; 23:104-725; Kshirsagar A V, et al., PLoS ONE 2013; 8:e78930) including in the clinical setting. Using a rabbit ear-bleed model, CORM-2 was injected at a dose of 10 mg/kg (equivalent to 279 µM final concentration) to effect CO mediated resistance to tissue-type plasminogen mediated coagulopathy without adverse effects noted (see, Nielsen V G, et al., Blood Coagul Fibrinolysis 2012; 23:104-725). As for iron, in order to administer a dose that would result in an increase of µM in the circulation, consider the following: assuming a molecular weight of 55.8 atomic mass units for elemental iron, multiply 0.558 µg/ml by 70 ml/kg (estimated blood volume) and by 70 kg (an average weight), for a final result of approximately 2.7 mg of iron. It is clinical practice to infuse up to 100 mg of iron to augment red blood cell production, a value more than 30-fold of the amount required to enhance coagulation (see, Kshirsagar A V, et al., PLoS ONE 2013; 8:e78930). In sum, administration of iron and CO in the quantities required to modify fibrinogen to attenuate degradation by fibrinogenolytic activity in the venom of the snakes tested may be clinically achievable without adverse effects.

These findings also have implications for diagnostic data collection of snakebite victims. Fibrinogen concentrations are typically measured from citrated plasma, and if a venom's activity is calcium-independent, then the concentration of fibrinogen may be artificially decreased if there is a prolonged time from collection to analysis in the clinical laboratory. In other words, one might expect that blood samples obtained from patients bitten by any of these six *Agkistrodon* species may have reduced fibrinogen concentrations, especially if some delay in centrifugation or other processing steps prolonged the time to analysis. In sum, the data of the present investigation should also give clinical laboratorians concern when considering the diagnostic evaluation of plasma fibrinogen concentration for the care of snakebite patients.

The preponderance of data available support the paradigm of fibrinogenolytic venoms catalyzing the A($\alpha$)-chain and the B($\beta$)-chain of fibrinogen or sequentially (see, Hahn B S, et al., Toxicon 1995; 33:929-41; Bajwa S S, et al., Toxicon 1982; 20:427-32; Jia Y, et al., Toxicon 2009; 54:233-43; Shimizu Al, et al., Toxicon 1987; 25:751-7; Johnson E K, et al., Int J Biochem 1993; 25:267-78; Moran J B, et al., Biochim Biophys Acta 1981; 659:161-8). While most snakes with this type of venom usually digest the A($\beta$)-chain before the B($\beta$)-chain, *Agkistrodon contortrix contortrix* (Southern copperhead) venom instead digests the B($\beta$)-chain before the A($\alpha$)-chain (see, Shimizu Al, et al., Toxicon 1987; 25:751-7). However, digestion of the $\gamma$ chain of fibrinogen by this type of venom has not been described, and the data of the present study support this concept. Specifically, while TMRTG and MRTG are most compromised by these fibrinogenolytic venoms (FIGS. 8-13), TTG is less affected, and TTG is best preserved after iron and CO are added to plasma. Conceptually, the initiation and velocity of clot formation is most dependent on thrombin mediated catalysis of the A($\alpha$)-chain and the B($\beta$)-chain of fibrinogen (TMRTG and MRTG), and clot strength is determined by crosslinking of the $\gamma$ chain (TTG). In sum, the loss of clot strength in the model is most likely due to loss of the concentration of functional fibrinogen (recognizable and catalyzed by thrombin) by venom mediated loss of A($\beta$)-chain and the B($\beta$)-chain, not loss of $\gamma$ chain function.

Example IV

Snake venom can have many deleterious effects, which include enzymatic degradation of the coagulation system (see, Kini R M. Pathophysiol Haemost Thromb 2005; 34:200-204; Markland Jr. F S, Swenson S. Toxicon 2013; 62:3-18). The enzymes involved are typically serine proteases or metalloproteinases (see, Kini R M. Pathophysiol Haemost Thromb 2005; 34:200-204; Markland Jr. F S, Swenson S. Toxicon 2013; 62:3-18). In particular, a variety of rattlesnake species found in populous regions throughout North America have defibrinogenating venoms that contain thrombin-like activity (see, Kini R M. Pathophysiol Haemost Thromb 2005; 34:200-204). However, unlike thrombin, such venom does not activate factor XIII, with a resultant weak, friable clot (see, Kini R M. Pathophysiol Haemost Thromb 2005; 34:200-204). In particular, the venom of the timber rattlesnake (*Crotalus horridus*) causes a disseminated intravascular coagulation-like coagulopathy (see, Hasiba U, et al., N Engl J Med 1975; 292:505-7), whereas the venoms of the Eastern diamondback rattlesnake (*Crotalus adamanteus*) (see, Van Mierop L H, et al., J Fla Med Assoc 1980; 67:21-27; Kitchens Cl, et al., J Med Toxicol 2008; 4:180-183) and Southern Pacific rattlesnake (*Crotalus oreganus helleri*) (see, Bush S P, et al., Ann Emerg Med 2002; 40:619-624) primarily result in severe, sometimes fatal hypofibrinogenemia. All of these snakes have well characterized, thrombin-like activity in their venoms (see, Shu Y Y, et al., Biochim Biophys Acta 1983; 748:236-244; Kitchens C S, et al., Am J Hematol 1983; 14:345-353; Bajwa S S, et al., Toxicon 1981; 19:53-59; Salazar A M, et al., Comp Biochem Physiol C Toxicol Pharmacol 2009; 149:307-316; Sunagar K, et al., J Proteomics 2014; 99:68-83). In sum, envenomation by these particular rattlesnakes can be successfully treated with timely administration of antivenom, but serious injury, coagulopathy and death still occur (see, Walter F G, et al., Clin Toxicol (Phila) 2009; 47:663-669; Hasiba U, et al., N Engl J Med 1975; 292:505-7; Van Mierop L H, et al., J Fla Med Assoc 1980; 67:21-27; Kitchens Cl, et al., J Med Toxicol 2008; 4:180-183; Bush S P, et al., Ann Emerg Med 2002; 40:619-624).

While antibodies to venom compounds and enzymes in antivenom can be lifesaving, the particular antivenom administered may not be effective in all cases of envenomation, and even the same species of rattlesnake may express different types of venom depending on location (see, Kitchens Cl, et al., J Med Toxicol 2008; 4:180-183; Bush S P, et al., Ann Emerg Med 2002; 40:619-624; Salazar A M, et al., Comp Biochem Physiol C Toxicol Pharmacol 2009; 149:307-316; Sunagar K, et al., J Proteomics 2014; 99:68-83). Another approach, at least for preserving circulating fibrinogen, may be to somehow render it less vulnerable to venom mediated enzymatic attack that is not snake species-specific. One such strategy could involve changing the structural configuration of fibrinogen with recently described interactions with iron and carbon monoxide (CO). Specifically, recent investigations have revealed that plasmatic fibrinogen exposed to iron and CO forms thrombi that are structurally different from plasma without such exposures, and coagulation commences earlier, with greater formation velocity and final clot strength compared to clots that are iron and CO naïve (see, Nielsen V G, et al., Blood Coagul Fibrinolysis 2014; 25:695-702). CO binds to heme(s) bound to fibrinogen (see, Nielsen V G, et al., Blood Coagul Fibrinolysis 2011; 22:443-447), and iron and heme have been found to bind to fibrinogen (see, Orino K. Biometals 2013; 26:789-794), with chelation of iron noted to reverse both structural and coagulation kinetic changes in plasma thrombi (see, Nielsen V G, Pretorius E. et al., Blood Coagul Fibrinolysis 2014; 25:845-850). Iron and CO enhance fibrinogen by separate mechanisms; iron decreases the time to onset of coagulation and increases the velocity of clot formation without affecting final clot strength, whereas CO increases the velocity of clot formation and increases clot strength without affecting the time to onset of coagulation (see, Nielsen V G, et al., Blood Coagul Fibrinolysis 2014; 25:695-702). When combined, the velocity of clot formation increases in an additive manner by both these agents (see, Nielsen V G, et al., Blood Coagul Fibrinolysis 2014; 25:695-702). Also of interest, exposure to CO resulted in the inability to recover significant portions of the γ chain after endopeptidase treatment of purified fibrinogen during mass spectroscopic analysis (see, Nielsen V G, et al., Blood Coagul Fibrinolysis 2011; 22:443-447), indirect evidence of molecular conformational change of fibrinogen. Taken as a whole, these data suggested that it may be possible to change the three-dimensional configuration of fibrinogen with iron and CO such that thrombin could interact with it as an enhanced substrate, but perhaps thrombin-like activity in snake venom could not.

The hypothesis of the following experiments was that pretreatment of plasma with iron and CO may attenuate the ability of the venom of the aforementioned rattlesnake species to catalyze fibrinogen.

Chemicals and Reagents.

Pooled normal human plasma (George King Bio-Medical, Overland Park, Kans., USA) anticoagulated with sodium citrate (9 parts blood to 1 part 0.105M sodium citrate) stored at −80° C. was utilized in all subsequently described experiments. Two-hundred mg of lyophilized timber rattlesnake, Eastern diamondback rattlesnake, and Southern Pacific rattlesnake venom was obtained from the National Natural Toxins Research Center at Texas A&M University, Kingsville, Tex., USA. Venom was reconstituted in calcium-free phosphate buffered saline (PBS, Sigma-Aldrich, Saint Louis, Mo., USA) at a concentration of 50 mg/ml, aliquoted, and stored at −80° C. until experimentation.

Iron and CO Pretreatment.

Plasma was rapidly thawed at 37° C. on the day of experimentation. Plasma had 1% additions of ferric chloride ($FeCl_3$, 99.9% pure, Sigma-Aldrich, Saint Louis, Mo., USA) in phosphate buffered saline) or CORM-2 (tricarbonyldichlororuthenium (II) dimer, a CO releasing molecule, Sigma-Aldrich, Saint Louis, Mo., USA) dissolved in dimethyl sulfoxide (Sigma-Aldrich, Saint Louis, Mo., USA). The final concentrations of $FeCl_3$ and CORM-2 were 0-10 µM and 0-100 µM, respectively; these concentrations are associated with nearly maximal augmenting effects on coagulation kinetics (see, Sunagar K, et al., J Proteomics 2014; 99:68-83). Plasma was exposed to these various agents for at least 5 min prior to placement into plastic thrombelastographic cups (Haemonetics Inc., Braintree, Mass., USA).

Experimental Plasma Mixtures and Thrombelastographic Analyses.

The final volume for subsequently described plasma sample mixtures was 359.4-359.6 µl. In experiments involving venom obtained from timber and Eastern diamondback rattle snakes, the sample composition consisted of 326 µl of plasma; 10 µl of tissue factor reagent (0.1% final concentration in distilled water; Diagnostica Stago S.A.S., Asnieres sur Seine, France) and 3.4 µl of PBS or venom (final concentration 0.5 µg/ml). In pilot studies, it was determined that the effects of 5 min of incubation at 37° C. with 2.5 µg/ml of either of these two snake venoms provided significant decreases in coagulation kinetic parameter values (e.g., 50% decrease in time to maximum rate of thrombus formation, 50% decrease in the speed of clot formation) before the addition of calcium to commence coagulation. Thus, it was assumed that the thrombin-like activity of these rattlesnakes was not calcium-dependent. However, venom obtained from a Southern Pacific rattlesnake had no effect on coagulation at a concentration as large as 20 µg/ml after incubation in citrated plasma. It was thus assumed that the thrombin-like activity of this snake was calcium-dependent. Consequently, 336 µl of citrated plasma was mixed with 3.6 µl of Southern Pacific rattlesnake plasma (final concentration 10 µg/ml) and calcium chloride as subsequently described. These experiments with Southern Pacific rattlesnake venom had the same four conditions (plasma without addition, CORM-2; plasma with venom, plasma with iron and CORM-2; and, plasma with iron, CORM-2 and venom) as the previous two rattlesnake venom experiments. By using the plastic cup and pin as a weak contact protein activator, sufficient time was permitted for this snake venom to affect fibrinogen in an environment with normal calcium concentrations before the biomechanical events associated with coagulation could be measured. The aforementioned plasma and venom mixtures were placed in a disposable cup in a computer-controlled Thrombelastograph® hemostasis system (Model 5000, Haemonetics Inc., Braintree, Mass., USA) and incubated for 5 min at 37° C., with addition of 20 µl of 200 mM $CaCl_2$ as the last step to initiate clotting. Data were collected at 37° C. for 15 min during experiments involving timber or Eastern diamondback rattlesnakes, whereas samples exposed to Southern Pacific rattlesnake venom had data collected until maximum amplitude was determined by the analyzer software (to allow for variability associated with a lack of a standard incubation time). The following elastic modulus-based parameters previously described (see, Nielsen V G, Pretorius E. Blood Coagul Fibrinolysis 2014; 25:695-702; Nielsen V G, et al., Blood Coagul Fibrinolysis 2011; 22:443-447; Nielsen V G, Pretorius E. Blood Coagul Fibrinolysis 2014; 25:845-850) were determined: time to maximum rate of thrombus generation (TMRTG): this is the time interval (min) observed prior to maximum speed of clot growth; maximum rate of thrombus generation (MRTG): this is the maximum velocity of clot growth observed ($dynes/cm^2/sec$); and total thrombus generation (TTG, $dynes/cm^2$), the final viscoelastic resistance observed after clot formation.

Statistics and Graphics.

Data are presented as mean±SD. The four conditions compared were: 1) additive naïve plasma; 2) plasma exposed to venom; 3) plasma exposed to iron and CORM-2 (Fe/CO) addition; or 4) plasma exposed to Fe/CO addition followed by venom exposure. Each condition was represented by n=6 replicate experiments. A commercially available statistical program was used for one-way analysis of variance followed by Holm-Sidak post hoc analyses (SigmaStat 3.1, Systat Software, Inc., San Jose, Calif., USA). Graphics depicting TMRTG, MRTG and TTG data were generated with a commercially available program (OrigenPro 7.5, OrigenLab Corporation, Northampton, Mass., USA).

Data generated with additive naïve plasma, plasma exposed to venom, plasma exposed to iron and CORM-2 (Fe/CO) addition, or plasma exposed to Fe/CO addition followed by venom exposure are displayed for the three types of rattlesnake in FIGS. 14, 15 and 16. With regard to plasma exposed to timber rattlesnake venom, as depicted in the top panel of FIG. 14, TMRTG values were not significantly affected by venom exposure, but addition of Fe/CO significantly decreased TMRTG values in the absence or presence of venom compared to venom naïve or venom exposed plasma samples. In contrast, as seen in the middle panel of FIG. 14, venom exposure significantly decreased MRTG values when compared to venom naïve plasma; further, addition of Fe/CO significantly increased MRTG values compared to the first two conditions, and venom exposure coupled with Fe/CO addition resulted in MRTG values significantly greater than the other three conditions. Lastly, as displayed in the bottom panel of FIG. 14, with regard to TTG, venom exposure significantly decreased TTG values when compared to venom naïve plasma; further, addition of Fe/CO significantly increased TTG values compared to the first two conditions, and venom exposure coupled with Fe/CO addition resulted in TTG values significantly larger than all other conditions.

As for plasma exposed to Eastern diamondback rattlesnake venom, as depicted in the top panel of FIG. 15, TMRTG values were not significantly affected by venom exposure, but addition of Fe/CO significantly decreased TMRTG values in the absence of venom compared to venom naïve or venom exposed plasma samples, and Fe/CO addition followed by venom exposure resulted in significantly smaller TMRTG values compared to all other conditions. In contrast, as seen in the middle panel of FIG. 15, venom exposure significantly decreased MRTG values when compared to venom naïve plasma; further, addition of Fe/CO significantly increased MRTG values compared to the first two conditions in the absence or presence of venom. Lastly, as noted in the bottom panel of FIG. 15, with regard to TTG, venom exposure significantly decreased TTG values when compared to venom naïve plasma; further, addition of Fe/CO significantly increased TTG values compared to the first two conditions in the presence or absence of venom.

Plasma exposed to Southern Pacific rattlesnake venom had significantly greater TMRTG values (FIG. 16, top panel), significantly smaller MRTG values (FIG. 16, middle panel), and significantly smaller TTG values (FIG. 16, bottom panel) compared to venom naïve plasma. Addition of Fe/CO to venom naïve plasma resulted in TMRTG values significantly smaller than the first two conditions, MRTG values significantly greater than the first two conditions, and TTG values greater than venom exposed plasma. Lastly, plasma with Fe/CO exposed to venom had TMRTG values significantly less than the first two conditions, MRTG values significantly greater than all other conditions, and TTG values significantly greater than plasma samples with or without venom exposure without Fe/CO addition.

The effects of each venom on the three thrombelastographic parameters in plasma are compared in Table 3 for facile reference.

TABLE 3

Comparison of the effects of rattlesnake venom on thrombelastographic parameters.

| Rattlesnake | TMRTG | MRTG | TTG |
| --- | --- | --- | --- |
| Timber Rattlesnaked | NC | ↓ | ↓ |
| Eastern Diamondback | NC | ↓ | ↓ |
| Southern Pacific | ↑ | ↓↓ | ↓↓ |

TMRTG = time to maximum rate of thrombus generation;
MRTG = maximum rate of thrombus generation;
TTG = total thrombus generation;
NC = no change from plasma without venom exposure;
↑ = increased compared to plasma without venom exposure;
↓ = decreased compared to plasma without venom exposure.
Double arrows indicate a greater decrease than that observed with the other two venoms.

The major findings of this investigation include the documentation that plasmatic coagulation kinetics are degraded by the thrombin-like activity from venom of all three rattlesnakes tested. However, the profile of compromised coagulation varied between species (Table 3). Timber rattlesnake venom and Eastern diamondback rattlesnake venoms primarily decreased the speed of thrombus formation and strength, whereas Southern Pacific rattlesnake venom significantly delayed the onset of maximum speed of clot growth as well as significantly decreased the speed of clot growth and strength. Critically, addition of Fe/CO abrogated all venom mediated degradations of coagulation derived from all three rattlesnakes. Further, each venom demonstrated a thrombin-like activity that positively enhanced coagulation in samples with Fe/CO addition; specifically, timber rattlesnake venom enhanced MRTG and TTG values, Eastern diamondback rattlesnake venom enhanced TMRTG values, and Southern Pacific rattlesnake venom enhanced MRTG values. Considered as a whole, these unique observations support the concept that the molecular targets of thrombin and the various venoms on fibrinogen are distinct from one another, and that their sequential activation may result in a negative or positive, additive effect on coagulation depending on the configuration of fibrinogen. Put another way, the proposed mechanism by which iron and CO may protect coagulation from venom thrombin like activity is by creating a "stealth fibrinogen" that is not seen molecularly by venom proteases.

The amount of iron and CORM-2 used in vitro in the present investigation is significantly less than has been administered in vivo (see, Nielsen V G, Arkebauer M R, et al., Blood Coagul Fibrinolysis 2012; 3:104-107; Kshirsagar A V, et al., PLoS ONE 2013; 8:e78930) including in the clinical setting. Using a rabbit ear-bleed model, CORM-2 was injected at a dose of 10 mg/kg (equivalent to 279 µM final concentration) to effect CO mediated resistance to tissue-type plasminogen mediated coagulopathy without adverse effects noted (see, Nielsen V G, Arkebauer M R, et al., Blood Coagul Fibrinolysis 2012; 3:104-107). As for iron, in order to administer a dose that would result in an increase of 10 µM in the circulation, consider the following: assuming a molecular weight of 55.8 atomic mass units for elemental iron, multiply 0.558 µg/ml by 70 ml/kg (estimated blood volume) and by 70 kg (an average weight), for a final result of approximately 2.7 mg of iron. It is clinical practice to infuse up to 100 mg of iron to augment red blood cell production, a value more than 30-fold of the amount required to enhance coagulation (see, Kshirsagar A V, et al., PLoS ONE 2013; 8:e78930). In sum, administration of iron and CO in the quantities required to modify fibrinogen to attenuate degradation by thrombin-like activity in the venom of the rattlesnakes tested may be clinically achievable without adverse effects.

These findings also have implications for diagnostic data collection of snakebite victims. Fibrinogen concentrations are typically measured from citrated plasma, and if a venom's activity is calcium-independent, then the concentration of fibrinogen may be artificially decreased if there is a prolonged time from collection to analysis in the clinical laboratory. In contrast, calcium-dependent venoms would not cause such an artifact; thus, one might expect that blood samples obtained by patients bitten by a timber or Eastern diamondback rattlesnake may have very small fibrinogen concentrations, especially if some delay in centrifugation or other processing steps prolonged the time to analysis. In sum, the data of the present investigation should also give clinical laboratorians pause when considering the diagnostic evaluation of plasma fibrinogen concentration for the care of snakebite patients.

It is important to consider the multiple regional and systemic effects of snake venom, which are mediated in part by zinc metalloproteinases that induce a hemorrhagic state and myotoxins that destroy vascular endothelial and muscle cells, resulting in pulmonary and circulatory failure (see, Lefkowitz R Y, et al., J Intensive Care Med 2013; 28:314-319; Massey D J, et al., J Proteomics 2012; 75:2576-2587; Lavonas E J, et al., Ann Emerg Med 2011; 57:128-137). Further, the tissue damage that occurs may permanently debilitate the snakebite victim that often times requires surgical intervention that include fasciotomies for ischemic compartment syndromes (see, Toschlog E A, et al., J Am Coll Surg 2013; 217:726-735). It is not proposed that preserving fibrinogen with iron and CO administration will attenuate all the other effects of crotaline venoms, but instead is possible such intervention will at least potentially diminish coagulopathy in snakebite victims. Further, administration of blood products pretreated with iron and CO (e.g., fresh frozen plasma, cryoprecipitate) may have a longer intravascular duration in such patients. In sum, the utilization of iron and CO to protect fibrinogen from venom mediated digestion is envisioned as a part of a multimodal approach to treat patients envenomed with hemotoxic enzymes.

Example V

A variety of rattlesnake species found in populous regions throughout western North America have defibrinogenating venoms (see, Mackessy S P. Toxicon 1996; 34:1277-1285; Mackessy S P. Toxicon 2010; 55:1463-1474; Komori Y, et al., Biochim Biophys Acta 1988; 967:92-102; Komori Y, et al., Int J Biochem 1994; 26:1411-8; Mori N, et al., Arch Biochem Biophys 1987; 253:108-121; Mackessy S P. \Toxicon 1985; 23:337-340; Mori N, Int J Biochem 1988; 20:1425-1433; Komori Y, et al., Toxins (Basel) 2011; 3:900-910) that contain serine proteases and metalloproteinases (see, Kini R M. Pathophysiol Haemost Thromb 2005; 34:200-204; Markland Jr. F S, Swenson S. Toxicon 2013; 62:3-18). While antibodies to venom compounds and enzymes in antivenom usually initially attenuate destruction of circulating fibrinogen, another potential approach to preserving circulating fibrinogen exists that is not snake species-specific. This strategy involves changing the structural configuration of fibrinogen with recently described interactions with iron and carbon monoxide (CO). Specifically, recent investigations have revealed that plasmatic fibrinogen exposed to iron and CO forms thrombi that are structurally different from plasma without such exposures, and coagulation commences earlier, with greater formation velocity and final clot strength compared to clots that are iron and CO naïve (see, Nielsen V G, Pretorius E. Blood Coagul Fibrinolysis 2014; 25:695-702). CO binds to heme(s) bound to fibrinogen (see, Nielsen V G, et al., Blood Coagul Fibrinolysis 2011; 22:443-447), and iron and heme have been found to bind to fibrinogen (see, Orino K. Biometals 2013; 26:789-794), with chelation of iron noted to reverse both structural and coagulation kinetic changes in plasma thrombi (see, Nielsen V G, Pretorius E. et al., Blood Coagul Fibrinolysis 2014; 25:845-850). Iron and CO enhance fibrinogen by separate mechanisms; iron decreases the time to onset of coagulation and increases the velocity of clot formation without affecting final clot strength, whereas CO increases the velocity of clot formation and increases clot strength without affecting the time to onset of coagulation (see, Nielsen V G, Pretorius E. Blood Coagul Fibrinolysis 2014; 25:695-702). When combined, the velocity of clot formation increases in an additive manner by both these agents (see, Nielsen V G, Pretorius E. Blood Coagul Fibrinolysis 2014; 25:695-702). Also of interest, exposure to CO resulted in the inability to recover significant portions of the γ chain after endopeptidase treatment of purified fibrinogen during mass spectroscopic analysis (see, Nielsen V G, et al., Blood Coagul Fibrinolysis 2011; 22:443-447), indirect evidence of molecular conformational change of fibrinogen. Finally, demonstration of significant, but species specific success in attenuating venom mediated compromise of plasmatic coagulation by *Crotalus atrox* (see, Nielsen V G, Boyer L V. Iron and carbon monoxide attenuate degradation of plasmatic coagulation by *Crotalus atrox* venom. Blood Coagul Fibrinolysis, in press) and various *Agkistrodon* species (see, Nielsen V G, Redford D T, Boyle P K. Effect of iron and carbon monoxide on fibrinogenase-like degradation of plasmatic coagulation by venoms of six *Agkistrodon* species. Basic Clin Pharmacol Toxicol, in press) with iron and CO pretreatment. Taken as a whole, these data suggested that it may be possible to change the three-dimensional configuration of fibrinogen with iron and CO such that thrombin could interact with it as an enhanced substrate, but perhaps fibrinogenolytic-like activity in similar snake venoms could not.

The hypothesis of the following experiments was that pretreatment of plasma with iron and CO may attenuate the ability of the venom of four commonly encountered rattlesnake species found in western North America to catalyze fibrinogen and compromise coagulation kinetics.

Pooled normal human plasma (George King Bio-Medical, Overland Park, Kans., USA) anticoagulated with sodium citrate (9 parts blood to 1 part 0.105M sodium citrate) stored at −80° C. was utilized in all subsequently described experiments. Two-hundred mg of lyophilized snake venom obtained from each species was obtained from the National Natural Toxins Research Center at Texas A&M University, Kingsville, Tex., USA. The four venom samples were individually reconstituted in calcium-free phosphate buffered saline (PBS, Sigma-Aldrich, Saint Louis, Mo., USA) at a concentration of 50 mg/ml, aliquoted, and stored at −80° C. until experimentation.

Plasma was rapidly thawed at 37° C. on the day of experimentation. Plasma had 1% additions of ferric chloride ($FeCl_3$, 99.9% pure, Sigma-Aldrich, Saint Louis, Mo., USA) in phosphate buffered saline) or CORM-2 (tricarbonyldichlororuthenium (II) dimer, a CO releasing molecule, Sigma-Aldrich, Saint Louis, Mo., USA) dissolved in dimethyl sulfoxide (Sigma-Aldrich, Saint Louis, Mo., USA). The final concentrations of $FeCl_3$ and CORM-2 were 0-10 μM and 0-100 μM, respectively; these concentrations are associated with nearly maximal augmenting effects on coagulation kinetics (see, Nielsen V G, Blood Coagul Fibrinolysis 2014; 25:695-702). All samples had 1% DMSO and PBS additions with or without the aforementioned chemicals, so all samples were controlled for the vehicles used. Plasma was exposed to these various agents for at least 5 min prior to placement into plastic thrombelastographic cups (Haemonetics Inc., Braintree, Mass., USA).

The final volume for subsequently described plasma sample mixtures was 359.4 μl. In experiments involving venom obtained from *Crotalus oreganus oreganus* and *Crotalus oreganus cerberus*, the sample composition consisted of 326 μl of plasma; 10 μl of tissue factor reagent (STA NeoplastineCL+5, catalogue #00606; 0.1% final concentration in distilled water; Diagnostica Stago S.A.S., Asnieres sur Seine, France) and 3.4 μl of PBS or venom (final concentration 0.5 μg/ml). In pilot studies, it was determined that the effects of 5 min of incubation at 37° C. with 2.5 μg/ml of either of these two snake venoms provided significant decreases in coagulation kinetic parameter values (e.g., 50% decrease in time to maximum rate of thrombus formation, 50% decrease in the speed of clot formation) before the addition of calcium to commence coagulation. Thus, it was assumed that the fibrinogenolytic-like activity of these rattlesnakes was not calcium-dependent. However, venom obtained from either *Crotalus viridis viridis* or *Crotalus ruber ruber* had an effect on coagulation in pilot studies only at concentrations 20 to 40 fold greater than the preceding two rattlesnakes. It was thus assumed that the fibrinogenolytic-like activity of these snakes' venoms was calcium-dependent, far less potent than the other snakes, or that the venom simply did not possess fibrinogenolytic activity. Consequently, 336 μl of citrated plasma was mixed with 3.6 μl of *Crotalus viridis viridis* or *Crotalus ruber ruber* venom and calcium chloride as subsequently described. These experiments with *Crotalus viridis viridis* or *Crotalus ruber ruber* venom had the same four conditions (plasma without venom, iron, CORM-2; plasma with venom, plasma with iron and CORM-2; and, plasma with iron, CORM-2 and venom) as the previous series of experiments with *Crotalus oreganus oreganus* and *Crotalus oreganus cerberus* venom. By using the plastic cup and pin as a weak contact protein activator, sufficient time was permitted for these snake venoms to affect fibrinogen in an environment with normal calcium concentrations before the biomechanical events associated with coagulation could be measured.

The aforementioned plasma and venom mixtures were placed in a disposable cup in a computer-controlled Thrombelastograph® hemostasis system (Model 5000, Haemonetics Inc., Braintree, Mass., USA), with addition of 20 μl of 200 mM $CaCl_2$ as the last step to initiate clotting. Data were collected at 37° C. for 15 min during experiments involving *Crotalus oreganus oreganus* and *Crotalus oreganus cerberus*, whereas samples exposed to *Crotalus viridis viridis* or *Crotalus ruber ruber* venom had data collected until maximum amplitude was determined by the analyzer software (to allow for variability associated with a lack of a standard incubation time). The following elastic modulus-based parameters previously described (see, Nielsen V G, et al., Blood Coagul Fibrinolysis 2014; 25:695-702; Nielsen V G, et al., Blood Coagul Fibrinolysis 2011; 22:443-447; Nielsen V G, et al., Blood Coagul Fibrinolysis 2014; 25:845-850) were determined: time to maximum rate of thrombus generation (TMRTG): this is the time interval (min) observed prior to maximum speed of clot growth; maximum rate of thrombus generation (MRTG): this is the maximum velocity of clot growth observed ($dynes/cm^2/sec$); and total thrombus generation (TTG, $dynes/cm^2$), the final viscoelastic resistance observed after clot formation.

Data are presented as mean+SD. Each condition was represented by n=6 replicate experiments. A commercially available statistical program was used for one-way analysis of variance followed by Holm-Sidak post hoc analyses (SigmaStat 3.1, Systat Software, Inc., San Jose, Calif., USA). Graphics depicting TMRTG, MRTG and TTG data were generated with a commercially available program (OrigenPro 7.5, OrigenLab Corporation, Northampton, Mass., USA).

Data generated by exposure of plasma to no additives (control), venom (V) addition, or iron and CORM-2 prior to venom (Fe/CO/V) addition, are displayed in for the six snakes in FIGS. 1-4. Separate paragraphs of the findings of each species will be subsequently presented to improve clarity.

*Crotalus oreganus oreganus.*

The concentration of venom used was 1 μg/ml. As can be seen in FIG. 17, exposure to venom significantly increased TMRTG (top panel), decreased MRTG (middle panel), and decreased TTG (bottom panel). Pretreatment with iron and CO significantly decreased the effects of venom on TMRTG, reducing these values to the point of not being significantly different from control plasma values. Lastly, pretreatment with iron and CO significantly increased MRTG and TTG values when compared to control plasma or venom exposed plasma.

*Crotalus oreganus cerberus.*

The concentration of venom used was 2 μg/ml. As can be seen in FIG. 18, exposure to venom significantly increased TMRTG (top panel), decreased MRTG (middle panel), and decreased TTG (bottom panel). Pretreatment with iron and CO did significantly decrease the effects of venom on TMRTG, but did significantly decrease these values back to control plasma sample values. However, iron and CO pretreatment resulted in MRTG and TTG values significantly greater than control plasma or venom exposed plasma values.

*Crotalus viridis viridis.*

The concentration of venom used was 10 µg/ml. As can be seen in FIG. 19, exposure to venom significantly increased TMRTG (top panel), decreased MRTG (middle panel), and decreased TTG (bottom panel). Pretreatment with iron and CO significantly decreased the effects of venom on TMRTG, reducing these values to the point of not being significantly less than control plasma values. Lastly, pretreatment with iron and CO significantly increased MRTG and TTG values when compared to control plasma or venom exposed plasma.

*Crotalus ruber ruber.*

The concentration of venom used was 10 µg/ml. As can be seen in FIG. 20, exposure to venom significantly decreased TMRTG (top panel), did not affect MRTG (middle panel), and significantly decreased TTG (bottom panel). With regard to TMRTG, iron and CO pretreatment of plasma resulted in values significantly smaller than venom exposed plasma or control plasma. Further, pretreatment with iron and CO significantly increased MRTG and TTG values compared to venom exposed plasma and control plasma. Critically, the action of this venom (decreasing TMRTG values, not increasing them) was not consistent with fibrinogenolysis as with the other three *Crotalus* species venoms; instead, it was consistent with thrombin-like activity.

The present investigation revealed that three more rattlesnake species documented to possess venoms with fibrinogenolytic activity (see, Mackessy S P. Toxicon 1996; 34:1277-1285; Mackessy S P. Toxicon 2010; 55:1463-1474; Komori Y, et al., Biochim Biophys Acta 1988; 967:92-102; Komori Y, et al., Int J Biochem 1994; 26:1411-8) compromised plasmatic coagulation as determined by thrombelastography. Further, pretreatment of plasma with iron and CO markedly attenuated venom mediated compromise of coagulation kinetics by *Crotalus oreganus oreganus*, *Crotalus oreganus cerberus* and *Crotalus viridis viridis*. In sum, for at least four species of rattlesnake with fibrinogenolytic activity tested, fibrinogen can be protected from venom mediated degradation.

Unlike the other snakes tested, the present study found that the venom of *Crotalus ruber ruber* was weakly prothrombotic (decreased TMRTG) and degraded clot strength (TTG). This particular combination of effects could be caused by simultaneous decreased TMRTG values secondary to previously documented kallikrein-like activity in this snake's venom (see, Mori N, et al., Int J Biochem 1988; 20:1425-1433) coupled with decreased TTG values via loss of fibrinogen by a fibrinogenolytic component of the raw venom (see, Mori N, et al., Arch Biochem Biophys 1987; 253:108-121). Pretreatment with iron and CO followed by exposure to *Crotalus ruber ruber* venom even more markedly decreased TMRTG values, and the effects of the venom on clot strength were abrogated. Taken as a whole, this particular snake's venom is not particularly potent compared to the other three tested, and iron and CO pretreatment may have accentuated kallikrein-like activity effects (via increased thrombin generation) and attenuated fibrinogenolytic-like activity effects by modifying fibrinogen.

The amount of iron and CORM-2 used in vitro in the present investigation is significantly less than has been administered in vivo (see, Nielsen V G, et al., Blood Coagul Fibrinolysis 2012; 23:104-107; Kshirsagar A V, et al., PLoS ONE 2013; 8:e78930) including in the clinical setting. Using a rabbit ear-bleed model, CORM-2 was injected at a dose of 10 mg/kg (equivalent to 279 µM final concentration) to effect CO mediated resistance to tissue-type plasminogen mediated coagulopathy without adverse effects noted (see, Nielsen V G, et al., Blood Coagul Fibrinolysis 2012; 23:104-107). As for iron, in order to administer a dose that would result in an increase of 10 µM in the circulation, consider the following: assuming a molecular weight of 55.8 atomic mass units for elemental iron, multiply 0.558 µg/ml by 70 ml/kg (estimated blood volume) and by 70 kg (an average weight), for a final result of approximately 2.7 mg of iron. It is clinical practice to infuse up to 100 mg of iron to augment red blood cell production, a value more than 30-fold of the amount required to enhance coagulation (see, Kshirsagar A V, et al., PLoS ONE 2013; 8:e78930). In sum, administration of iron and CO in the quantities required to modify fibrinogen to attenuate degradation by thrombin-like activity in the venom of the rattlesnakes tested may be clinically achievable without adverse effects.

This investigation utilized changes in coagulation kinetics of citrated human plasma to characterize the effects of snake venom and the effects of Fe/CO pretreatment on those changes to assess changes in functional fibrinogen and protection from venom mediated changes as in very recent studies. The reason that this is a valid approach is that the effects of various snake venoms on fibrinogen have been identified as the major plasmatic legion (see, Markland Jr. F S, et al., *Toxicon* 2013; 62:3-18; Mackessy S P. *Toxicon* 1996; 34:1277-1285), and it has been demonstrated that iron and carbon monoxide enhance coagulation by exclusive modulation of fibrinogen (see, Nielsen V G, et al., Blood Coagul Fibrinolysis 2014; 25:695-702; Nielsen V G, et al., Blood Coagul Fibrinolysis 2011; 22:443-447; Nielsen V G, et al., Blood Coagul Fibrinolysis 2014; 25:845-850; Nielsen V G, et al., Blood Coagul Fibrinolysis 2009; 20:377-380. Rather than repeat work describing the fragments released from by fibrinogen by these venoms, the new dimension of changes in the function of fibrinogen under the various conditions of the experiments were introduced.

Example VI

*Crotalus* and *Agkistrodon* specie venom is fibrinogenolytic as previously described (see, Budzynski A Z, et al., Blood. 1984; 63(1): 1-14; Chiou S H, et al., Biochem Biophys Res Comm. 1992; 187(1):389-396; Walter F G, et al., South Med J. 2012; 105(6):313-320; Walter F G, et al., South Med J. 2014; 107(3): 150-156), typically containing metalloproteinases and/or serine proteases (see, Bell W R. Drugs. 1997; 54(Suppl 3); 18-31; Markland Jr. F S, et al., Toxicon. 2013; 62:3-18; Kini R M. Pathophysiol Haemost Thromb. 2005; 34(4-5):200-204). Consequent hypofibrinogenemia contributes to hemorrhage following such envenomation (see, Budzynski A Z, et al., Blood. 1984; 63(1):1-14; Walter F G, et al., South Med J. 2014; 107(3):150-156). It has been demonstrated that pre-exposure of human plasma to small concentrations of iron and carbon monoxide (CO) causes plasma to be resistant to degradation of coagulation by *Crotalus* and *Agkistrodon* specie venoms (see, Nielsen V G, Boyer L V. Iron and carbon monoxide attenuate degradation of plasmatic coagulation by *Crotalus atrox* venom. Blood Coagul Fibrinolysis. In press; Nielsen V G, Redford D T, Boyle P K. Effect of iron and carbon monoxide on fibrinogenase-like degradation of plasmatic coagulation by venoms of six *Agkistrodon* species. Basic Clin Pharmacol Toxicol. In press; Nielsen V G, Redford D T, Boyle P K. Effect of iron and carbon monoxide on fibrinogenase-like degradation of plasmatic coagulation by venoms of four *Crotalus* species. Blood Coagul Fibrinolysis. In press). The putative mechanism for iron/CO mediated protection is that these agents change the configuration of fibrinogen, making molecular recognition of catalytic sites by venom less favorable, based on the changes in ultrastructure of plasma clots mediated by iron/CO (see, Nielsen V G, Pretorius E. Blood Coagul Fibrinolysis. 2014; 25(7):695-702). In sum, the addition of iron/CO to plasma appears to indirectly attenuate the effects of fibrinogenase activity from a variety of species of venomous snakes on coagulation.

However, the direct effects of iron/CO on venom in isolation were not determined, as the authors knew enzymes in venom, particularly the metalloproteinases, are quite resistant to inhibition in envenomed animals. Thus, when preliminary experiments to verify that iron/CO would not inhibit venom demonstrated the opposite effect, the decision to formally test this serendipitous finding was made. Thus, the purpose of the experiments conducted for this Example were to determine if exposure of isolated venom to iron and CO (in combination and separately) diminish fibrinogenolysis in human plasma.

Materials.

*C. atrox* venom was obtained from the National Natural Toxins Research Center at Texas A&M University-Kingsville, Tex., USA. Venom was reconstituted in calcium-free phosphate buffered saline (PBS, Sigma-Aldrich, Saint Louis, Mo., USA), and stored at −80° C. Pooled human normal plasma anticoagulated with sodium citrate was obtained from George King Bio-Medical, Overland Park, Kans., USA. Ferric chloride ($FeCl_3$, 99.9% pure), tricarbonyldichlororuthenium (II) dimer (CORM-2), and dimethyl sulfoxide (DMSO) were obtained from Sigma-Aldrich. The final concentrations of $FeCl_3$ (dissolved in PBS) and CORM-2 (dissolved in DMSO) were 0-10 µM and 0-100 µM, respectively; these were the concentrations used in previous works involving the effects of modifying fibrinogen prior to venom exposure in plasma. To isolate the effects of CO from the carrier molecule of CORM-2, a 100 µM solution of CORM-2 was placed in a sealed plastic tube and incubated in a to a 37° C. water bath for 18 hours in order to release CO and become inactive (iCORM-2) as has been previously described (see, Nielsen V G, Garza J I. Blood Coagul Fibrinolysis. 2014; 25(8):801-805).

Isolated Venom Exposure Experiments.

To increase the detection of effects of iron/CO on venom activity, the concentration of venom chosen for isolated exposure and for addition to plasma was twice the amount expected to eliminate coagulation based on previous work (see, Nielsen V G, Boyer L V. Iron and carbon monoxide attenuate degradation of plasmatic coagulation by *Crotalus atrox* venom. Blood Coagul Fibrinolysis. In press). A 1 ml quantity of a 200 µg/ml solution of venom in PBS was prepared for each condition subsequently presented. The conditions were: 1) 1% addition (v/v) of PBS and DMSO to PBS without venom; 2) 1% addition (v/v) of PBS and DMSO to PBS with venom; 3) 1% addition of $FeCl_3$ and CORM-2 to PBS without venom; 4) 1% addition of $FeCl_3$ and CORM-2 to PBS with venom; 5) 1% addition of $FeCl_3$ and DMSO to PBS with venom; 6) 1% addition of CORM-2 to PBS with venom; and lastly, 7) 1% addition of PBS and iCORM-2 to PBS with venom. After 3 min of incubation at room temperature, 3.6 µl of solution from one of these conditions was placed into 326 µl of plasma and 10 µl of tissue factor reagent (0.1% final concentration in distilled water; Diagnostica Stago S.A.S., Asnieres sur Seine, France) in a disposable cup in a computer-controlled Thrombelastograph® hemostasis system (Model 5000, Haemonetics Inc., Braintree, Mass., USA). After test solution addition, 20 µl of 200 mM $CaCl_2$ was immediately added to initiate clotting. Data were collected at 37° C. for 15 min. The following parameters previously described (see, Nielsen V G, Boyer L V. Iron and carbon monoxide attenuate degradation of plasmatic coagulation by *Crotalus atrox* venom. Blood Coagul Fibrinolysis. In press; Nielsen V G, Redford D T, Boyle P K. Effect of iron and carbon monoxide on fibrinogenase-like degradation of plasmatic coagulation by venoms of six *Agkistrodon* species. Basic Clin Pharmacol Toxicol. In press; Nielsen V G, Redford D T, Boyle P K. Effect of iron and carbon monoxide on fibrinogenase-like degradation of plasmatic coagulation by venoms of four *Crotalus* species. Blood Coagul Fibrinolysis. In press; Nielsen V G, Pretorius E. Blood Coagul Fibrinolysis. 2014; 25(7):695-702; Nielsen V G, Garza J I. Blood Coagul Fibrinolysis. 2014; 25(8):801-805) were determined: time to maximum rate of thrombus generation (TMRTG): this is the time interval (min) observed prior to maximum speed of clot growth; maximum rate of thrombus generation (MRTG): this is the maximum velocity of clot growth observed ($dynes/cm^2/sec$); and total thrombus generation (TTG, $dynes/cm^2$), the final viscoelastic resistance observed after clot formation.

Data are presented as median ($1^{st}$-$3^{rd}$ quartiles). All conditions were represented by n=6 replicates. This number of replicates were used as a statistical power >0.8 has been observed with similar analyses with this in vitro model. If no coagulation occurred, the sample observed was assigned a TMRTG value of 15 min, with values for MRTG and TTG designated as 0. Thus, as the data were not normally distributed, Kruskall-Wallis one-way analysis of variance followed by Student-Newman-Keuls post hoc test were used for analyses (SigmaStat 3.1, Systat Software, Inc., San Jose, Calif., USA). P<0.05 was considered significant.

Coagulation kinetic data are displayed in Table 4. Compared to plasma with addition of PBS/DMSO, the further addition of venom resulted in a significant, and essentially complete lack of coagulation. Addition of PBS containing $FeCl_3$/CORM-2 resulted in coagulation kinetic parameters not significantly different from plasma exposed to PBS/DMSO, but significantly different from samples exposed to venom. Similarly, addition of PBS with venom exposed to $FeCl_3$/CORM-2 resulted in coagulation kinetic parameters not significantly different from plasma exposed to PBS/DMSO, but significantly different from samples exposed to venom. When PBS with venom exposed to $FeCl_3$ was tested, absence of coagulation not different from samples exposed to venom alone was observed. In contrast, PBS containing venom exposed to CORM-2 added to plasma produced coagulation kinetic values not different from PBS/DMSO exposed plasma, but significantly different from plasma mixed with venom with PBS/DMSO exposure. Lastly, addition of PBS with venom exposed to iCORM-2 to plasma resulted in no discernable coagulation, significantly different from the results observed with PBS/DMSO exposed plasma but not different from plasma samples containing venom with PBS/DMSO exposure.

TABLE 4

Effects of FeCl₃, CORM-2 and CO on venom fibrinogenolysis in plasma.

| Condition | TMRTG | MRTG | TTG |
|---|---|---|---|
| Effects of combinations of vehicle, venom and FeCl₃ + CORM-2 on coagulation | | | |
| DMSO/PBS vehicle | 3.7 (3.2, 3.8) | 4.7 (4.1, 5.3) | 168 (153, 174) |
| Venom | 15.0 (15.0, 15.0)* | 0.0 (0.0, 0.0)* | 0 (0, 1)* |
| FeCl₃ + CORM-2 | 3.7 (3.2, 3.8)† | 5.0 (4.8, 5.2)† | 168 (165, 176)† |
| Venom + FeCl₃ + CORM-2 | 3.2 (3.0, 3.3)† | 5.2 (4.9, 5.6)† | 176 (169, 182)† |
| Effects of FeCl₃ exposed venom on coagulation | | | |
| Venom + FeCl₃ | 15.0 (15.0, 15.0)* | 0.0 (0.0, 0.0)* | 0 (0, 0)* |
| Effects of CORM-2 or inactivated CORM-2 (iCORM-2) exposed venom on coagulation | | | |
| Venom + CORM-2 | 3.0 (3.0, 3.1)*† | 5.9 (5.7, 6.1)*† | 172 (168, 178)† |
| Venom + iCORM-2 | 15.0 (15.0, 15.0)*‡ | 0.0 (0.0, 0.0)*‡ | 0.0 (0.0, 0.0)*‡ |

DMSO/PBS vehicle = 1% addition of each of these vehicles to PBS solution without venom addition;
Venom = 2 µg/ml final concentration of C. atrox venom in DMSO/PBS vehicle solution;
FeCl₃ + CORM-2 = PBS solution with 10 µM FeCl₃ and 100 µM CORM-2 final concentration;
Venom + FeCl₃ + CORM-2 = venom 2 µg/ml final concentration exposed to 10 µM FeCl₃ and 100 µM CORM-2;
Venom + FeCl₃ = venom 2 µg/ml final concentration exposed to 10 µM FeCl₃;
Venom + CORM-2 = venom 2 µg/ml final concentration exposed to 100 µM CORM-2;
Venom + iCORM-2 = venom 2 µg/ml final concentration exposed to 100 µM iCORM-2.
*P < 0.05 vs. DMSO/PBS vehicle;
†P < 0.05 vs. Venom;
‡P < 0.05 vs. Venom + CORM-2.

The primary finding of the present investigation was that CO derived from CORM-2 completely inhibited the effects of *C. atrox* venom (which possesses a metalloproteinase, Catroxase²) on plasmatic coagulation. Further, iron and the carrier molecule of CORM-2 had no appreciable effects on venom activity, and no interference with CO mediated inhibition of venom activity by iron and iCORM-2 was observed. CO derived from CORM-2 has only once been demonstrated to directly inhibit the activity of metalloproteinases 1 and 2 in a human alveolar epithelial cell line (see, Desmard M, et al., Cell Mol Biol. 2005; 51(4):403-408). The results indicate that CO, being known to preferentially bind to transition metal centers, could have bound to the $Zn^{+2}$ metal located in the catalytic center of the enzyme as the mechanism of inhibition. Given that the $Zn^{+2}$ ion contained in snake venom metalloproteinases have been demonstrated to be critical to ligand binding via molecular dynamic simulation (see, Chinnasamy S, et al., RSC Adv. 2015; 5:70566-70576), and that most of these enzymes possess $Zn^{+2}$ containing catalytic centers (see, Markland Jr. F S, Swenson S. Toxicon. 2013; 62:3-18), the findings may have broad implications. For example, in addition to hemostatic effects, snake venom $Zn^{+2}$ metalloproteinases also induce a hemorrhage and circulatory failure (see, Markland Jr. F S, Swenson S. Toxicon. 2013; 62:3-18). If CO inactivates a significant number of such snake venom $Zn^{+2}$ metalloproteinases, then a new potential therapeutic direction for the treatment of envenomation may be possible.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of protecting a subject from venom related fibrinogenolytic activity, comprising administering to the subject in need thereof a therapeutically effective amount of a composition comprising a carbon monoxide releasing molecule (CORM) wherein the CORM is selected from the group consisting of tricarbonyldichlororuthenium (II) dimer, tricarbonylchloro(glycinato)ruthenium (II), sodium boranocarbonate, dimanganese decacarbonyl, and iron pentacarbonyl, wherein the administering of the composition results in interaction of venom within the subject and the composition, wherein such interaction results in inactivation of fibrinogenolytic activity in the venom thereby protecting the subject from venom related fibrinogenolytic activity.

2. The method of claim 1, wherein the composition comprises between about 25 µM to about 200 µM of the CORM or 350-1000 mg of the CORM.

3. The method of claim 1, wherein the composition further comprises an iron releasing molecule (IRM).

4. The method of claim 3, wherein the administering results in release of carbon monoxide from the CORM and iron from the IRM.

5. The method of claim 3,
   wherein the IRM is selected from the group consisting of ferric chloride, iron dextran, ferric gluconate, iron sucrose, ferumoxytol, ferric carboxymaltose, and iron isomaltoside.

6. The method of claim 1, wherein the composition comprises between 5-25 mg of the IRM.

7. The method of claim 1, wherein the composition is a pharmaceutical composition.

8. The method of claim 1, wherein inactivation of fibrinogenolytic activity in the venom prevents one or more of
venom mediated catalysis of fibrinogen in the subject,
venom mediated degradation of plasma coagulation in the subject, and
venom mediated coagulopathy in the subject.

9. The method of claim 1, wherein the venom is *Crotalus* related venom, wherein the *Crotalus* related venom is a venom from a *Crotalus* species selected from *C. adamanteus, C. aquilus, C. atrox, C. basilicus, C. cerastes, C. durissus, C. enyo, C. horridus, C. intermedius, C. lannomi, C. lepidus, C. mitchellii, C. molossus, C. oreganus, C. polystictus, C. pricei, C. pusillus, C. ruber, C. scutulatus, C. simus, C. stejnegeri, C. tigris, C. tortugensis, C. totonacus, C. transversus, C. triseriatus, C. viridis*, and *C. willardi*.

10. The method of claim 1, wherein the venom is from one of the following: *Naja naja* (Indian cobra), *Bothrops asper* (Fur-de-lance), *Agkistrodon piscivorus piscivorus, Agkistrodon contortrix contortrix, Agkistrodon contortrix laticinctus, Askistrodon contortix pictigaster, Agkistrodon piscivorus leucostoma, Agkistrodon contortrix mokasen,* Northern Pacific rattlesnake, Arizona Black rattlesnake, Prairie rattlesnake, Red Diamond rattlesnake, Timber rattlesnake, Eastern Diamondback rattlesnake, and Southern Pacific rattlesnake.

11. The method of claim 1, wherein the subject is a living mammal.

12. The method of claim 1, wherein the subject is a human subject.

* * * * *